US008937039B2

(12) United States Patent
Zhang et al.

(10) Patent No.: US 8,937,039 B2
(45) Date of Patent: Jan. 20, 2015

(54) PEPTIDE-BASED PEROXIDASE INHIBITORS AND METHODS OF USING SAME

(71) Applicants: Hao Zhang, New Berlin, WI (US); Yang Shi, Wauwatosa, WI (US); Hao Xu, Elm Grove, WI (US); Kirkwood A. Pritchard, Jr., Elm Grove, WI (US)

(72) Inventors: Hao Zhang, New Berlin, WI (US); Yang Shi, Wauwatosa, WI (US); Hao Xu, Elm Grove, WI (US); Kirkwood A. Pritchard, Jr., Elm Grove, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 14/081,695

(22) Filed: Nov. 15, 2013

(65) Prior Publication Data

US 2014/0194342 A1    Jul. 10, 2014

Related U.S. Application Data

(63) Continuation-in-part of application No. 13/500,040, filed as application No. PCT/US2010/051425 on Oct. 5, 2010, now Pat. No. 8,673,847.

(60) Provisional application No. 61/248,627, filed on Oct. 5, 2009.

(51) Int. Cl.
*A61K 38/06*   (2006.01)
*A61P 9/12*    (2006.01)
*A61P 19/02*   (2006.01)
*C07K 5/09*    (2006.01)

(52) U.S. Cl.
CPC .................................. *C07K 5/0815* (2013.01)
USPC ......... 514/1.4; 514/21.9; 514/17.7; 514/15.7; 514/17.8; 514/19.3

(58) Field of Classification Search
None
See application file for complete search history.

(56) References Cited

U.S. PATENT DOCUMENTS

| | | | |
|---|---|---|---|
| 6,815,422 B2 | 11/2004 | Albini et al. | |
| 6,858,581 B2 * | 2/2005 | Kuhner et al. | 514/2.4 |
| 2005/0113297 A1 | 5/2005 | Francois et al. | |
| 2006/0074026 A1 | 4/2006 | Hazen et al. | |

OTHER PUBLICATIONS

Zhang et al. (J Biol Chem 280(49) (2005): 40684-40698).*
Heinecke et al. (J Clin Invest 91 (1993): 2866-2872).*
Winterbourn et al ("Myeloperoxidase" (2000) Current Opinion in Hematology 7(1): 53-58).*
Zhang, et al., Intramolecular Electron Transfer Between Tyrosyl Radical and Cysteine Residue Inhibits Tyrosine Nitration and Induces Thiyl Radical Formation in Model Peptides Treated with Myeloperoxidase, H2O2 and NO2, Journal of Biological Chemistry, 2005, 280 (49):40684-40698.
Zhang, et al., Influence of Intramolecular Electron Transfer Mechanism in Biological Nitration, Nitrosation, and Oxidation of Redox-Sensitive Amino Acids, Methods in Enzymology, 2008, 440:65-94.
Zhang, et al., The Effect of Neighboring Methionine Residue on Tyrosine Nitration & Oxidation in Peptides Treated with MPO, H2O2, & NO2 or Peroxynitrite and Bicarbonate: Role of Intramolecular Electron-Transfer Mechanism?, Arch. Biochem. Biophys., 2009, 484(2):134-145.
Zheng, et al., Apolipoprotein A-1 is a Selective Target for Myeloperoxidase-Catalyzed Oxidation and Functional Impairment in Subjects with Cardiovascular Disease, Journal of Clinical Investigation, 2004, 114:529-541.
PCT International Search Report and Written Opinion, PCT/US2010/051425, Dec. 9, 2010.
PCT International Preliminary Report on Patentability, PCT/US2010/051425, Apr. 19, 2012.
Ahn, et al., Myeloperoxidase Genotype, Fruit and Vegetable Consumption, and Breast Cancer Risk, Cancer Research, 2004, 64:7634-7639.
Ali, et al., Association of Serum Myeloperoxidase with the Ankle-Brachial Index and Peripheral Arterial Disease, Vascular Medicine, 2009, 14:215-220.
Arnhold, et al., Redox Properties of Myeloperoxidase, Redox Report, 2003, 8(5):179-186.
Baskol, et al., Investigation of Protein Oxidation and Lipid Peroxidation in Patients with Rheumatoid Arthritis, Cell Biochemistry and Function, 2006, 24(4):307-311.
Bekesi, et al., Effect of Inhibitors of Myeloperoxidase on the Development of Aortic Atherosclerosis in an Animal Model, Experimental Gerontology, 2005, 40(3):199-208.
Bergt, et al., The Myeloperoxidase Product Hypochlorous Acid Oxidizes HDL in the Human Artery Wall and Impairs ABCA1-Dependent Cholesterol Transport, PNAS, 2004, 101(35):13032-13037.

(Continued)

*Primary Examiner* — Jean Witz
*Assistant Examiner* — Mindy Newman
(74) *Attorney, Agent, or Firm* — Quarles & Brady LLP

(57) ABSTRACT

The present invention provides peptide-based peroxidase inhibitors having the formula $AA_1$-$AA_2$-$AA_3$, wherein $AA_1$ is a positively charged, negatively charged or neutral amino acid, $AA_2$ is a redox active amino acid, and $AA_3$ is an amino acid possessing a reducing potential such that $AA_3$ is capable of undergoing a redox reaction with a radical of amino acid $AA_2$ or a retro or retro-inverso analog thereof. The result of such a combination is a highly effective inhibitor of peroxidase activity that has potent anti-inflammatory properties in widely diverse models of vascular disease and injury. Exemplary tripeptides effectively inhibit peroxidase mediated LDL oxidation, increase vasodilation in SCD mice, inhibit eosinophil infiltration and collagen deposition in asthma mice, inhibit acute lung injury, and decrease ischemic injury of the heart.

35 Claims, 25 Drawing Sheets

(56) References Cited

OTHER PUBLICATIONS

Bhatt, Anti-Inflammatory Agents and Antioxidants as a Possible "Third Great Wave" in Cardiovascular Secondary Prevention, American Journal of Cardiology, 2008, 101[suppl]:4D-13D.

Brahmbhatt, et al., w-Oxidation of a-chlorinated Fatty Acids, Identification of a-Chlorinated Dicarboxylic Acids, Journal of Biological Chemistry, 2010, 285(53):41255-41269.

Braus, et al., FOCIS on FOCiS: Advances in the Pathogenesis and Treatment of IBD, Clin. Immunol., 2009, 132 (1):1-9.

Byun, et al., Nitrogen Dioxide Radical Generated by the Myeloperoxidase-Hydrogen Peroxide-Nitrite System Promotes Lipid Peroxidation of Low Density Lipoprotein, FEBS Letters, 1999, 455(3):243-246.

Carr, et al., Peroxidase-Mediated Bromination of Unsaturated Fatty Acids to Form Bromohydrins, Archives of Biochemistry and Biophysics, 1996, 327(2):227-233.

Carr, et al., Chlorination of Cholesterol in Cell Membranes by Hyopchlorous Acid, Archives of Biochemistry and Biophysics, 1996, 332(1):63-69.

Carr, et al., Modification of Red Cell Membrane Lipids by Hypochlorous Acid and Haemolysis by Preformed Lipid Chlorohydrins, Redox Report, 1997, 3:263-271.

Choi, et al., Ablation of the Inflammatory Enzyme Myeloperoxidase Mitigates Features of Parkinson's Disease in Mice, The Journal of Neuorscience, 2005, 25(28):6594-6600.

Chorev, et al., Recent Developments in Retro Peptides and Proteins—An Ongoing Topochemical Exploration, Trends in Biotechnology, 1995, 13(10):438-445.

Daugherty, et al., Myeloperoxidase, a Catalyst for Lipoprotein Oxidation, Is Expressed in Human Atherosclerotic Lesions, J. Clin. Invest., 1994, 94:437-444.

Dever, et al., Fatty Acid and Phospholipid Chlorohydrins Cause Cell Stress and Endothelial Adhesion, Acta Biochimica Polonica, 2006, 53(4):761-768.

Dever, et al., Phospholipid Chlorohydrin Induces Leukocyte Adhesion to ApoE Mouse Arteries Via Upregulation of P-Selectin, Free Radical Biology and Medicine, 2008, 44(3):452-463.

Droge, Free Radicals in the Physiological Control of Cell Function, Physiol. Rev., 2002, 82:47-95.

Dypbukt, et al., A Sensitive and Selective Assay for Chloramine Production by Myeloperoxidase, Free Radical Biology and Medicine, 2005, 39(11):1468-1477.

Ehses, et al., Macrophages, Cytokines and B-Cell Death in Type 2 Diabetes, Biochemical Society Transactions, 2008, 36:340-342.

Eiserich, et al., Formation of Nitric Oxide-Derived Inflammatory Oxidants by Myeloperoxidase in Neutrophils, Nature, 1998, 391:393-397.

Erdelmeier, et al., Reactions of N-Methyl-2-Phenylindole with Malondialdehyde and 4-Hydroxyalkenals, Mechanistic Aspects of the Colorimetric Assay of Lipid Peroxidation, Chemical Research in Toxicology, 1998, 11(10):1184-1194.

Fahy, Eosinophilic and Neutrophilic Inflammation in Asthma, Insights from Clinical Studies, Proc. Am. Thorac. Soc., 2009, 6:256-259.

Feksa, et al., Tryptophan Administration Induces Oxidative Stress in Brain Cortex of Rats, Metabolic Brain Disease, 2008, 23(2):221-233.

Ford D., Lipid Oxidation by Hypochlorous Acid: Chlorinated Lipids in Atherosclerosis and Myocardial Ischemia, Clin. Lipidol., 2010, 5(6):835-852.

Ford, E., et al., Kinetics of the Reactions of Nitrogen Dioxide with Glutathione, Cysteine, and Uric Acid at Physiological pH, Free Radical Biology and Medicine, 2002, 32(12):1314-1323.

Furtmuller, et al., Kinetics of Interconversion of Redox Intermediates of Lactoperoxidase, Eosinophil Peroxidase and Myeloperoxidase, Jpn. J. Infect. Dis., 2004, 57:S30-S31.

Furtmuller, et al., Active Site Structure and Catalytic Mechanisms of Human Peroxidases, Archives of Biochemistry and Biophysics, 2006, 445(2):199-213.

Galijasevic, et al., Melatonin is a Potent Inhibitor for Myeloperoxidase, Biochemistry, 2008, 47(8):2668-2677.

Galijasevic, et al., Potential Role of Tryptophan and Chloride in the Inhibition of Human Myeloperoxidase, Free Radic. Biol., Med., 2008, 44(8):1570-1577.

Gaston, et al., S-Nitrosothiol Signaling in Respiratory Biology, Am. J. Respir. Crit. Care Med., 2006, 173:1186-1193.

Gerard-Monnier, et al., Reactions of 1-Methyl-2-Phenylindole with Malondialdehyde and 4-Hydroxyalkenals. Analytical Applications to a Colorimetric Assay of Lipid Peroxidation, Chemical Research in Toxicology, 1998, 11 (10):1176-1183.

Gray, et al., Elevated Activity and Microglial Expression of Myeloperoxidase in Demyelinated Cerebral Cortex in Multiple Sclerosis, Brain Pathology, 2008, 18(1):86-95.

Gray, et al., Elevated Myeloperoxidase Activity in White Matter in Multiple Sclerosis, Neuroscience Letters, 2008, 444(2):195-198.

Green, et al., Neuronal Expression of Myeloperoxidase is Increased in Alzheimer's Disease, Journal of Neurochemistry, 2004, 90:724-733.

Gumina, et al., Antibody to Platelet/Endothelial Cell Adhesion Molecule-1 Reduces Myocardial Infarct Size in a Rat Model of Ischemia-Reperfusion Injury, Circulation, 1996, 94:3327-3333.

Hazen, et al., Formation of Nitric Oxide-Derived Oxidants by Myeloperoxidase in Monocytes, Pathways for Monocyte-Mediated Protein Nitration and Lipid Peroxidation In Vivo, Circ. Res., 1999, 85:950-958.

Hazen, et al., 3-Chlorotyrosine, a Specific Marker of Myeloperoxidase-Catalyzed Oxidation, is Markedly Elevated in Low Density Lipoprotein Isolated from Human Atherosclerotic Intima, Journal of Clinical Investigation, 1997, 99:2075-2081.

Heilman, et al., Arterial Stiffness, Carotid Artery Intima-Media Thickness and Plasma Myeloperoxidase Level in Children with Type 1 Diabetes, Diabetes Research and Clinical Practice, 2009, 84(2):168-173.

Heinecke, et al., Tyrosyl Radical Generated by Myeloperoxidase Catalyzes the Oxidative Cross-linking of Proteins, J. Clin. Invest., 1993, 91:2866-2872.

Heinecke, Tyrosyl Radical Production by Myeloperoxidase: A Phagocyte Pathway for Lipid Peroxidation and Dityrosine Cross-Linking of Proteins, Toxicology, 2002, 177(1):11-22.

Hermann, et al., Salicylate Promotes Myeloperoxidase-Initiated LDL Oxidation: Antagonization by its Metabolite Gentisic Acid, Free Radical Biology and Medicine, 1999, 26(9-10):1253-1260.

Hori, et al., Aromatic Substrate Molecules Bind at the Distal Heme Pocket of Myeloperoxidase, Journal of Biological Chemistry, 1994, 269(11):8388-8392.

Houghton, The Paradox of Tumor-Associated Neutrophils, Fueling Tumor Growth with Cytotoxic Substances, Cell Cycle, 2010, 9(9):1732-1737.

Hoy, et al., Growing Significance of Myeloperoxidase in Non-Infectious Diseases, Clinical Chemistry and Laboratory Medicine, 2002, 40(1):2-8.

Jerlich, et al., Comparison of HOCl Traps with Myeloperoxidase Inhibitors in Prevention of Low Density Lipoprotein Oxidation, Biochimica et Biophysica Acta, 2000, 1481:109-118.

Kato, et al., Inhibition of Myeloperoxidase-Catalyzed Tyrosylation by Phenolic Antioxidants In Vitro, Biosci. Biotechnol. Biochem., 2003, 67(5):1136-1139.

Kemp, et al., Non-Equilibrium Thermodynamics of Thiol/Disulfide Redox Systems: A Perspective on Redox Systems Biology, Free Radic. Biol. Med., 2008, 44(6):921-937.

Kettle, et al., Mechanism of Inhibition of Myeloperoxidase by Anti-Inflammatory Drugs, Biochemical Pharmacology, 1991, 41(10):1485-1492.

Kettle, et al., Oxidation of Tryptophan by Redox Intermediates of Myeloperoxidase and Inhibition of Hypochlorous Acid Production, Redox Report, 2000, 5(4):179-184.

Klebanoff, Myeloperoxidase: Friend and Foe, Journal of Leukocyte Biology, 2005, 77:598-625.

Koelsch, et al., Acetaminophen (Paracetamol) Inhibits Myeloperoxidase-Catalyzed Oxidant Production and Biological Damage at Therapeutically Achievable Concentrations, Biochemical Pharmacology, 2010, 79(8):1156-1164.

(56) References Cited

OTHER PUBLICATIONS

Lau, et al., Myeloperoxidase and its Contributory Role in Inflammatory Vascular Disease, Pharmacology & Therapeutics, 2006, 111(1):16-26.
Lefkowitz, et al., Microglia and Myeloperoxidase: A Deadly Partnership in Neurodegenerative Disease, Free Radical Biology and Medicine, 2008, 45(5):726-731.
Loria, et al., Myeloperoxidase: A New Biomarker of Inflammation in Ischemic Heart Disease and Acute Coronary Syndromes, Mediators of Inflammation, vol. 2008, Article ID 135625, 4 pages.
Maki, et al., Aberrant Expression of Myeloperoxidase in Astrocytes Promotes Phospholipid Oxidation and Memory Deficits in a Mouse Model of Alzheimer Disease, Journal of Biological Chemistry, 2009, 284(5):3158-3169.
Malle, et al., Myeloperoxidase in Kidney Disease, Kidney International, 2003, 64:1956-1967.
Malle, et al., Myeloperoxidase-Mediated Oxidation of High-Density Lipoproteins: Fingerprints of Newly Recognized Potential Proatherogenic Lipoproteins, Archives of Biochemistry and Biophysics, 2006, 445(2):245-255.
Malle, et al., Myeloperoxidase: A Target for New Drug Development?, British Journal of Pharmacology, 2007, 152:838-854.
Messner, et al., Selective Plasmenylcholine Oxidation by Hypochlorous Acid: Formation of Lysophosphatidylcholine Chlorohydrins, Chemistry and Physics of Lipids, 2006, 144(1):34-44.
Messner, et al., 2-Chlorohexadecanal and 2-Chlorohexadecanoic Acid Induce COX-2 Expression in Human Coronary Artery Endothelial Cells, Lipids, 2008, 43(7):581-588.
Nagra, et al., Immunohistochemical and Genetic Evidence of Myeloperoxidase Involvement in Multiple Sclerosis, Journal of Neuroimmunology, 1997, 78(1):97-107.
Naito, et al., Molecular Fingerprints of Neutrophil-Dependent Oxidative Stress in Inflammatory Bowel Disease, Journal of Gastroenterology, 2007, 42(10):787-798.
Nicholls, et al., Formation of Dysfunctional High-Density Lipoprotein by Myeloperoxidase, Trends in Cardiovascular Medicine, 2005, 15(6):212-219.
Nicholls, et al., Myeloperoxidase and Cardiovascular Disease, Arterioscler. Thromb. Vasc. Biol., 2005, 25:1102-1111.
Nielsen, et al., Serum Eosinophil Granule Proteins Predict Asthma Risk in Allergic Rhinitis, Allergy, 2009, 64:733-737.
Nurcombe, et al., Activation of the Neutrophil Myeloperoxidase-H2O2 System by Synovial Fluid Isolated From Patients with Rheumatoid Arthritis, Annals of the Rheumatic Diseases, 1991, 50:237-242.
Ostrand-Rosenberg, et al., Myeloid-Derived Suppressor Cells: Linking Inflammation and Cancer, The Journal of Immunology, 2009, 182:4499-4506.
Ou et al., L-4F, An Apolipoprotein A-1 Mimetic, Dramatically Improves Vasodilation in Hypercholesterolemia and Sickle Cell Disease, Circulation, 2003, 107:2337-2341.
Ou et al., L-4F, An Apolipoprotein A-1 Mimetic, Restores Nitric Oxide and Superoxide Anion Balance in Low-Density Lipoprotein-Treated Endothelial Cells, Circulation, 2003, 107:1520-1524.
Panasenko, et al., Myeloperoxidase-Induced Formation of Chlorohydrins and Lysophospholipids from Unsaturated Phosphatidylcholines, Free Radical Biology and Medicine, 2003, 34(5):553-562.
Panzenboeck, et al., Effects of Reagent and Enzymatically Generated Hypochlorite on Physicochemical and Metabolic Properties of High Density Lipoproteins, Journal of Biological Chemistry, 1997, 272(47):29711-29720.
Pattison, et al., Kinetic Analysis of the Reactions of Hypobromous Acid with Protein Components: Implications for Cellular Damage and Use of 3-Bromotyrosine as a Marker of Oxidative Stress, Biochemistry, 2004, 43(16):4799-4809.
Pattison, et al., Absolute Rate Constants for the Reaction of Hypochlorous Acid with Protein Side Chains and Peptide Bonds, Chemical Research in Toxicology, 2001, 14(10):1453-1464.
Pattison, et al., Reactions of Myeloperoxidase-Derived Oxidants with Biological Substrates: Gaining Chemical Insight into Human Inflammatory Diseases, Current Medicinal Chemistry, 2006, 13(27):3271-3290.
Peskin, et al., Kinetics of the Reactions of Hypochlorous Acid and Amino Acid Chloramines with Thiols, Methionine, and Ascorbate, Free Radical Biology & Medicine, 2001, 30(5):572-579.
Prutz, et al., Direct Demonstration of Electron Transfer Between Tryptophan and Tyrosine in Proteins, Biochemical and Biophysical Research Communications, 1980, 96(1):408-414.
Prutz, et al., The Role of Sulphur Peptide Functions in Free Radical Transfer: A Pulse Radiolysis Study, International Journal of Radiation Biology, 1989, 55(4):539-556.
Pullar, et al., Loss of GSH and Thiol Enzymes in Endothelial Cells Exposed to Sublethal Concentrations of Hypochlorous Acid, Am. J. Physiol. (Heart Circ. Physiol. 46), 1999, 277:H1505-H1512.
Rezzani, et al., Effects of Melatonin and Pycnogenol on Small Artery Structure and Function in Spontaneously Hypertensive Rats, Hypertension, 2010, 55:1373-1380.
Salavej, et al., Modification of Amino Acid Residues in Human Serum Albumin by Myeloperoxidase, Free Radical Biology and Medicine, 2006, 40(3):516-525.
Savenkova, et al., Tyrosyl Radical Generated by Myeloperoxidase is a Physiological Catalyst for the Initiation of Lipid Peroxidation in Low Density Lipoprotein, The Journal of Biological Chemistry, 1994, 269(32):20394-20400.
Schiller, et al., NMR Studies on Human, Pathologically Changed Synovial Fluids: Role of Hypochlorous Acid, Magnetic Resonance in Medicine, 1996, 35(6):848-853.
Skaff, et al., Kinetics of Hypobromous Acid-Mediated Oxidation of Lipid Components and Antioxidants, Chemical Research in Toxicology, 2007, 20(12):1980-1988.
Stadtman, Protein Oxidation and Aging, Free Radical Research, 2006, 40(12):1250-1258.
Steffen, et al., Cytotoxicity of Myeloperoxidase/Nitrite-Oxidized Low-Density Lipoprotein Toward Endothelial Cells is Due to a High 7B-Hydroxycholesterol to 7-Ketocholesterol Ratio, Free Radical Biology and Medicine, 2006, 41 (7):1139-1150.
Taioli, et al., Myeloperoxidase G-463A Polymorphism and Lung Cancer: A Huge Genetic Susceptibility to Environmental Carcinogens Pooled Analysis, Genet. Med., 2007, 9(2):67-73.
Tanner, et al., Intramolecular Electron Transfer in the Dipeptide, Histidyltyrosine: A Pulse Radiolysis Study, Free Radical Biology and Medicine, 1998, 24(4):671-678.
Tien, Myeloperoxidase-Catalyzed Oxidation of Tyrosine, Archives of Biochemistry and Biophysics, 1999, 367(1):61-66.
Tomono, et al., Formation of Cholesterol Ozonolysis Products Through an Ozone-Free Mechanism Mediated by the Myeloperoxidase-H2O2-Chloride System, Biochemical and Biophysical Research Communications, 2009, 383 (2):222-227.
Van Der Vliet, et al., Myeloperoxidase and Protein Oxidation in Cystic Fibrosis, Am. J. Physiol. Lung Cell Mol. Physiol., 2000, 279:L537-L546.
Weiner, et al., Inflammation and Therapeutic Vaccination in CNS Diseases, Nature, 2002, 420:879-884.
Wiersma, et al., Diabetes Mellitus Type 2 is Associated with Higher Levels of Myeloperoxidase, Med. Sci. Monit., 2008, 14(8):CR406-410.
Winterbourn, et al., Myeloperoxidase, Current Opinion in Hematology, 2000, 7(1):53-58.
Wu, et al., Chlorinated and Brominated Phosphatidylcholines are Generated Under the Influence of the Fenton Reagent at Low pH—a MALDI-TOF MS Study, Chemistry and Physics of Lipids, 2011, 164(1):1-8.
Ximenes, et al., Serotonin as a Physiological Substrate for Myeloperoxidase and Its Superoxide-Dependent Oxidation to Cytotoxic Tryptamine-4,5-dione, Biochem. J., 2010, 425:285-293.
Ximenes, et al., Oxidation of Melatonin by AAPH-Derived Peroxyl Radicals: Evidence of a Pro-Oxidant Effect of Melatonin, Biochimica et Biophysica Acta, 2009, 1790(8):787-792.
Yamakura, et al., Nitrated and Oxidized Products of a Single Tryptophan Residue in Human Cu,Zn-Superoxide Dismutase

(56) References Cited

OTHER PUBLICATIONS

Treated With Either Peroxynitrite-Carbon Dioxide or Myeloperoxidase-Hydrogen Peroxide-Nitrite, Journal of Biochemistry, 2005, 138(1):57-69.

Yunoki, et al., Relation of Elevated Levels of Plasma Myeloperoxidase to Impaired Myocardial Microcirculation After Reperfusion in Patients with Acute Myocardial Infarction, American Journal of Cardiology, 2010, 105(7):922-929.

* cited by examiner

Sensitization and Treatment Protocol

Ischemia Protocol

| | 30MIN | 40MIN | 50MIN | 120MIN |
|---|---|---|---|---|
| CON | BASELINE | | ISCHEMIA | REPERFUSION |
| KWC | BASELINE | KWC 50mg/L | ISCHEMIA | REPERFUSION |
| KAA | BASELINE | KAA 50mg/L | ISCHEMIA | REPERFUSION |

PEPTIDE-BASED PEROXIDASE INHIBITORS AND METHODS OF USING SAME

CROSS-REFERENCE TO RELATED APPLICATIONS

This application is a continuation-in-part of U.S. application Ser. No. 13/500,040, filed Apr. 3, 2012, which is the U.S. National Phase entry of PCT International Application No. PCT/US2010/051425, filed Oct. 5, 2010, which claims the benefit of U.S. Appn. No. 61/248,627, filed Oct. 5, 2009, all of which are hereby incorporated by reference herein for all purposes.

STATEMENT REGARDING FEDERALLY SPONSORED RESEARCH OR DEVELOPMENT

This invention was made with government support under HL102996-01A1 and HL102836 awarded by the National Institutes of Health—National Heart Lung Blood Institute and 11SDG5120015 awarded by the American Heart Association. The government has certain rights in the invention.

BACKGROUND OF THE INVENTION

It is well established that inflammation plays an important role in pathogenesis of disease. Inflammation has been shown to be involved in the mechanisms driving neurodegenerative disease, cardiovascular disease, airway disease, inflammatory bowel disease (IBD), diabetes and even cancer. One of the major factors promoting cellular injury during inflammation is oxidative stress. Oxidative stress is induced in cells by over production of reactive oxygen species (ROS), reactive nitrogen species (RNS) and/or an increase in heme peroxidase activity. During inflammation, cells produce highly reactive free radicals (e.g., superoxide anion, hydroxyl radical, peroxide radical, and nitrogen dioxide radical) and strong oxidants (e.g., peroxynitrite and hydrogen peroxide). These free radicals and oxidants have been shown to oxidatively modify proteins, nucleic acids and lipids to the point of causing cell injury and death.

Growing evidence supports the idea that over-expression or increased activity of mammalian heme peroxidases are involved in the pathogenesis and progression of a variety of diseases. For example, increased neutrophil-derived myeloperoxidase (MPO) activity has been found in atherosclerosis, Alzheimer's disease, Parkinson's disease, multiple sclerosis, IBD, kidney disease and rheumatoid arthritis. Another immune cell derived peroxidase, eosinophil peroxidase (EPO), also causes severe respiratory damage in asthma. The relationship between peroxidase and cardiovascular disease is so strong that a measured increase in heme peroxidase (MPO) has been used as a biomarker for the diagnosis and prognosis of cardiovascular disease. In spite of the recent growth in the evidence that heme peroxidases play important roles in the pathogenesis of vascular disease, effective therapies targeting aberrant heme peroxidase activity remain lacking.

Mammalian heme peroxidases, including MPO, are activated by hydrogen peroxide ($H_2O_2$). Activated peroxidases catalyze oxidation reactions with a variety of compounds through either a one-electron oxidation cycle or two-electron oxidation cycle. The mechanisms mediating peroxidase activation are as follows. In the inactive native state, the Fe ion in the active site of mammalian heme peroxidases is in the $Fe^{3+}$ state. This ferrous ion reacts with $H_2O_2$ to form compound I, an oxy-ferryl-cation radical ($PFe^{4+}=O$). Compound I reacts with halides ($Cl^{-1}$ and $Br^{-1}$) or pseudohalides ($SCN^{-1}$) via direct, two-electron reduction to form hypochlorous acid (HOCl), hypobromous acid (HOBr), and hypothiocynite (HOSCN), respectively. As these potent oxidants leave the active site, the heme peroxidases are reduced back to $Fe^{3+}$ and the cycle starts over again with the arrival of a second $H_2O_2$.

Compound I can also react with organic and inorganic substrates such as aromatic amino acids, derivatives of indole and a variety of other species (i.e., nitrite, ascorbate and urate) via two, sequential one-electron reductions. In this reaction sequence, nitrite or tyrosine reduces Compound I to form compound II ($Fe^{4+}=O$), which yields a nitrogen dioxide radical or a tyrosyl radical, respectively. Compound II can be further reduced by one electron back to the $Fe^{3+}$ state by a second nitrite or tyrosine.

It is important to note that heme peroxidases can generate both oxidants and free radicals through direct oxidation of biological molecules. This makes them one of the most potent sources of oxidative stress. It has been shown that heme peroxidase-derived oxidants and free radicals oxidatively modify proteins to chlorotyrosine, bromotyrosine, nitrotyrosine, dityrosine, thiol oxidation products and haloamine, DNA molecules to 5-chlorouracil, and lipids to halohydrins, lysophospholipids, α-halo-fatty aldehydes, and other lipid peroxidation products.

As peroxidase-generated oxidants and radicals induce cell injury and death, inhibition of such chronic increases in aberrant peroxidase activity should, in turn, decrease chronic inflammation. Several research programs have worked on developing inhibitors for heme peroxidases over the last several decades. For the most part this research has focused on three lines of investigation. The first line of research focuses on hydrazine ($RNHNH_2$) and hydrazide ($RCONHNH_2$) derivatives that irreversibly inhibit heme peroxidase activity. However, these compounds are considered "suicide substrates" of peroxidase and inactivate the enzyme by destroying the heme center. The second line of research focuses on hydroxamic acids [RCNOHOH or RC(O)NHOH] and indole type compounds that reversibly inhibit peroxidase activity. Hydroxamic acids reduce Compound I and II. They also inhibit $H_2O_2$ binding to the heme peroxidase to inhibit formation of Compound I. Some of the indole derivatives (such as tryptophan, tryptamine and melatonin) also rapidly reduce compound I and inhibit the two-electron oxidation cycle of peroxidase. The final line of investigation focuses on another class of compounds that inhibit peroxidase via scavenging heme peroxidase oxidation products, for example, vitamin E and polyphenols scavenge nitrogen dioxide radicals.

Although MPO plays an important role in fighting infection, it is also believed to play a causal role in the development of atherosclerosis. Several clinical studies show that plasma MPO concentrations directly correlate with increased risk of arteriosclerosis, acute myocardial infarction and even heart failure. Immunofluorescent studies show that sickle cell disease (SCD) increases MPO deposition in the subendothelial spaces in the lungs of patients who have died from complications of SCD. The fact that MPO was observed to co-localize with 3-nitrotyrosine in these studies means that when MPO is released and trapped in the vessel wall, it remains fully capable of generating potent oxidants (i.e., .$NO_2$) to nitrate protein tyrosines.

Unfortunately, the progress made in understanding the mechanisms by which MPO impairs vascular function, has not translated into the development of effective therapies. Even though aggressive efforts have been taken, the agents or drugs that have been developed to date fall short for several reasons. Several strategies have been employed. For example, azide, hydrazides and hydroxamic acids have been used to irreversibly inhibit MPO by modifying the heme site. Indole derivatives have been used because they effectively compete with Cl⁻, SCN⁻ to prevent Compound I from generating HOCl and HOSCN. Phenolic compounds have been used because they effectively scavenge compound I and II.

However, all of these agents have side effects that limit their use to in vitro or cell culture studies. None have been used successfully to reduce oxidative stress in vivo. It is unclear if the intrinsic toxic nature of the compounds (such as hydrazine or hydrazide) or the toxicity of products generated after oxidation by peroxidase makes the compounds essentially worthless as therapeutic agents. In the instances where the agents have been used in animal models, they were observed to be either directly toxic or were converted into toxic compounds. For instance, heme poisons have been shown to inhibit mitochondrial respiration, which is not be a good thing. Even though indole derivatives are effective for scavenging Compound I, MPO oxidizes them to an indole radical that is both toxic and capable of increasing oxidative stress. Finally, even though phenolic agents effectively scavenge Compound I, MPO oxidizes them to phenoxyl radicals that are highly toxic and capable of increasing oxidative stress via oxidative modification of proteins and lipids. Such outcomes underscore the importance of developing specific MPO inhibitors that can be used not only for treating vascular disease but also investigating mechanisms by which MPO increases vascular disease.

Accordingly, there is a long felt but unsolved need in this field to obtain improved agents that effectively prevent or reduce peroxidase-dependent oxidative stress in the in vivo setting.

BRIEF SUMMARY OF THE INVENTION

To overcome the drawbacks associated with the previous approaches, the present inventors have developed a series of peptide-based heme peroxidase inhibitors, in which redox active amino acids such as tyrosine and tryptophan serve as agents that reduce both compound I and II. While no one theory or mechanism of pharmacological effect is adopted herein, it appears that the small peptides are acted on by the peroxidase to form a tryptophanyl and tyrosyl radical that is rapidly scavenged by the thiol of an adjacent cysteine. This reaction yields a thiol radical or a mixed disulfide that can be further detoxified in vivo by thiol reduction systems (such as GSH/GSSG, GSH reductase, glutaredoxin or thioredoxin). The inventors observed that tripeptides containing Try/Trp, Cys, and a positive amino acid such as lysine are able to serve as potent inhibitors of peroxidase activity. The inventors have demonstrated that these small peptides not only inhibit MPO-mediated LDL oxidation in vitro but also are highly effective at improving vascular function, decreasing pulmonary inflammation and increasing cardioprotection.

Accordingly, in a first aspect, the invention is a peptide-based peroxidase inhibitor having the formula $AA_1$-$AA_2$-$AA_3$, wherein $AA_1$ is a positively charged, negatively charged or neutral amino acid, $AA_2$ is a redox active amino acid, and $AA_3$ is an amino acid possessing a reducing potential such that $AA_3$ is capable of undergoing a redox reaction with a radical of amino acid $AA_2$. Such peptide inhibitors are particularly useful for improving vascular function, decreasing pulmonary inflammation and increasing cardioprotection in a subject. In certain preferred embodiments, the peptide inhibitor has the amino acid sequence KYC or KWC. The invention also encompasses protected peptide versions as well as retro or retro-inverso analogs. Accordingly, in certain embodiments, some of the amino acids comprising the required amino acid sequence are "D" amino acids; in other embodiments, all the amino acids comprising the required amino acid sequence are "D" amino acids.

In certain embodiments, the peptide contains both an acetyl protecting group coupled to the peptide's amino terminus and an amide protecting group coupled to the peptide's carboxyl terminus. Preferred inhibitors according to the invention include the protected tripeptides Ac-KYC-amide and Ac-KWC-amide.

The invention also includes pharmaceutical compositions useful as peroxidase inhibitors. Such compositions contain one or more of the peptides described herein and a pharmaceutically acceptable carrier.

In another aspect, the invention provides a method of inhibiting peroxidase activity in a subject. The method includes the step of administering to a subject in need of such therapy one or more of the peptides described herein. In certain preferred embodiments, the subject is a human or a non-human mammal. Preferably, the method includes the additional step of mixing the peptide with a pharmaceutically acceptable carrier before the peptide is administered. In preferred embodiments of the invention, the method is carried out to improve vascular function, decrease pulmonary inflammation, and/or increase cardioprotection in the subject.

Of course, the invention also contemplates the use of a peptide as described and claimed herein for the manufacture of a medicament for inhibiting peroxidase activity in a subject. Such methods include the steps of (a) providing a peptide as described herein, and (b) mixing the peptide with a pharmaceutically acceptable carrier. As well, the invention encompasses the manufacture and use of medicaments specifically-purposed for treatment of one or more of the diseases/conditions described in the following disclosure.

The invention further provides a method of inhibiting peroxidase activity in a subject comprising administering to the subject a peptide-based peroxidase inhibitor consisting of (a) the tripeptide KYC, or (b) the tripeptide KYC having a protecting group coupled to its amino terminus, its carboxyl terminus, or to both its amino and carboxyl termini. In one embodiment, all the amino acids in the peptide-based peroxidase inhibitor are L-amino acids, while in alternate embodiments, an acetyl protecting group is coupled to the amino terminus of the tripeptide, and an amide protecting group is coupled to the carboxyl terminus of the tripeptide. The method results in the prevention or treatment of a disease or condition attributable to aberrant peroxidase activity in the subject, wherein the disease or condition attributable to aberrant peroxidase activity is a vascular disease or lung cancer. In one embodiment, the vascular disease is atherosclerosis and in other embodiments lung cancer is effectively treated or prevented.

Other objects, advantages and features of the present invention will become apparent from the following specification taken in conjunction with the accompanying drawings.

BRIEF DESCRIPTION OF THE DRAWINGS

FIG. 1 depicts the scheme for OVA sensitization of mice described in the examples section.

FIG. 14A. The effect of different tripeptides on the MPO-mediated HOCl formations.

FIG. 14-B-14D. All tripeptide concentrations are at 12.5 μM. The dose dependent inhibition of MPO catalyzed HOCl formation by KYC (FIG. 14B), KYS (FIG. 14C) and KFC (FIG. 14D). KYC inhibited HOCl formation at an $IC_{50}$ of ~7 μM.

FIG. 14E. Comparison of the effects of equimolar concentrations (12.5 μM) of KYC isomers on MPO-catalyzed HOCl formation.

FIG. 14F. Comparison of the effect of equimolar concentrations (12.5 μM) of KYC with Tyr, and Trp on MPO catalyzed HOCl formation. All Data (mean±SD, n=3) are expressed as % of control (without tripeptide in reactions) (**p<0.01).

FIG. 15A. HPLC analysis of KYC products from various MPO-mediated oxidation reactions detected at 280 nm. FIG. 15A, trace a. KYC (440 μM) was incubated with $H_2O_2$ (100 μM) in phosphate buffer (100 mM, pH 7.4) containing DTPA (100 μM) at room temperature for 30 min and the reaction products analyzed by HPLC. FIG. 15A, Trace b. Reaction conditions and incubation times same as in FIG. 15A, Trace a but with MPO included (50 nM). FIG. 15A, Trace c. Reaction conditions and incubation times same as in FIG. 15A, Trace b but with $NaNO_2$ (0.5 mM) included. FIG. 15A, Trace d. Reaction conditions and incubation times same as in FIG.

15A, Trace b but with NaCl (100 mM) included. FIG. 15, Trace e. HPLC trace of KYC disulfide standard.

FIG. 15B. HPLC analysis of KYC products from MPO/$H_2O_2$-mediated oxidation detected by fluorescent detection at excitation=290 nm and emission=410 nm. FIG. 15B, Trace a. KYC/$H_2O_2$ and FIG. 15B, Trace b. MPO/KYC/$H_2O_2$.

FIG. 15C. HPLC analysis of KYS products from MPO/$H_2O_2$-mediated oxidation reactions detected at 280 nm. FIG. 15C, Trace a. KYS/$H_2O_2$ and FIG. 15C, Trace b. MPO/KYS/$H_2O_2$.

FIG. 15D. HPLC analysis of KYS products from MPO/$H_2O_2$-mediated oxidation reactions detected by fluorescent detection at excitation=290 nm and emission=410 nm. FIG. 15D, Trace a. KYS/$H_2O_2$ and FIG. 15D, Trace b. MPO/KYS/$H_2O_2$.

FIG. 15E. HPLC analysis of KFC products from MPO/$H_2O_2$-mediated oxidation reactions detected at 220 nm. FIG. 15E, Trace a. KFC/$H_2O_2$ and FIG. 15E, Trace b. MPO/KFC/$H_2O_2$.

FIG. 15F. HPLC analysis of KFC products from MPO/$H_2O_2$-mediated oxidation reactions detected by fluorescent detection at excitation=290 nm and emission=410 nm. FIG. 15F, Trace a. KFC/$H_2O_2$ and FIG. 15F, Trace b. MPO/KFC/$H_2O_2$.

FIG. 17A shows that KYC dose dependently inhibits HL-60 cell HOCl production.

FIG. 20A. KYC dose-dependently inhibits LDL lipid oxidation induced by MPO/$H_2O_2$/NaNO₂. Line graphs showing time- and concentration-dependent oxidation of LDL. KYC decreases MPO-mediated oxidation as measured by absorbance of conjugated dienes at 234 nm.

FIG. 20B. Effects of 25 μM KYC, KYS and KFC on MPO/$H_2O_2$/NaNO₂-mediated LDL conjugated dienes formation.

FIG. 20C. Effects of KYC, GSH, Tyr and Trp (25 μM) on MPO/$H_2O_2$/NaNO₂-mediated LDL conjugated dienes formation.

FIG. 20D. Effects of KYC, GSH, Tyr and Trp ((25 μM) on MPO/$H_2O_2$-induced LDL conjugated dienes formation. Incubation conditions were the same as above in FIG. 20B except without NaNO₂ as described elow.

FIG. 20E. MPO-mediated LDL Malondialdehyde (MDA) Formation determined by N-methyl-2-phenylindole assay at 586 nm. The data represent 3 repeats.

FIG. 22A. Inhibition of LDL Trp oxidation by KYC. LDL (0.15 mg/mL), NaNO₂ (100 μM), $H_2O_2$ (100 μM), MPO (20 nM) and increasing concentrations of KYC in a phosphate buffer (100 mM, pH 7.4) containing DTPA (100 μM) was incubated at room temperature for 30 min. The oxidation of tryptophan in LDL was determined by measuring the changes of tryptophan fluorescence (Ex=294 nm/Em=345 nm).

DETAILED DESCRIPTION OF THE INVENTION

Figure 2:
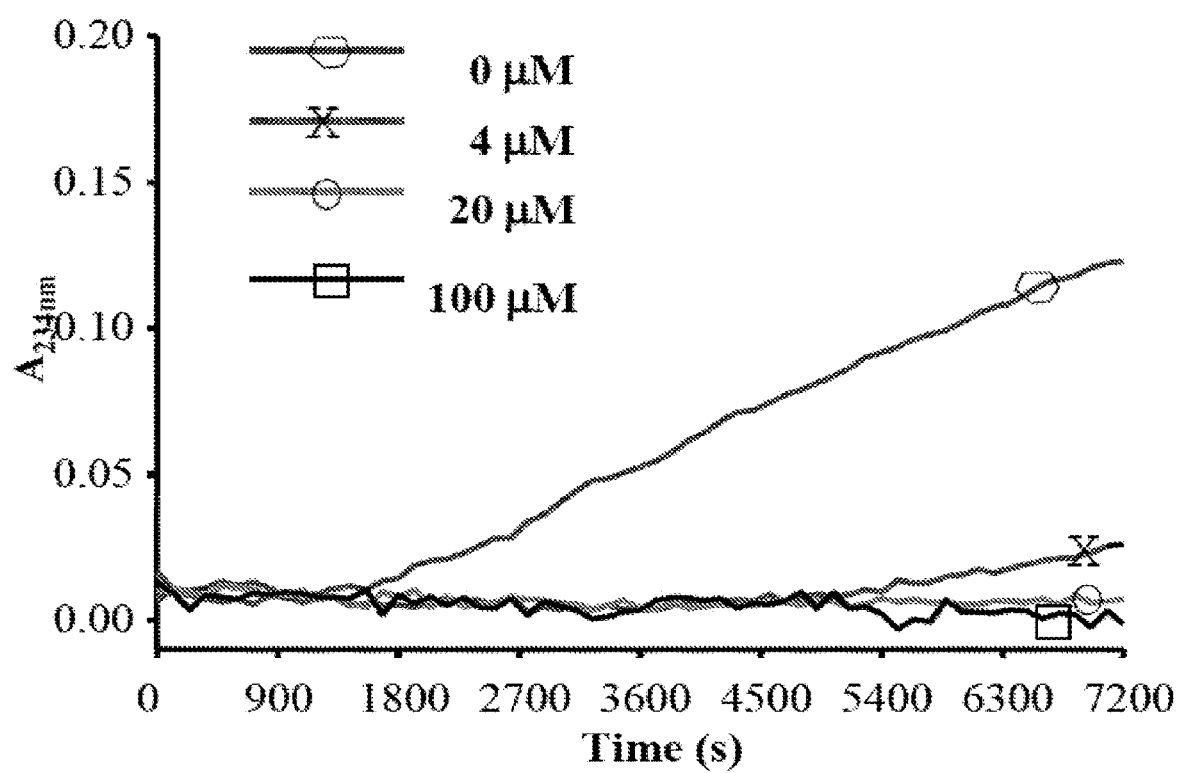
FIG. 2 shows that Ac-KYC-amide inhibits MPO-mediated oxidation of LDL. Reaction mixture contains LDL (0.15 mg/ml), $NaNO_2$ (100 µM), $H_2O_2$ (300 µM), MPO (20 nM) and various amount of HZ2 (Ac-KYC) in a potassium phosphate buffer (100 mM, pH 7.4) containing DTPA (100 µM). The oxidation of LDL was followed at 234 nm by a HP UV/VIS spectrometer at room temperature. The traces in the figure represented 2 repeat experiments.

I. In General.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used and all cited references are incorporated herein by reference for all purposes.

As used herein, the term "amino acid" residue or sequence refers to abbreviations used herein for designating the amino acids based on recommendations of the IUPAC-IUB Commission on Biochemical Nomenclature (see Biochemistry (1972) 11:1726-1732). Also included are the (D) and (L) stereoisomers of such amino acids when the structure of the amino acid admits of stereoisomeric forms. The term "amino acid" encompasses the 20 naturally-occurring amino acids and, as well, the "unnatural amino acids" which include any amino acid, modified amino acid, and/or amino acid analog that is not one of the 20 common naturally occurring amino acids.

As used herein, the phrase "redox active amino acid" refers to an amino acid which comprises a moiety that allows electron and/or proton transferring in and out of the amino acid.

As used herein, the term "amino acid possessing a reducing potential" refers to an amino acid having the ability to participate in a redox reaction, particularly a redox reaction with the radical of a redox active amino acid contained in the same peptide as the amino acid possessing the reducing potential.

As used herein, the term "peptide" refers to a polymer of amino acid residues. The terms apply to amino acid polymers in which one or more amino acid residues is an artificial chemical analogue of a corresponding naturally occurring amino acid, as well as to naturally occurring amino acid polymers. For example, "peptide" specifically includes the non-genetically-coded amino acids that either occur naturally or are chemically synthesized including, but not limited to synthetic α- and β-amino acids known to one of skill in the art.

As used herein, the term "analog" refers to a molecule in which one or more atoms, functional groups, or substructures have been replaced with different atoms, groups, or substructures. Analogs of the inhibitors described herein are generally "functional analogs" in that they share similar physical, chemical, biochemical, or pharmacological properties to the described molecules.

As used herein, the phrase "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propenol, formyl and others. Preferred carboxyl terminal protecting groups include, but are not limited to groups that form amides or esters.

As used herein, the term "retro" as applied to an amino acid sequence refers to an amino acid sequence that is in reverse order of the original reference sequence. The term "inverso" as applied to an amino acid sequence refers to an amino acid sequence composed of D-amino acids as opposed to the parent L-sequence. Because the orientation of the side-chains in a retro-inverso analog is very similar to that in a reference L-sequence, there is a high probability of functional similarity between the two sequences.

As used herein, the phrase "inhibiting peroxidase activity" refers to a statistically significant reduction in peroxidase activity measured in either in vitro or in vivo settings. Various methods to assay peroxidase inhibition are known in the field, including the $MPO/H_2O_2$-mediated LDL oxidation assay described in the examples section below.

As used herein, the term "subject" includes non-human mammals and humans.

As used herein, the phrase "therapeutically effective amount" means the amount of a compound that, when administered to a subject for treating a disease or disorder, is sufficient to affect such treatment for the disease or disorder. The "therapeutically effective amount" can vary depending on the compound, the disease or disorder and its severity, and the age, weight, etc., of the subject to be treated.

As used herein, the term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

II. The Invention.

During chronic states of inflammation such as diabetes, atherosclerosis, hypertension, SCD and asthma, white blood cells become activated and release a variety of peroxidases. As all cells generate $H_2O_2$, this released peroxidase creates an environment where secondary free radicals are produced on an ongoing basis. Under these conditions, cells adjacent to the peroxidase are subjected to chronic increases in oxidative stress and inflammation.

Several different strategies have been used in the design of heme peroxidase inhibitors. Different approaches used to date rely on 1) irreversible modification of the heme center of the active site; 2) reversible binding of a substrate inhibitor which blocks $H_2O_2$ binding to compound I and II; and 3) scavenging of the toxic radical products released from heme peorxidase after oxidation.(19) Although some of these compounds inhibit heme peroxidase activity in vitro, none of the inhibitors proposed to date are suitable for inhibiting peroxidase in vivo because they are directly toxic or the oxidized products generated via peroxidase are toxic. As research continues to link aberrant peroxidase activity to chronic disease, developing novel non-toxic inhibitors of heme peroxidase becomes an urgent task for providing effective therapies.

Redox active amino acids such as Tyr and Trp have been shown to be susceptible to oxidation induced by heme peroxidases. Indole related compounds have been proposed as myeloperoxidase inhibitors for inhibiting the formation of hypochlorous acid.(28, 29) However, the Tyr and Trp radicals generated are also pro-oxidants that can cause cell injury and death.(19, 30) Others have shown that tyrosyl radicals can induce LDL oxidation via transferring the radical from tyrosine to unsaturated fatty acids.(19) Therefore, Tyr and Trp alone cannot act as an effective peroxidase inhibitors for reducing peroxidase mediated cell injury.

In order to treat peroxidase-dependent oxidative stress in the in vivo setting, the inventors designed a series of small peptides where the central amino acid was a tryptophan (W) or tyrosine (Y) bracketed by an adjacent lysine (K) and cysteine (C). The tripeptides were used to treat diverse murine models of inflammation and vascular disease, where aberrant peroxidase activity is believed to be involved. In vitro, the tripeptide Ac-KYC-amide (KYC) significantly inhibited myeloperoxidase-mediated low-density lipoprotein (LDL) oxidation. KYC treatment of sickle cell disease mice markedly increased vasodilatation of isolated facialis arteries in response to acetylcholine (ACh) compared with non-responsive isolated arteries from untreated SCD mice. KYC treatments decreased pulmonary inflammation and eosinophil infiltration in vivo in a murine model of asthma (via ovalbumin sensitization). Finally, Ac-KWC-amide (KWC), increased cardioprotection of isolated perfused rat hearts that were subjected to ischemia/reperfusion (I/R) injury. Together these data demonstrate that small peptides containing a central amino acid that is a redox active aromatic amino acid (e.g., tyrosine, tryptophan) directly adjacent to an electron donor (e.g., cysteine) and a third amino acid with positive charge are potent inhibitors of heme peroxidases. This configuration seems to represent the minimal construct required for inhibiting peroxidase activity. The inventors' observations demonstrate that KWC and KYC are highly effective for treating vascular disease, pulmonary inflammation and any other form of peroxidase-mediated injury.

In this invention, the inventors unexpectedly showed that structurally novel peptides can be used to detoxify MPO activity. By placing an aromatic amino acid between a cysteine and lysine (or other amino acid) to generate the structurally novel peptides of the present invention, peptides are formed that are easily oxidized to form an aromatic amino acid radical but are also immediately scavenged. Exploiting this design, the MPO-generated radical on Y or W in the tripeptides (KYC and KWC, respectively) is rapidly transferred to C to form a thiyl radical, which in turn forms a non-toxic disulfide. One advantage the novel peptides of the invention provide is that highly reactive and toxic aromatic radicals are converted to less reactive thiyl radicals and, subsequently, a disulfide. A second advantage of the novel peptides of the invention is that disulfide may be reduced to its active monomeric form by glutathione. Thus, MPO activity is detoxified by a novel aromatic tripeptide which directs radical transfer rather than allowing the radical to randomly oxidize biologically relevant lipids, proteins and/or DNA to injure cells and tissues. As the product of MPO mediated oxidation of the tripeptide is a simple disulfide or mixed disulfide, which is similar to glutathione disulfide, the body is more easily able to reduce the disulfide to its active monomer, making the novel peptide of the present invention useful in vitro and in vivo.

Accordingly, the present invention is directed to highly effective peroxidase inhibitors that are composed of a central redox active aromatic amino acid, an adjacent amino acid with high reducing potential and another adjacent amino acid which stabilizes the redox center. The inventors have shown that such inhibitors based on small peptides are highly effective at: improving vasodilatation in an established murine model of vascular disease, the SCD mouse; decreasing pulmonary inflammation and collagen deposition in an established murine model of allergen-induced asthma; and, finally, increasing cardioprotection in an established rodent model of ischemia/reperfusion (I/R) injury. Taken together these data demonstrate that the configuration of the presently-disclosed peptides represents a unique structure with potent anti-inflammatory properties in a wide variety of disease models.

As can be appreciated, the composition and arrangement of the amino acids in the tripeptides are essential components for inhibiting peroxidase activity and limiting inflammation and cell death resulting from heightened aberrant peroxidase activity. It has been well documented that MPO/$H_2O_2$-mediated LDL oxidation plays an important role in pathogenesis of atherosclerosis. As simply adding tyrosine to the MPO/$H_2O_2$/LDL mixture accelerates LDL oxidation, tyrosine alone is not protective. If GSH were added to the incubation mixture, it would take several hundred μM to increase protection. Thus, the differences in the protective effects of the present tripeptides and other sulfhydryl containing peptides is that high concentrations of GSH would be required to scavenge the product of MPO activity.

Thus, GSH alone is insufficient for inhibiting MPO/$H_2O_2$-induced LDL oxidation. Finally, Lys provides a positive charge that may electrostatically interact with OH group of Tyr and SH group of Cys, this interaction might decrease the pKa of both Tyr and Cys, which can increase the reactivity of this peptide in inhibiting MPO/$H_2O_2$-induced oxidation. However, when these amino acids are arranged with the redox active Tyr or Trp sandwiched between Cys and Lys, this unique arrangement provides self-inactivation of the Tyr and Trp radical species and transfers the Tyr and Trp radical species Cys, which has a lower redox potential than Tyr. or Trp. Thus, the present tripeptides contain a short redox cascade, which efficiently transfers radicals from the aromatic amino acids to a thiol to form a S. which often reacts with another thiol to form a disulfide (—SS—), which can be easily regenerated by cellular thiol reduction mechanisms.

While no one mechanism of pharmacological action is adopted herein, the fact that the present tripeptides inhibit peroxidase-mediated LDL oxidation and mixed protein dissulfides can be reduced to their respective thiols by cellular glutathione reductase suggests that oxidized tripeptides may be regenerated intracellularly. Cellular regeneration of the tripeptides would certainly explain why the small peptides are more effective inhibitors of peroxidase mediated cell injury in vivo than in vitro. The ability of the tripeptides to improve vasodilatation, decrease pulmonary inflammation and collagen deposition, and increase cardioprotection demonstrates their potential utility as anti-inflammatory agents and underscores the universal nature of aberrant peroxidase activity in a wide variety of vascular disease.

Although KYC and KWC inhibit MPO/$H_2O_2$-mediated LDL oxidation, it is possible that these small peptides may possess alternative pathways of protection. As thiol containing proteins have been shown to form nitrosothiols when added to environments of high nitrosative stress, the present tripeptides may also form nitrosothiols in environments of high nitrosative stress. In addition, the tripeptides may also scavenge oxidants directly as both the aromatic amino acids have been shown to react with peroxynitrite as well as .$NO_2$ and .OH radicals. Thus, KYC and KWC, which are highly effective inhibitors of MPO/$H_2O_2$-mediated LDL oxidation, may be able to decrease oxidative stress induced by a wide variety of radical species. If KYC and KWC form nitrosothiols in vivo, this would mean that these tripeptides have the ability to convert potent oxidants into what many consider to be protective agents that can be used to inhibit platelet aggregation, increase vasodilatation and cardioprotection.

Previously, the inventors demonstrated that vasodilatation in SCD mice was impaired and that treatment with D-4F, a novel apoA-I mimetic that was designed to improve HDL function, increases eNOS-dependent vasodilatation in the SCD mice. In the studies described below, the inventors show that KYC dramatically increased vasodilatation in facialis arteries from SCD mice to ~60% of maximal vessel diameter change with just three weeks treatment. In their previous studies, D-4F treatments increased vasodilatation in SCD mice to ~35%. In those studies, facialis arteries isolated from untreated SCD were non-responsive to acetylcholine (ACh) stimulation. In other words vasodilatation did not increase when the SCD arteries were stimulated with ACh. Here however, vasodilatation of facialis arteries isolated from SCD mice did occur in response to ACh stimulation ~20%. Taking the increase in baseline responses into account the inventors' data indicate that 3 weeks of KYC treatments improve vasodilatation in SCD mice to the same extent as D-4F.

It has been known for some time that the aromatic amino acids, Trp and Tyr, can be oxidized by most peroxidases to rapidly form corresponding tryptophanyl and tyrosyl radicals. During this one electron oxidation process, Trp and Tyr compete against other potential substrates, such as chloride, bromide, nitrite etc, for compound I and II, and inhibit heme peroxidase to form other radicals and oxidants. On the basis that these aromatic amino acids are preventing the formation of toxic halide and nitrite radicals one might anticipate that supplementation of Trp and Tyr might prevent cell damage induced by halide radicals and other oxidants. However, Trp. and Tyr. are themselves toxic. A previous report showed that Tyr enhanced myeloperoxidase/$H_2O_2$ dependent LDL oxidation. In the present invention, toxic Trp. and Tyr. radicals are eliminated by placing a thiol, which has a lower reducing potential than Trp. and Tyr., next to Tyr and Trp and inclusion of another amino acid such as positive charged Lys making both Tyr and Cys more reactive. The result of bracketing Tyr and Trp with Lys and Cys is a series of potent peroxidase inhibitors that decrease oxidative stress and inflammation in vitro and in vivo.

Accordingly, in a first aspect, the invention provides a peptide-based inhibitor of peroxidase activity. Such peptide inhibitors are particularly useful for improving vascular function, decreasing pulmonary inflammation and increasing cardioprotection in a subject. In view of the inventors' discovery, peptide-based peroxidase inhibitors of the invention have the formula $AA_1$-$AA_2$-$AA_3$, wherein $AA_1$ is a positively charged, negatively charged, or neutral amino acid, $AA_2$ is a redox active amino acid, and $AA_3$ is an amino acid possessing a reducing potential such that $AA_3$ is capable of undergoing a redox reaction with a radical of amino acid $AA_2$. Amino acid $AA_1$ is preferably a positively charged amino acid such as lysine, arginine, or histidine. The redox active amino acid $AA_2$ is preferably tyrosine, tryptophan, chlorotyrosine, nitrotyrosine, or dimethyltyrosine. Amino acid $AA_3$ is an amino acid possessing reducing potential, preferably a sulfur- or selenium-containing amino acid, most preferably a cysteine, selenocysteine, or homocysteine. As noted herein preferred peptide-based inhibitors have the formula KYC or KWC, most preferably where the amino termini are protected by acetyl groups and the carboxyl termini are protected by amides.

In addition to the above sequences, this invention also encompasses peptides comprising retro and retro-inverso analogs of each of these sequences. In retro forms, the direction of the amino acid sequence is reversed. In inverso forms, the chirality of the constituent amino acids is reversed (i.e., L form amino acids become D form amino acids and D form amino acids become L form amino acids). In the retro-inverso form, both the order and the chirality of the amino acids are reversed. A given amino acid reference amino acid sequence and its retro-inverso form are mirror images of each other, and typically have similar functions.

In certain embodiments, peptides of the invention further contain a protecting group coupled to the amino or carboxyl terminus of the peptide, or a first protecting group coupled to the amino terminus of the peptide and a second protecting group coupled to the carboxyl terminus of the peptide. Possible protecting groups for use in this embodiment include without limitation amide, 3 to 20 carbon alkyl groups, Fmoc, Tboc, 9-fluorene acetyl group, 1-fluorene carboxylic group, 9-florene carboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), acetyl (Ac), and Trifluoroacetyl (TFA).

In certain other embodiments, the peptide contains a protecting group coupled to the amino terminal and the amino terminal protecting group is acetyl. In other embodiments, the peptide contains a protecting group coupled to the carboxyl terminal and the carboxyl terminal protecting group is an amide. In still other embodiments, the peptide contains a first protecting group coupled to the amino terminus that is an acetyl, and a second protecting group coupled to the carboxyl terminal that is an amide.

The invention also includes pharmaceutical compositions for inhibiting peroxidase activity, containing one or more of the peptides described above and a pharmaceutically acceptable carrier. Preferably these compositions are in unit dosage forms such as tablets, pills, capsules, powders, granules, sterile parenteral solutions or suspensions, metered aerosol or liquid sprays, drops, ampules, auto-injector devices or suppositories; for oral, parenteral, intranasal, sublingual or rectal administration, or for administration by inhalation or insufflation. It is also envisioned that the peptides of the present invention may be incorporated into transdermal articles designed to deliver the appropriate amount of peptide in a continuous fashion.

It is not critical whether an inhibitor according to the invention is administered directly to a peroxidase, to a tissue comprising the peroxidase, a body fluid that contacts the peroxidase, or a body location from which the inhibitor can diffuse or be transported to the peroxidase. It is sufficient that the inhibitor is administered to the subject in an amount and by a route whereby an amount of the inhibitor sufficient to inhibit the peroxidase arrives, directly or indirectly at the peroxidase.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

In certain embodiments, the peptides of the invention will be provided as pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the peptide according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Suitable dosage levels for the inhibition of peroxidase activity in a human subject (i.e, an effective therapeutic amount to inhibit peroxidase activity) is about 0.01-5000 mg/kg, per day, preferably about 0.1-500 mg/kg per day, and especially about 0.1-50 mg/kg per day.

In another aspect, the invention provides a method of reducing peroxidase activity in a subject. The method includes the step of administering to a subject in need of such therapy one or more of the peptides as described above. In certain preferred embodiments, the subject is a human or a non-human mammal. Preferably, the method includes the additional step of mixing the peptide with a pharmaceutically acceptable carrier before the peptide is administered. In preferred embodiments of the invention, the method is carried out to improve vascular function, decrease pulmonary inflammation, and/or increase cardioprotection in the subject. However, it can be appreciated that the inventive peptides act on a molecular process common to a plethora of medical diseases and conditions. Therefore, the present peptides are envisioned to be useful in treating a wide range of diseases and conditions attributable to aberrant peroxidase activity, including but not limited to, wound inflammation, hypersensitivity, digestive disease, cardiovascular disease, neuronal disease, lung disease, autoimmune disease, degenerative neurological disease, degenerative muscle disease, infectious disease, disease associated with graft transplantation, allergic disease, musculo-skeletal inflammation, and sepsis.

Methods of the invention are further envisioned to be useful in treating hypertension, peripheral vascular disease, pulmonary inflammation, asthma, atherosclerosis, diabetes, persistent pulmonary hypertension, sickle cell disease, neurodegenerative disease, multiple sclerosis, Alzheimer's disease, lung cancer, lupus, ischemic heart disease, Parkinson's disease, Crohn's disease, inflammatory bowel disease, necrotizing enterocolitis, arthritis, polymyocytis, cardiomyopathy, psoriasis, amyotrophic lateral sclerosis, muscular dystrophy, cystic fibrosis, attention deficiency hyperactive disorder, acute lung injury, acute respiratory distress syndrome, flu (including H1N1), heart failure, chemotherapy-induced heart failure, arthritis, rheumatoid arthritis, or acute myocardial infarction.

Further, methods of the invention will find use in the promotion of angiogenesis in tissues of a subject, or the promotion of angiogenesis impaired by persistent pulmonary hypertension, peripheral vascular disease or vascular disease in the myocardium in the subject, or the treatment of a disease or condition associated with abnormal, excessive blood vessel development in the subject. Methods of the invention are additionally useful in treating subjects for the reduction and/or prevention of ischemic injury to a subject's heart following an ischemic event or insult.

Of course, the invention also contemplates the use of a peptide as described and claimed herein for the manufacture of a medicament for inhibiting peroxidase activity in a subject. Such methods include the steps of (a) providing a peptide as described herein, and (b) mixing the peptide with a pharmaceutically acceptable carrier. As well, the invention encompasses the manufacture and use of medicaments specifically-purposed for treatment of one or more of the diseases/conditions described above.

EXAMPLES

The following examples are provided as further non-limiting illustrations of particular embodiments of the invention.

Peptide Synthesis. Tripeptides (Ac-KYC-amide [KYC] and Ac-KWC-amide[KWC]) were synthesized using Fmoc (N-(9-fluorenyl)methoxycarbonyl) chemistry by the Protein, Nucleic Acid Core Laboratory of the Medical College of Wisconsin and purified by a preparative HPLC. The purity and authenticity of both peptides were assured by a single peak from an RP-HPLC analysis and correct mass determined by a matrix-assisted laser desorption ionization time-of-flight mass spectrometry.

Tyrosine (Y), an aromatic amino acid, is rapidly oxidized by MPO to generate toxic tyrosyl radicals (Y.). In developing KYC, we reasoned that if this MPO substrate were going to be used to inhibit MPO then the Y. radicals that would be generated would have to be scavenged before they had a chance to oxidize other cellular targets. One of the ways to scavenge free radicals is by intramolecular electron transfer (IET). Radiation chemistry studies show that electron transfer among redox active amino acids follows the rank order of Met>Trp>Tyr>=Cys. Thus, if Cys is positioned next to Tyr, an established substrate for MPO, then based on the rank order listed above, any Y. radical that forms as a result of MPO activity would easily be transferred to Cys. Moreover, the rate constants for IET with Cys, which are on the order of $10^4$-$10^5$ $S^{-1}$, were fast enough to prevent Y. from oxidizing any downstream biological targets.

TyrCys (YC) is the shortest peptide ever used to protect Y from nitration and di-Tyr formation and is lipophilic, making it difficult to dissolve in aqueous buffers or enter subendothelial spaces where MPO might be found. However, by positioning Y between lysine (K) and cysteine (C), then the novel tripeptide of the present invention becomes more soluble in aqueous buffers than the dipeptide YC. Our enzymatic studies show that KYC is highly water soluble, can be added directly to physiological buffers and directly interacts with the active site of MPO to inhibit peroxidase activity.

This example illustrates exemplary small peptides where redox active amino acids were paired with Cys so that the thiol side chain can donate electrons to regenerate the redox reactive amino acid. The present data illustrate that a peptide combining Cys and either Trp or Tyr with a positively charged Lys increases the reactivity of the Trp or Tyr and the Cys to the Trp. or Tyr. radical as well as increase the solubility of the small peptide. The result of such a combination is a highly effective inhibitor of peroxidase activity that has potent anti-inflammatory properties in widely diverse models of vascular disease and injury.

MPO-mediated oxidation of LDL. Reaction mixtures contained LDL (0.15 mg/ml), $NaNO_2$ (100 µM), $H_2O_2$ (300 µM), MPO (20 nM) and various concentrations of KYC in a potassium phosphate buffer (100 mM, pH 7.4) containing DTPA (100 µM). LDL oxidation was monitored at 234 nm at room temperature on a HP UV/VIS spectrometer. Absorbance traces represent the average of duplicate experiments.

Murine Model of Sickle Cell Disease. Mice treated with KYC in vivo. SCD mice were treated with KYC (intraperitoneal injection: IP 0.3 mg/kg/d) or with PBS (IP 100 µL) for 3 weeks. Anesthesia was induced with Ketamine (100 mg/kg)+Xylazine (10 mg/kg) cocktail (ip) and then sacrificed by exsanguination. Facialis arteries were atraumatically dissected and maintained in cooled MOPS solution (in mM: NaCl 145, KCL 4.7, $CaCl_2$ 2, $NaH_2PO_4$ 1.2, $M_gSO_4$, 1.2, pyruvate 2, EDTA 0.02, MOPS 3.0, and glucose 5.0, at pH 7.4). Vessels were then submerged in a MOPS bath, mounted on MOPS-containing glass capillary tubes, internally pressurized (60 mmHg), and warmed to 37° C. Internal vascular diameters were measured with a calibrated video-microscope (Boeckeler). After the vessel was allowed to acclimate to 37° C. (approximately 30 min), the diameter was measured and recorded ($D_{max}$). A thromboxane analog, U46619 ($10^{-9}$ to $10^{-8}$ M), was used to preconstrict the vessel to 30%-50% of $D_{max}$. A control dose-response curve using acetylcholine (ACh, $10^{-7}$-$10^{-4}$ M) was performed and vessel diameter recorded. The vessels were washed twice with fresh MOPS buffer over 30 minutes and then incubated with L-nitroargininemethylester (L-NAME) 200 µM for 20 minutes. Vessels were then preconstricted with U46619 ($10^{-9}$ to $10^{-8}$ M) and a dose response curve using acetylcholine (ACh, $10^{-7}$-$10^{-4}$ M) was performed again. Vasodilation to papaverine (2.0×10 M) was determined after all treatments to ensure smooth muscle viability. Vasodilation was calculated as a percent of maximal vessel diameter change.

For vessels treated with KYC (ex-vivo): Using untreated SCD mice, the vessels were isolated/cannulated the same as for the mice treated with KYC in vivo. After the control dose-response curve using acetylcholine (ACh, $10^{-7}$-$10^{-4}$ M) and subsequent washing, the vessels were incubated with KYC 1.5 µg/ml for 20 minutes, pre-constricted, and exposed to acetylcholine (ACh, $10^{-7}$-$10^{-4}$ M). Vasodilation to papaverine (2.0×$10^{-4}$ M) was determined after all treatments to ensure smooth muscle viability. Vasodilation was calculated as a percent of maximal vessel diameter change.

Murine Model of Experimentally-Induced Asthma. C57BL/6J mice (12-14 wk old) from Jackson Laboratory (Bar Harbor, Me.) were housed in sterile autoclavable microisolation cages and fed standard laboratory mouse chow and water ad libitum. All protocols were approved by the Institutional Animal Care and Use Committee (IACUC) of the Medical College of Wisconsin.

Figure 1:
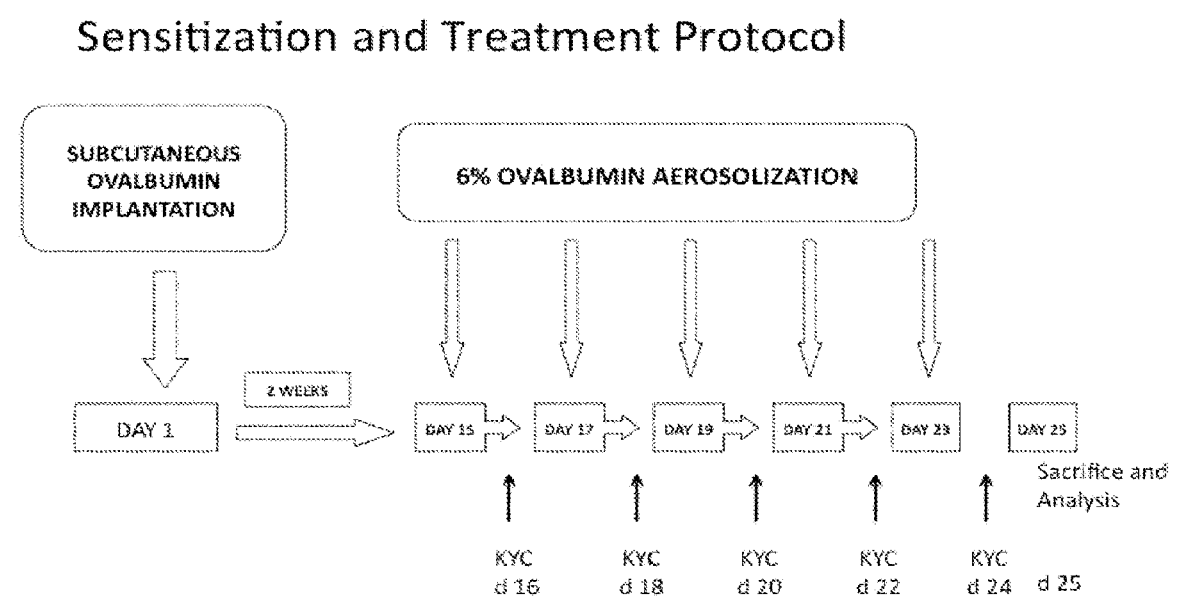

C57BL/6J mice were divided into three groups; a control group (Control), an ovalbumin (OVA)-sensitized group and an OVA-sensitized group treated with KYC. OVA sensitization was achieved using a modification of a protocol previously described by de Siqueira et al[15] (FIG. 1). This OVA sensitization protocol was chosen because it has been shown to sensitize C57BL/6 mice reproducibly for long periods of time with exaggerated allergic responses to OVA. When mice inhale aerosolized OVA, robust allergic responses are routinely observed.

Briefly, on day one, mice were anesthetized (halothane; Halocarbon Laboratories, River Edge, N.J.) and a heat-denatured OVA fragment (~80 mg, 5×2×2 mm) was implanted subcutaneously in the dorsal aspect of the neck. The incision was closed with stainless steel clips and the mouse was allowed to recover. Implantation of the heat-denatured OVA fragment initiates sensitization. On day fifteen, the implanted mice were exposed to aerosolized OVA (6% in PBS) for 30 minutes every other day for ten days. Twenty-four hours after the last OVA challenge, the mice were deeply anesthetized (halothane), sacrificed by exsanguination and the lungs removed for analysis. For the KYC-treated OVA-sensitized mice, treatments started on day 15. OVA-sensitized mice were treated with KYC (0.3 mg/kg) every other day for 10 days, a total of 5 treatments. Twenty-four hours after the last OVA challenge, the mice were deeply anesthetized (halothane) and exsanguinated and the lungs removed for histological analysis (H&E) and collagen deposition (McLetchie's Trichrome).

The standard protocol for fixing the lungs was to inflate the lung with 0.5 mL PBS-Zn-formalin prior to removal. The lungs were removed and embedded in paraffin, and sections cut (5 µm) and stained either with hematoxylin and eosin (H&E) to enhance cytoplasmic and nuclear structures or with McLetchie trichrome to visualize collagen deposition to assess thickening of basement membranes in airways and pulmonary vessels. Images were captured on a Zeiss Imager.Z1 microscope using 40×/0.95 aperture objective and Axiocam HRc camera and Axiovision Software (version 4.6) (all from Carl Zeiss, Heidelberg, Germany).

Ischemia/Reperfusion (I/R) Injury in Isolated Hearts. Rats used in this study received humane care in compliance with the Guide for the Care and Use of Laboratory Animals, by the National Research Council. Rats were maintained on a low salt (0.4% NaCl) diet with unlimited access to water. Environmental influences were minimized by maintaining rats in identical housing conditions. Dahl S (SS/Mcw male rats at 8 weeks of age were used for this study.

Modified Krebs-Henseleit bicarbonate buffer was prepared containing the following components (in mM): 118.5 NaCl, 25.0 $NaHCO_3$, 4.8 KCl, 1.2 $MgSO_4.6H_2O$, and 1.2 $KH_2PO_4$ (pH 7.4 when gassed with 95% $O_2$-5% $CO_2$) in which the calcium content was 1.8. Glucose (11.1 mM) was added to the perfusate. Before use, all perfusion fluids were filtered through cellulose acetate membranes with a pore size of 5 µm. To this perfusate, drugs (KAA, KYC) were added as needed. Animals were weighed, and heparin was administered intraperitoneally based on weight (150 IU/kg). Anesthesia was induced with pentobarbital sodium (30 mg/kg ip). Once adequate anesthesia was obtained, the abdomen was opened, and the diaphragm was separated from its chest wall attachments and the pericardium opened. The aorta was clamped and the heart excised. The heart was then immediately transferred to the Langendorff apparatus, and the aorta was cannulated and secured using silk ties. Coronary arteries were perfused at constant pressure (80 mmHg) in a retrograde fashion with Krebs buffer. The heart was immersed in a bath containing Krebs buffer at 37.2+/−0.1° C. to maintain conditions of normothermia. Left ventricular pressure (LVP) was measured isovolumetrically with a transducer connected to a thin, saline-filled latex balloon inserted into the left ventricle through the mitral valve from an incision in the left atrium.

Drug perfusion. After steady-state levels of function were reached, hearts were perfused with HZ2 (Ac-KYC-NH$_2$) or HZ3 (Ac-KWC-NH$_2$) at 50 mg/L for 40 min prior to 35 min global ischemia and 2 hour reperfusion. The protocol for perfusing isolated hearts with or without KWC or scramble peptide KAA is described in FIG. 5A.

MPO-mediated HOCl Production. MPO (20 nM) was incubated with H$_2$O$_2$ (50 μM), NaCl (150 mM), taurine (5 mM) and increasing concentrations of KYC in phosphate buffer (100 mM, pH 7.4) which also contained diethylene triamine pentaacetic acid (DTPA, 100 μM) to prevent nonspecific, divalent metal cation oxidation for 30 min. Reactions were halted by addition of catalase. Chlorotaurine was quantified using the 3,3-,5,5-tetramethylbenzidine (TMB) assay. Briefly, 400 μL of reaction solution was mixed with 100 μL of 2 mM TMB, 100 μM NaI containing 10% dimethylformamide (DMF) in 400 mM acetate buffer (pH 5.4). After 5 min, absorbance (650 nm) was recorded on a UV/Vis spectrophotometer (Agilent Model 8453).

MPO-mediated Nitration of Bovine Serum Albumin (BSA). BSA (0.5 mg/mL) was incubated with MPO (20 nM), H$_2$O$_2$ (100 μM), nitrite (100 μM) and increasing concentrations of KYC in phosphate buffer (100 mM, pH 7.4) containing DTPA (100 μM) for 30 min. Reactions were stopped by addition of catalase. Nitrotyrosine formation was assessed by western blot analysis.

MPO-mediated LDL Oxidation. Reaction mixtures contained LDL (0.15 mg/mL), NaNO$_2$ (100 μM), H$_2$O$_2$ (100 μM), MPO (20 nM) and increasing concentrations of KYC in a phosphate buffer (100 mM, pH 7.4) containing DTPA (100 μM). Rates of LDL oxidation were monitored at room temperature at 234 nm, the wavelength maximum for conjugated dienes.

HPLC Analysis. KYC oxidation products were analyzed by reverse phase HPLC using a C-18 column (2×150 mm). The peptide and products were eluted using an acetonitrile (ACN) gradient (5-10%, containing 0.1% trifluoroacetic acid (TFA)) for 20 min. Elution was monitored at both 220 nm and 280 nm.

PMA induced HOCl Formation by HL-60 cells. HL-60 cells were cultured in RPMI 1640 medium containing 10% FCS (passage 20-50). HL-60 cells were harvested by centrifugation (1000 rpm, 10 min), washed 2× with phosphate buffer (10 mM, pH 7.4) with NaCl (138 mM), KCl (2.67 mM), CaCl$_2$ (0.901 mM), MgCl$_2$ (0.493 mM) and glucose (1 mg/ml) to remove culture medium. The HL-60 cells (6×10$^6$/0.5 ml) were re-suspended in DPBS. The washed HL-60 cells were either stimulated with PMA (10 μM) or not, and then incubated with taurine (5 mM) and increasing concentrations of KYC (0.1 uM-100 μM) at 37° C. for 30 min. The reaction was stopped by addition of catalase. After centrifugation, absorbance at 650 nm of the reaction mixtures was recorded to determine chlorotaurine production, which is directly proportional to production of HOCl.

PMA-induced Superoxide Anion Formation. HL-60 cells were cultured in RPMI 1640 medium containing 10% FCS (passage 20-50). HL-60 cells were harvested by centrifugation (1000 rpm, 10 min), washed 2× with phosphate buffer (10 mM, pH 7.4) with NaCl (138 mM), KCl (2.67 mM), CaCl$_2$ (0.901 mM), MgCl$_2$ (0.493 mM) and glucose (1 mg/ml) to remove culture medium. The HL-60 cells (6×10$^6$/0.5 ml) were re-suspended in DPBS. After stimulation with PMA (10 μM), the HL-60 cells were incubated with cytochrome C (40 μM) with or without superoxide dismutase at 37° C. for 30 min. The reaction was stopped by centrifugation. Cytochrome C reduction was measured at 550 nm on a UV-Vis spectrophotometer (Agilent, Model 8453).

Vasodilatation. SCD mice were treated with KYC (0.3 mg/kg/d, intraperitoneal injections) for 3 weeks. Mice were anesthetized, euthanized by exsanguination and the facialis arteries isolated by microdissection, cannulated, and pressurized. Physiological responses to increasing concentrations of acetylcholine (ACh) were determined by videomicroscopy as previously described.

Vessel Wall Thickness. After completing the vasodilatation studies, the pressurized vessels were maximally dilated by addition of papaverine (10$^{-4}$ mol/L, 4 min), and outside and inside diameters recorded. An index of wall thickness was calculated using the following formula; ([outside diameter/inside diameter]/2)/outside diameter, as previously described.

Immunofluorescence Studies. In a separate study, SCD mice were treated with KYC (IP, 0.3 mg/kg/d). After three weeks treatment, mice were deeply anesthetized and euthanized by exsanguination. Thoracic and abdominal aortas were surgically removed and rinsed free of blood elements using ice cold PBS. Aortas were fixed, imbedded in paraffin, and sectioned.

KYC Inhibits Myeloperoxidase Oxidation of LDL. Addition of MPO/H$_2$O$_2$/nitrite to LDL dramatically increases absorbance at 234 nm in the LDL solution after a short 25 min lag time (FIG. 2). In contrast, addition of 20 μM and 100 μM KYC totally suppresses conjugated diene formation in the LDL solution for more than 2 hours. At 4 μM, KYC increased the lag time of conjugated diene formation to 90 minutes. On the basis of absorbance values 4 μM KYC reduces the rate of LDL oxidation by ~80% at the end of the 2 hour incubation. These data clearly show that KYC is a potent inhibitor of myeloperoxidase catalyzed LDL oxidation.

Figure 3:
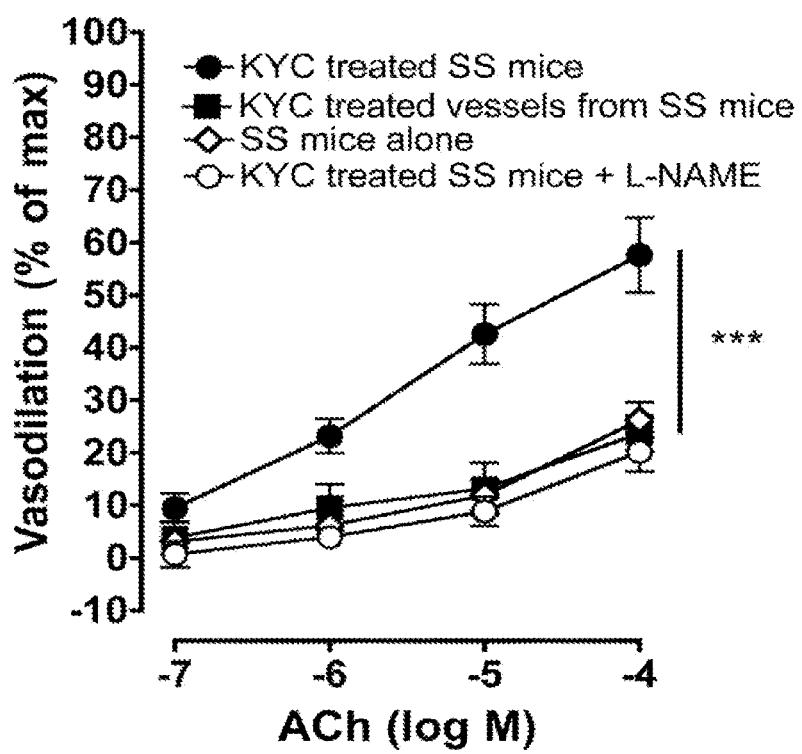
FIG. 3 illustrates that Ac-KYC-amide increases vasodilation in facialis arteries isolated from sickle cell disease (SCD) mice. The Berkeley murine model of SCD (SCD mice) were euthanized after anesthesia, and facialis arteries were isolated. The isolated and pressurized facialis arties from SCD mice were treated with HZ2 (KYC, 1.5 μg/mL, final concentration) for 20 min. The vasodilation of pressurized arterioles was determined according to the description in the Methods section.

KYC Improves Vasodilation in SCD Mice. Plasma MPO levels are increased in SCD mice compared with the levels in control mice. Treatment of SCD mice with KYC increases vasodilatation in pressurized facialis arteries to nearly 60%, by an L-NAME inhibitable mechanism (FIG. 3). These data strongly suggest that KYC treatments increase eNOS-dependent vasodilatation in SCD mice. Interestingly, directly adding KYC to the vessel bath containing facialis arteries from non-treated SCD mice did not increase vasodilatation in response to ACh.

Figure 7:
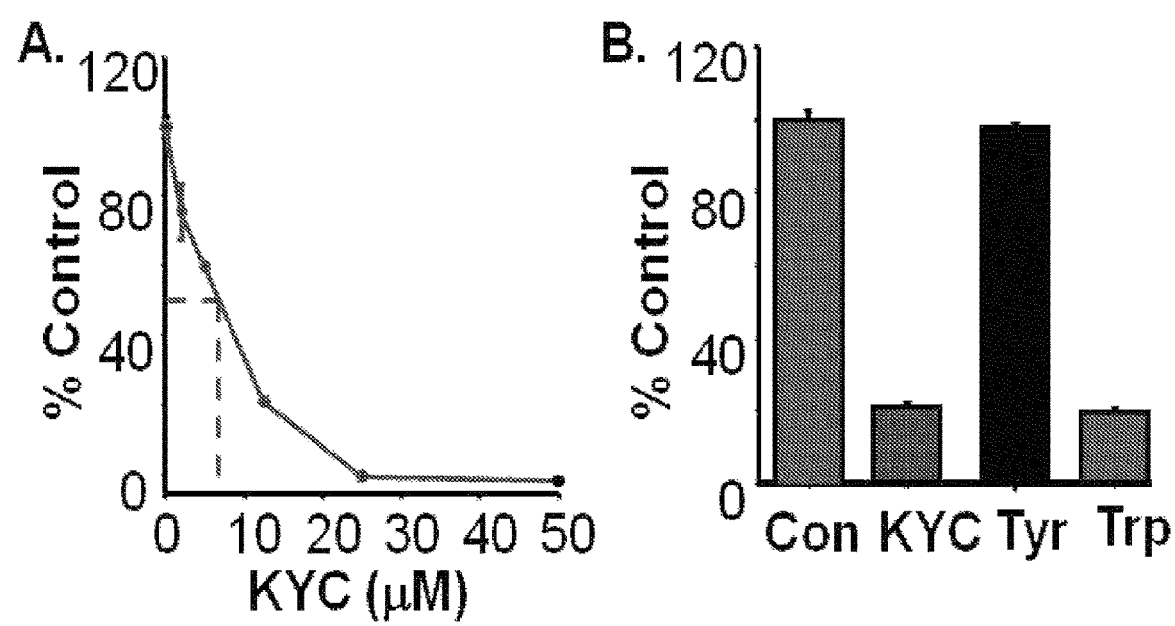
FIG. 7A. KYC inhibits HOCl formation. After incubation of 20 nM MPO, 50 μM $H_2O_2$, 150 mM NaCl, 5 mM taurine and KYC in an 100 mM phosphate buffer (pH 7.4)-DTPA (100 μM) for 30 min, formed chlorotaurine was quantified by KI/TMB assay.
FIG. 7B. The efficiency of HOCl inhibition. Inhibition efficiency of KYC was compared to Tyr, GSH and Trp at 12.5 μM.

KYC Inhibits MPO HOCl production in SCD mice. FIG. 7A shows that KYC dose-dependently inhibits MPO production of HOCl, with an IC$_{50}$ of ~7 μM. At 25 μM, KYC completely inhibits MPO-dependent HOCl production. FIG. 7B compares the effects of KYC on MPO HOCl production to the effects of tyrosine and tryptophan. These data show that the ability of KYC to inhibit MPO HOCl production is comparable to that of tryptophan. Tyrosine alone has little if any effect on MPO HOCl production.

KYC inhibits MPO by thiol-independent mechanisms. FIG. 7B shows that KYC is significantly more effective at inhibiting MPO-dependent HOCl production than GSH ($p<0.01$). These data indicate KYC inhibits MPO by mechanisms beyond those mediated by thiol scavenging.

Specifically, this data suggest that KYC inhibits MPO activity by at least two mechanisms. Previously it was shown that the MPO/$H_2O_2$/$NO_2^-$ reaction system oxidized peptides that contained Tyr into conjugated peptides joined by a di-Tyr covalent bond or to peptides that contained 3-nitrotyrosine. Additional ESR spin trapping studies showed that although MPO oxidizes Y in the peptides to a Y. radical, including a Cys in the peptide protected it from forming a di-Tyr linkage or from undergoing tyrosine nitration. Although these reports show that intramolecular electron transfer (IET) is highly effective for protecting tyrosine in peptides from being oxidatively modified, no evidence existed prior to the present invention suggesting that peptides containing either Y or C or combinations of Y and C could be used to inhibit MPO activity.

Accordingly, because KYC contains Y, it competes with $Cl^-$ and $NO_2^-$ for access to the active site of MPO, and in so doing, prevents these substrates from being transformed into HOCl and .$NO_2$. The advantage in using a competitive inhibitor rather than a suicide inhibitor is that the targeted peroxidase is still available for generating toxic oxidants to kill invading bacteria. Further, as the inhibitor is based on a known MPO substrate, non-specific interactions with other peroxidase enzymes are reduced, which should decrease toxicity.

Second, internal scavenging of Y. in KYC prevents Y. from oxidizing other biological targets. By placing C in close proximity to Y when highly reactive Y. radicals are formed by MPO activity they are scavenged by the thiol of C to form a less reactive C. radical. The C. radical is finally scavenged when 2 KYC. combine to form a KYC disulfide. As GSH and DTT are both able to reduce KYC disulfide to an active monomer, one advantage, which remains to fully tested, is that KYC may actually exploit the body's natural anti-oxidant defense mechanisms to facilitate inhibition of MPO activity. This type of biochemistry is analogous to how GSH is oxidized to GSSG disulfide by lipid hydroperoxides and then regenerated by GSH or GSH peroxidases.

Figure 8:
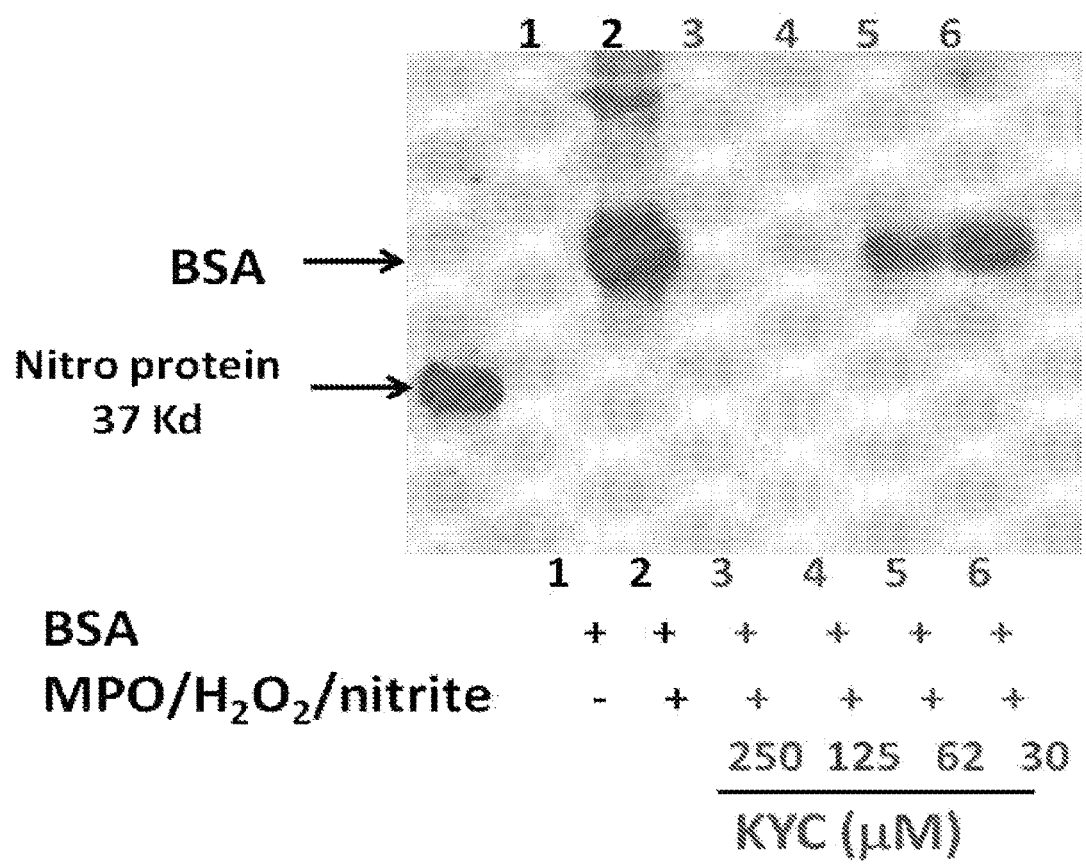
FIG. 8. Western blot analysis for nitrotyrosine: Effect of KYC on MPO-mediated nitration of BSA. BSA (0.5 mg/ml) was incubated with MPO (20 nM), $H_2O_2$ (100 μM), nitrite (100 μM) and various amount of KYC in a phosphate buffer (100 mM, pH 7.4)-DTPA (100 mM) for 30 min. The reaction was stopped by catalase. The resulting nitrotyrosine was detected by western blot.

KYC inhibits MPO-mediated protein nitration. FIG. 8 shows that KYC dose-dependently inhibits MPO-mediated nitration of BSA. Compared with the positive control, 30 µM KYC inhibits MPO-mediated BSA nitration (FIG. 8, lane 2 vs. 6) and essentially ablates BSA nitration at 250 µM (FIG. 8, lane 3).

KYC inhibits LDL oxidation by the MPO/$H_2O_2$/nitrite reaction system. FIG. 9A shows that the MPO/$H_2O_2$/nitrite dramatically increases LDL oxidation (red line), which is consistent with reports showing that MPO oxidizes biological lipids by generating nitrogen dioxide radicals. Adding KYC to MPO/$H_2O_2$/nitrite dose-dependently increases the lag time and decreases LDL oxidation. At 25 µM, KYC completely suppresses oxidation. These data demonstrate that KYC is a potent inhibitor of MPO-mediated LDL peroxidation.

KYC completely suppresses MPO/$H_2O_2$/nitrite-mediated LDL oxidation. The effects of KYC on MPO/$H_2O_2$/nitrite mediated LDL oxidation were compared with those of Tyr and GSH. FIG. 9B shows that KYC completely suppresses MPO/$H_2O_2$/nitrite-mediated LDL oxidation. In contrast, Tyr actually accelerates and enhances LDL oxidation. Although GSH increased the lag time of MPO mediated LDL oxidation in the presence of nitrite, for all practical purposes GSH was ineffective for inhibiting LDL oxidation when compared with KYC.

Figure 9:
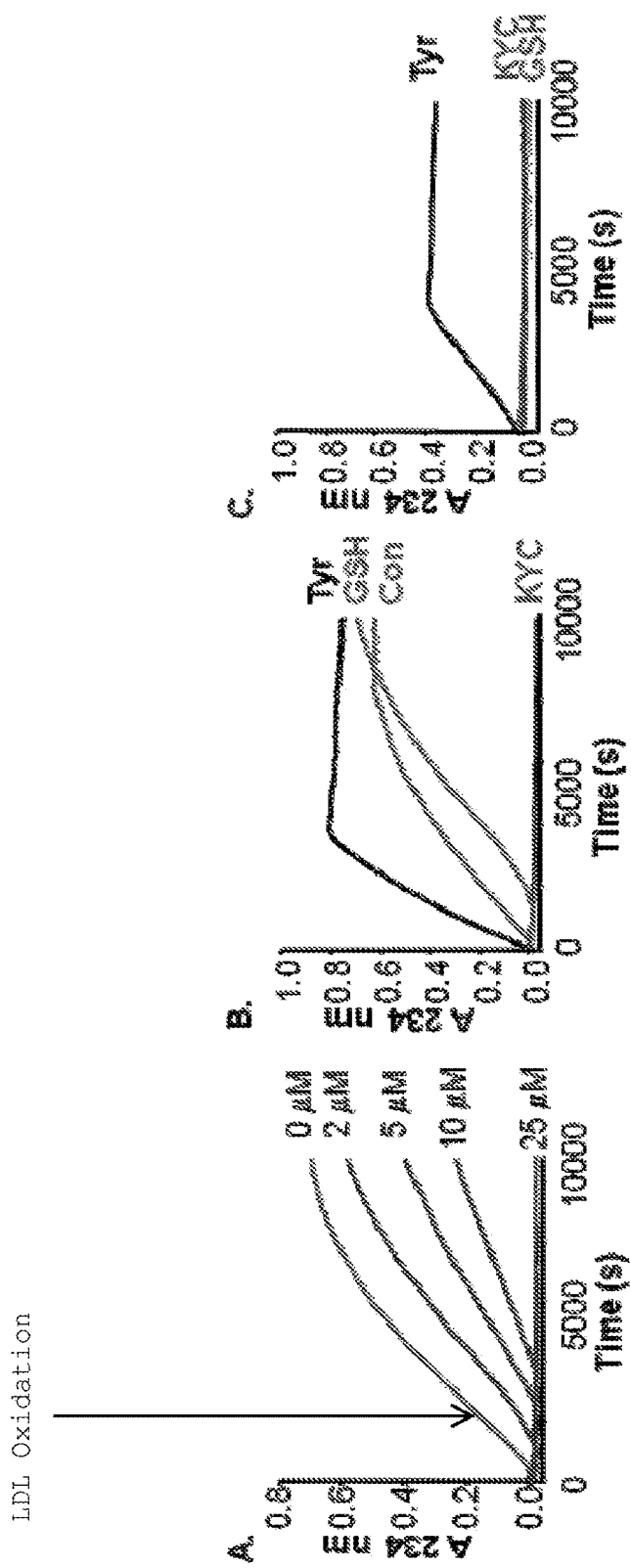
FIG. 9A. KYC inhibits LDL oxidation. LDL (0.15 mg/ml) was mixed with $NaNO_2$ (100 μM), $H_2O_2$ (100 μM), MPO (20 nM) and KYC an 100 mM phosphate buffer (pH 7.4)-DTPA (100 μM). LDL oxidation was monitored at 234 nm.
FIG. 9B. Comparing the effects of KYC, GSH and Tyr (25 μM each) on $MPO/H_2O_2/NO_2^-$-mediated LDL oxidation.
FIG. 9C. Comparing the effects of KYC, GSH and Tyr (25 μM each) on $MPO/H_2O_2$-mediated LDL oxidation.

Additional insight into the mechanisms by which KYC inhibits MPO-mediated LDL oxidation were gained by repeating the MPO/$H_2O_2$ oxidation studies in the absence of nitrite. FIG. 9 shows that Tyr increases MPO-mediated LDL oxidation. In contrast, KYC and GSH both inhibited LDL oxidation. GSH does not typically enter the active site, but if it does, if for/by completely different mechanisms, GSH scavenges HOCl when KYC enters the active site.

Figure 10:
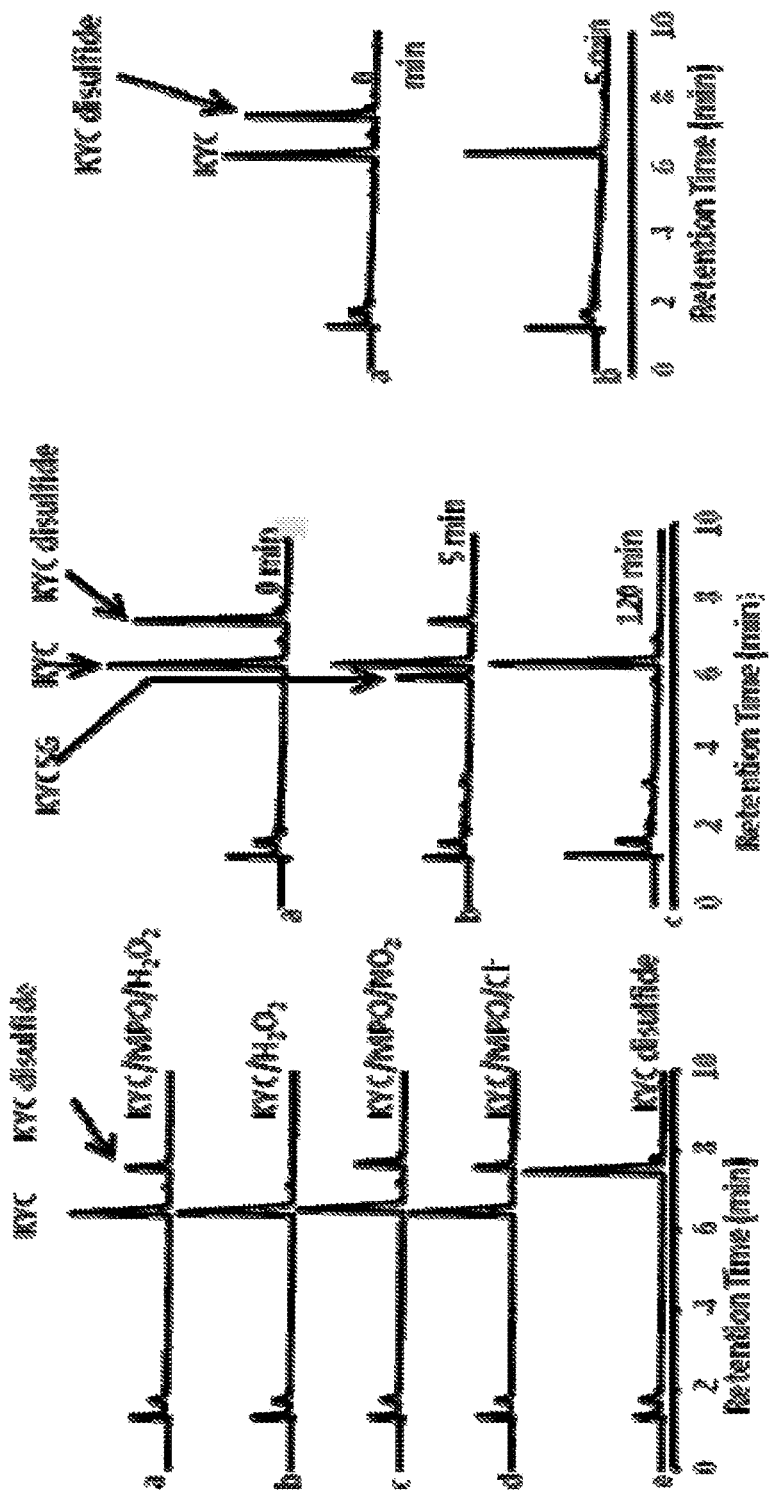
FIG. 10A. HPLC analysis of KYC products from various MPO-mediated oxidation reactions. KYC (440 μM) was incubated with MPO (30 nM), hydrogen peroxide (100 μM) and $NaNO_2$ (0.5 mM) or NaCl (100 mM) in 100 mM phosphate buffer, pH 7.4 containing DTPA (100 μM) at room temperature for 30 min and then the product was analyzed by HPLC.
FIG. 10B. GSH reduces KYC disulfide. 440 μM KYC was mixed with MPO (50 nM) and hydrogen peroxide (100 μM) for 2 hr as in A. 50 μL of A was mixed with 50 μl of GSH (10 mM) for 5 min and 2 hr at room temperature and resulted products were analyzed by HPLC.
FIG. 10C. DTT reduces KYC disulfide 440 μM KYC was mixed with MPO (50 nM) and hydrogen peroxide (100 μM) for 2 hr as above. 50 μL of A was mixed with 50 μl of DTT (0.5 mM) for 5 min at room temperature and product was analyzed.

HPLC analysis shows that the MPO/$H_2O_2$ reaction system oxidizes KYC to KYC disulfides (FIG. 10A). In contrast, reports by others show that MPO does not oxidize GSH. These data (FIGS. 9C and 10A) taken together show that the mechanisms by which KYC and GSH inhibit LDL oxidation are completely different. Thus, one reason why KYC is so efficient at inhibiting MPO-mediated LDL oxidization is that KYC directly interacts with MPO to inhibit oxidant generation whereas GSH is only able to scavenge oxidants after they are generated. Therefore, they must out compete the native biomolecules to ensure protection whereas KYC stops the release of a toxic oxidant before it has a chance to oxidize native biomolecules.

Analysis of products from MPO/$H_2O_2$/nitrite (FIG. 10, trace c) or MPO/$H_2O_2$/chloride (FIG. 10, trace d) mediated KYC oxidation show that the most abundant oxidation product in both reactions is KYC disulfide. These data suggest that regardless of the conditions under which MPO oxidizes KYC, in the presence of nitrite or chloride, the major product is the KYC disulfide, not dityrosine. Such findings clearly indicate that the cysteine in the tripeptide efficiently detoxifies tyrosyl radicals generated in the tripeptide by MPO-mediated oxidation. These studies demonstrate that KYC is a potent inhibitor of MPO/$H_2O_2$/nitrite and MPO/$H_2O_2$/chloride mediated LDL oxidation and that IET plays an important role in the mechanisms by which KYC inhibits MPO-mediated LDL oxidation.

KYC disulfides are reduced by glutathione or dithiothreitol (DTT). FIG. 10B, trace b shows that KYC disulfide is reduced to two products, which based on retention time is KYC (~6.4 min) and a mixed disulfide (KYC-[S—S]G, ~6 min). Longer incubations with GSH completely reduced the KYC disulfide to KYC monomer (FIGS. 10A-10B). DTT completely reduced KYC disulfide to monomer within five min (FIG. 10B). These data demonstrate that after KYC is oxidized and forms a simple or mixed disulfide, KYC monomers can be regenerated. As disulfides of this tripeptide appear to be easily reduced by physiologically relevant concentrations of GSH the possibility exists that KYC disulfides may be regenerated into KYC monomers in vivo.

Figure 11:
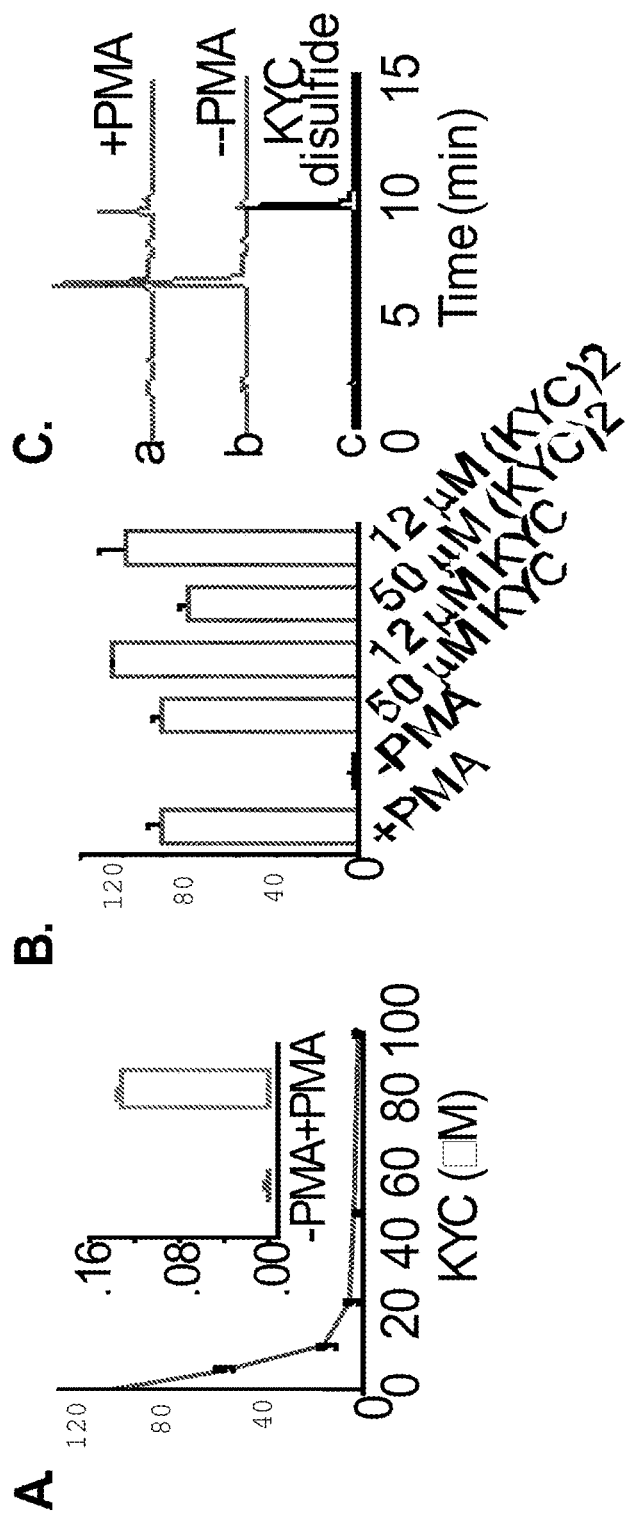
FIG. 11A. KYC inhibited HOCl formation. HL-60 cells ($6\times10^6$) were incubated with PMA and taurine (5 mM) in PBS at 37° C. for 30 min. The reaction was stopped by catalase. After centrifugation, chlorotaurine was quantified by the KI/TMB assay.
FIG. 11B. The effect of KYC and its disulfide on NOX activity. The $O_2^-$. formation was analyzed by SOD-inhibitable Cyt C reduction assay, the HL-60 cells was incubated with cytochrome C (40 μM) with or without superoxide dismutase at 37° C. for 30 min. The reaction was stopped by catalase. After centrifugation, the reduction of cytochrome C was determined at 550 nm by a UV-Vis spectrophotometer.
FIG. 11C. HPLC product analysis. KYC was incubated with HL-60 cells and PMA at 37° C. for 30 min. the KYC oxidation products were analyzed by HPLC with a C-18 column (2.3×150 mm).

KYC inhibits MPO activity in cells. HL-60 cells were stimulated with PMA and effects of KYC on HL-60 cell HOCl production were assessed using the TMB assay. HL-60 cells, when stimulated with PMA generate high levels of HOCl (FIG. 11A, inset). However, without PMA stimulation, HL-60 cells produce little, if any HOCl (FIG. 11A, inset). KYC dose-dependently inhibits HOCl production by the PMA-stimulated HL-60 cells with an $IC_{50}$~7 µM (FIG. 11A). Since MPO-mediated HOCl formation also depends on $H_2O_2$ which is derived from $O_2^-$. generation by NADPH oxidase (NOX), we next investigated whether KYC or KYC disulfide inhibits HL-60 cell HOCl production by impairing NOX generation of $O_2^-$. Cytochrome C assays revealed that neither KYC nor KYC disulfide have any significant effect on $O_2^-$. production in PMA-stimulated HL-60 cells (FIG. 11B). HPLC analysis revealed that KYC disulfide was the major oxidation product of PMA-stimulated HL-60 cells. Taken together, these data suggest that KYC inhibits MPO activity but not NOX activity.

Figure 12:
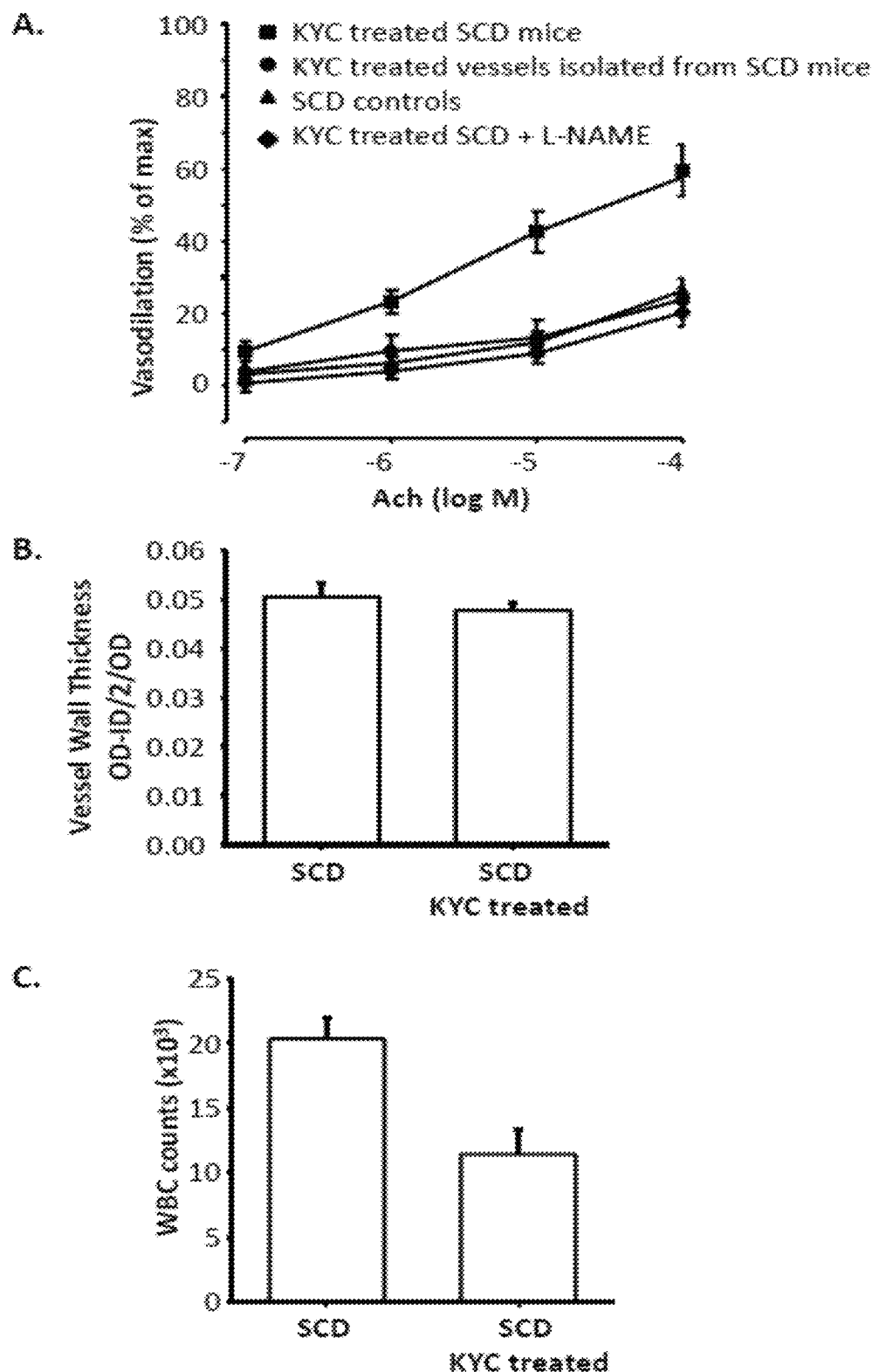
FIG. 12A. KYC treatments dramatically increase endothelium and endothelial nitric oxide (eNOS)-dependent vasodilatation in pressurized facialis arteries isolated from SCD mice.
FIG. 12B. KYC reduces vessel wall thickness.
FIG. 12C. KYC reduces chlorotyrosine and MPO levels in the aortas of SCD mice compared with non-treated SCD mice. KYC treatments reduced WBC counts in SCD by more than half.
Figure 13:
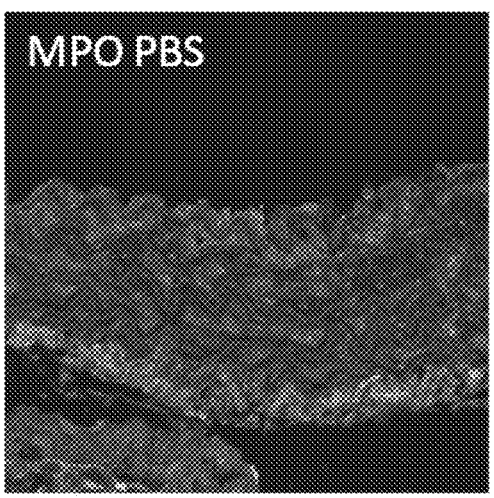
FIG. 13. Effects of KYC treatment on MPO and Cl-Tyr in arteries isolated from SCD mice of SCD mice.
Figure 13:
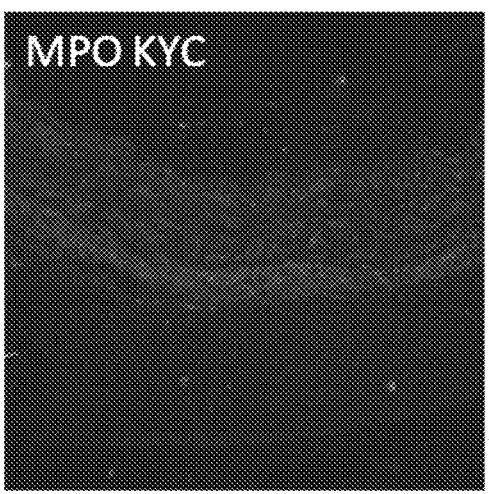
Figure 13:
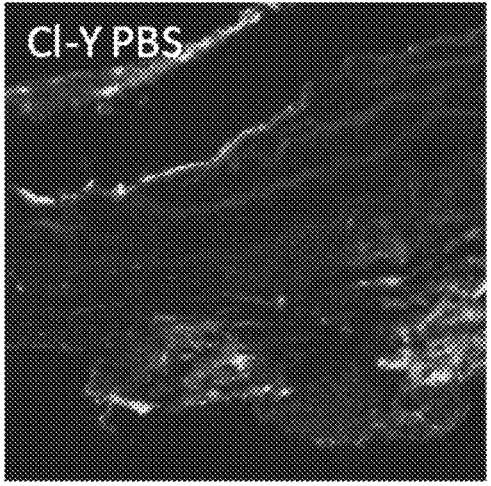
Figure 13:
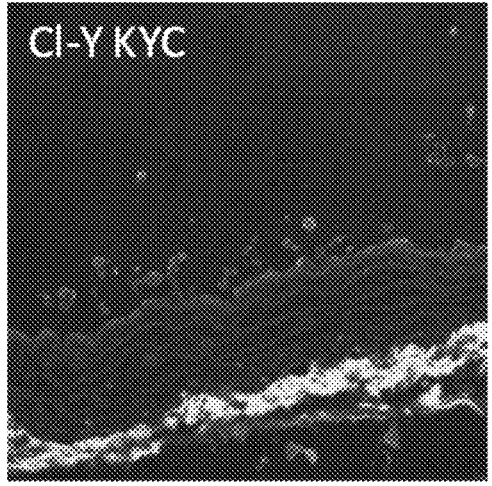
Figure 13:
Figure 13:
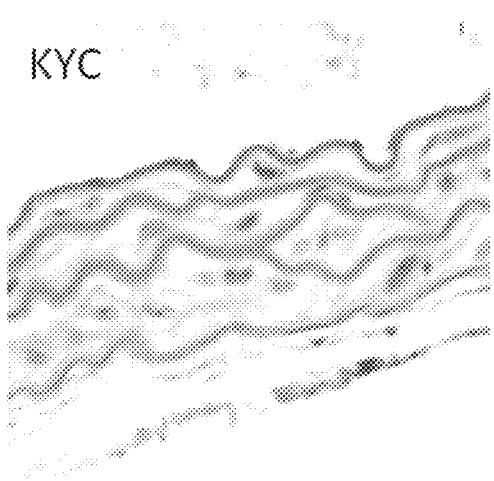

MPO improves vascular function in SCD mice. To determine whether inhibiting MPO improves vascular function and/or reduces inflammation in vivo, SCD mice were treated with KYC for three weeks. FIG. 12A shows that KYC treatments dramatically increases endothelium and endothelial nitric oxide (eNOS)-dependent vasodilatation in pressurized facialis arteries isolated from SCD mice. Measurements of inside and outside vessel diameters after incubation with papaverine (used to induce maximal vasodilatation) reveals that KYC also reduces vessel wall thickness (P=0.10) (FIG. 12B). Such physiological and structural changes are consistent with immunofluorescent studies showing that chlorotyrosine and MPO levels are reduced in the aortas of KYC-treated SCD mice compared with non-treated SCD mice (FIG. 13). High WBC counts are indicative of on-going inflammation in SCD and predictive of future vaso-occlusive events. Accordingly, WBC levels were quantified in the SCD mice using standard cytometry assays. FIG. 12C shows that KYC treatments reduced WBC counts in SCD by more than half.

Figure 4:
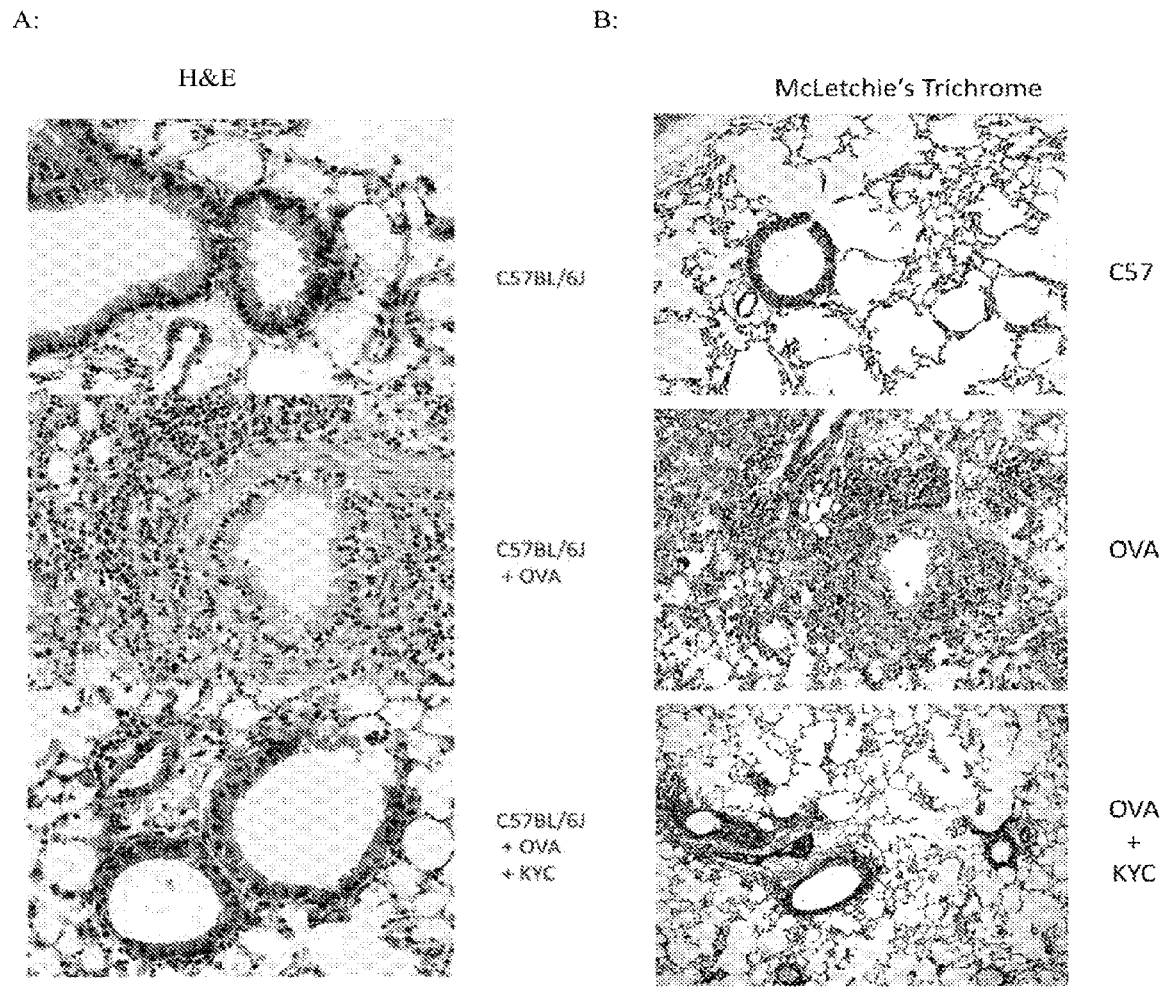
FIG. 4 shows the effects of Ac-KYC-amide on pulmonary inflammation in an OVA-murine model of experimentally-induced asthma. The model was established according to the methods section. The tissues were embedded in paraffin, sections were cut (5 μm) and stained either with hematoxylin and eosin (H&E)(a) or with McLetchie trichrome (b). Images (40×) were captured on a Zeiss Imager.Z1 microscope using 40×/0.95 aperture objective and Axiocam HRc camera and Axiovision Software (version 4.6) (all from Carl Zeiss, Heidelberg, Germany).

KYC Inhibits Pulmonary Inflammation in a Murine Model of Asthma. OVA sensitization induces dramatic increases in eosinophil infiltration in the lungs of C57BL/6J mice (FIG. 4A, middle panel vs. top panel). KYC treatments of OVA-sensitized mice markedly reduce eosinophil infiltration to essentially control levels (bottom panel (KYC) vs. middle panel (OVA) and top panel (control). Collagen deposition can be seen in FIG. 4B. OVA sensitization induces dramatic increases in collagen deposition in the lungs of C57BL/6J mice (FIG. 4B, middle panel vs. top panel). KYC treatments of OVA-sensitized mice markedly reduces collagen deposition to control levels (bottom panel (KYC) vs. middle panel (OVA) and top panel (control). These data demonstrate that KYC is an effective inhibitor of pulmonary inflammation and collagen deposition in an established murine model of allergen-induced asthma.

Figure 5:
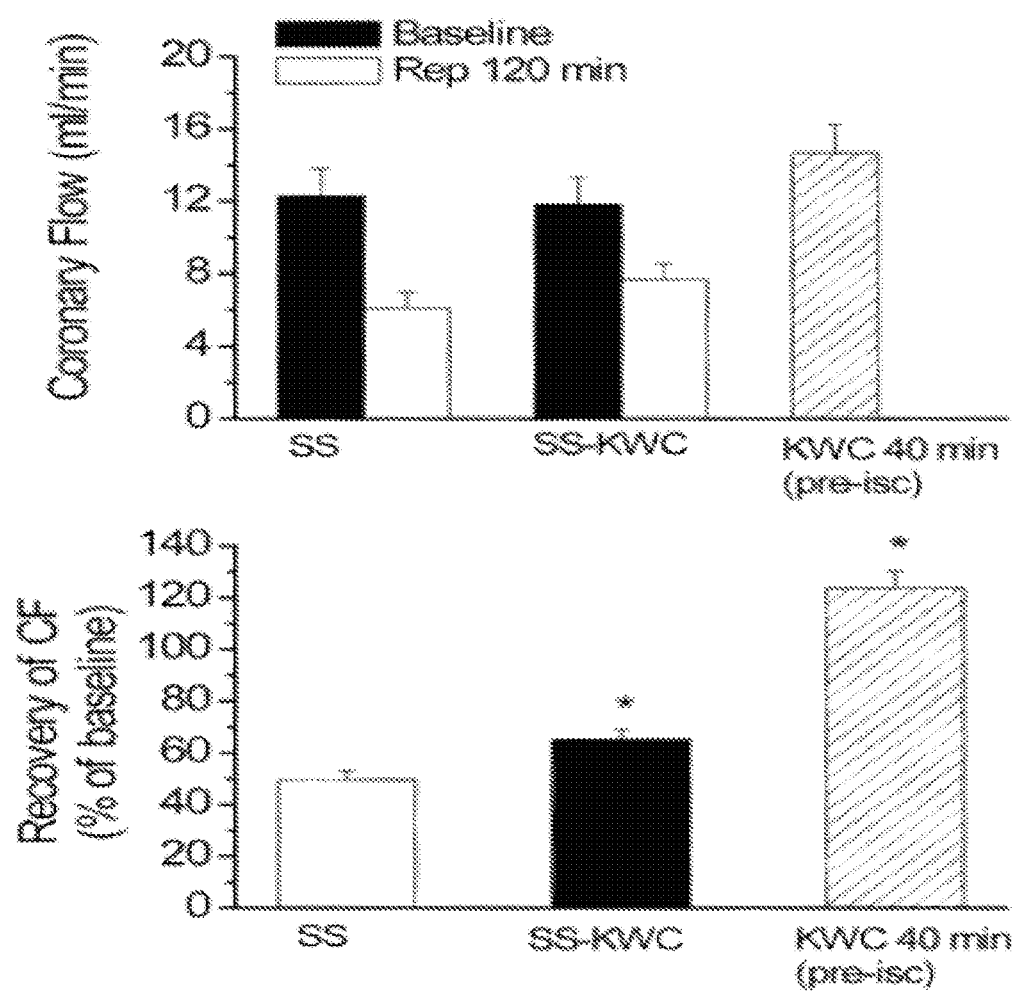
FIG. 5A illustrates the Ischemia Protocol discussed in the examples section.
FIG. 5B shows that KWC treatments increase cardioprotection in SS/Mcw rat hearts. KAA, a negative control, which is missing the central redox active aromatic amino acid and the adjacent cysteine, does not.
FIG. 5C shows that KWC increases coronary blood flow in SS/Mcw rat hearts subjected to ischemia and even in isolated hearts prior to ischemia.
Figure 5:
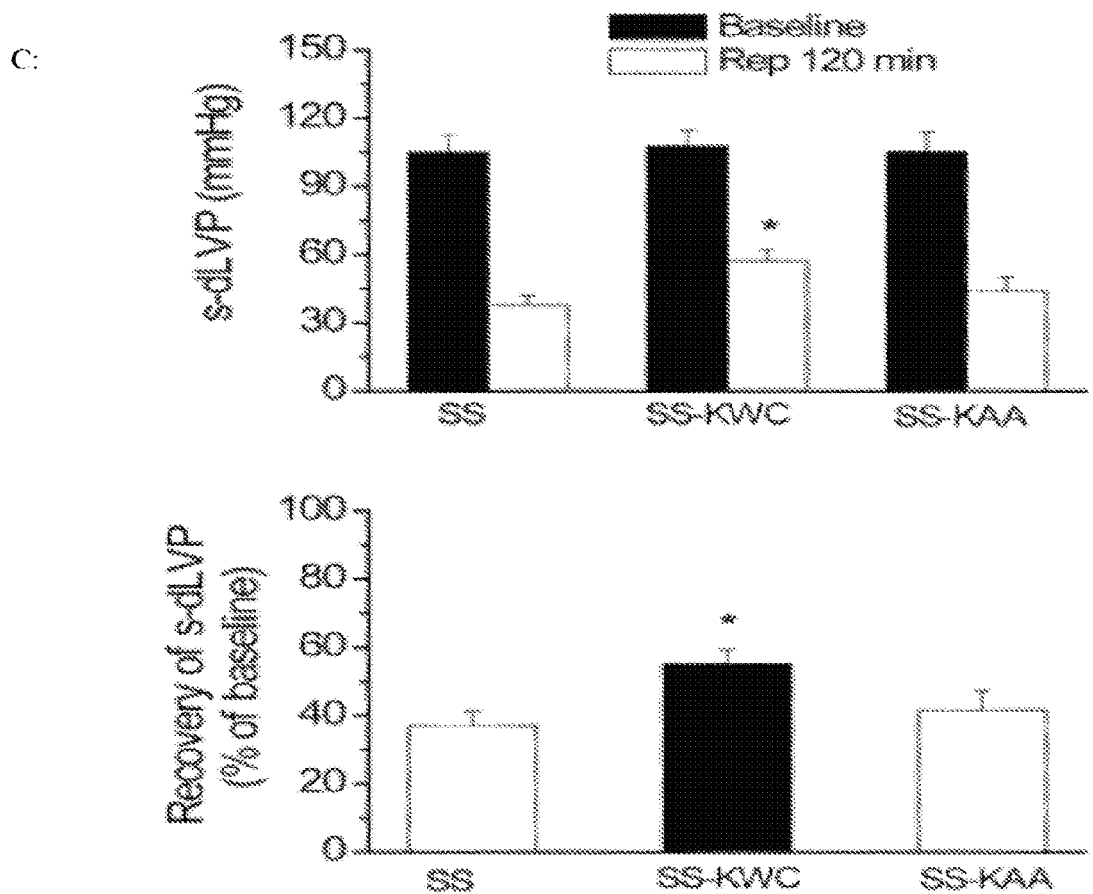

KWC Inhibits Ischemia/Reperfusion (I/R) Injury in Isolated Hearts. To determine the role of peroxidase in ischemic injury, we perfuse isolated SS/Mcw rat hearts with KWC prior to global I/R injury. FIG. 5 shows that KWC significantly increases left ventricular developed pressure (LVDP) and percent recovery of LVDP after I/R injury compared to baseline in SS rat hearts (38±3.9 mmHg and 37.1±4.3% vs. 57.3±4.8 mmHg and 55.3±4.1%, p<0.01). In hearts treated with a peptide control, KAA, cardiac functional recovery increases but not significantly compared to the untreated control group (38±3.9 mmHg and 37.1±4.3% vs. 43.8±6.4 mmHg and 41.7±5.5%). Coronary flow rates increase more than 20% after KWC is perfused into the hearts (FIG. 5). After I/R, coronary flow rates in the KWC treated hearts show a higher percent recovery than in the untreated control group (65.2±4 vs. 49.6±3.4, p<0.05). These data show that KWC increases resistance to I/R injury in DahlS (SS/MCW) rat hearts.

Figure 6:
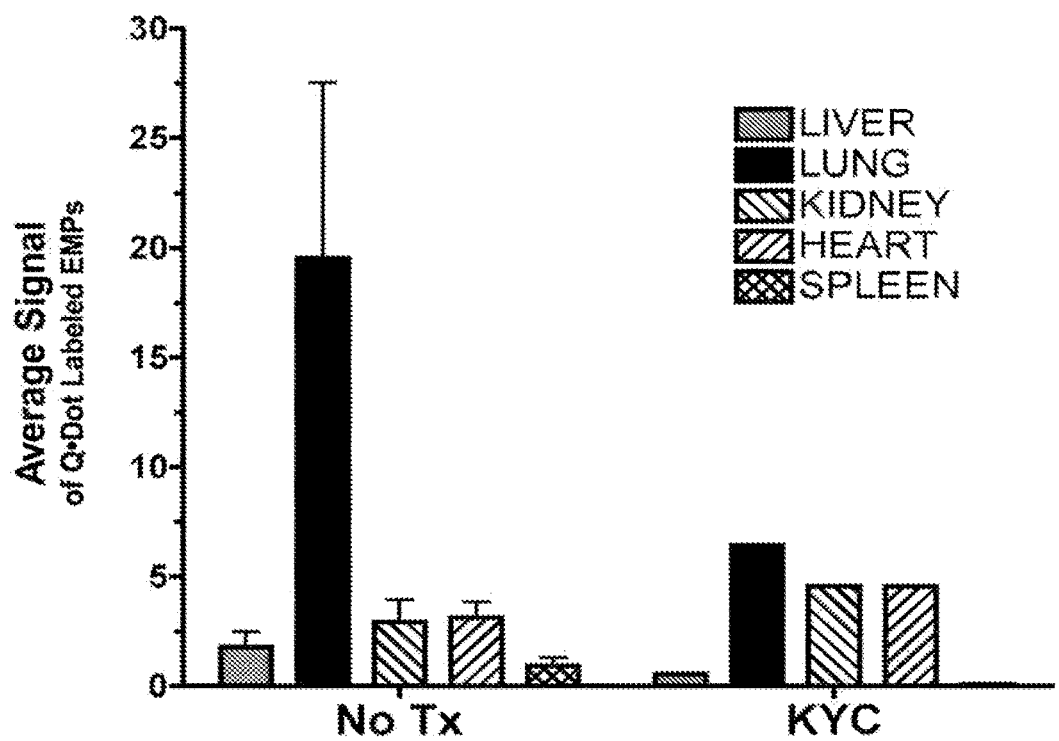
FIG. 6 illustrates that pretreatment and treatment of EMP-injected mice with KYC dramatically decreased pulmonary retention of Q-dot labeled EMPs.

KYC Inhibits Acute Lung Injury. Inflammation and sepsis induce the release of endothelial cell microparticles (EMPs). Increased production of EMPs is hypothesized to play a causal role in the mechanisms mediating acute lung injury (ALI). To test this hypothesis, the inventors incubated human umbilical vein endothelial cells with PAI-1, which is well-recognized for inducing endothelial cells to generate EMPs. The EMPs were collected by ultracentrifugation, resuspended in physiological saline solution and then labeled with Q-dots. The Q-dot labeled EMPs were counted and then injected into C57BL/6J mice to achieve a final concentration of 100,000 EMPs/mL of blood. Mice were pretreated with phosphate buffered saline (FIG. 6) or KYC and then were injected with Q-dot labeled EMPs alone or Q-dot labeled EMPs plus KYC (FIG. 6). Biodistribution studies reveal that pretreatment and treatment of EMP-injected mice with KYC dramatically decreases pulmonary retention of Q-dot labeled EMPs (FIG. 6).

Discussion. The above examples illustrate that the novel tripeptides of the present invention effectively inhibit peroxidase mediated LDL oxidation, increase vasodilation in SCD mice, inhibit eosinophil infiltration and collagen deposition in asthma mice and decrease ischemic injury of the heart. As peroxidase enzymes share many similarities with respect to mechanisms of activation, the novel tripeptides of the present invention may be effective for inhibiting peroxidase activity in a wide variety of peroxidases; myeloperoxidase, eosinophil peroxidase, vascular peroxidase I, and methemoglobin. In addition, for the reasons discussed above, the novel tripeptides of the present invention may also be capable of scavenging toxic oxidants and free radicals.

The examples described above also show, for the first time, that the novel KYC tripeptide of the present invention effectively inhibits MPO-mediated HOCl formation, protein nitration and LDL oxidation. Further, the above data illustrate that KYC inhibits MPO activity in PMA-activated HL-60 cells but not superoxide anion production, demonstrating that KYC specifically targets MPO. When used to treat SCD mice, KYC increases endothelial- and eNOS-dependent vasodilatation as well as decreases wall thickness in pressurized facialis arteries. KYC treatments decrease immunostaining for MPO and chlorotyrosine, a specific biomarker of MPO activity, in aortic sections of the treated SCD mice. Further evidence that KYC decreases inflammation is the observation that peripheral white blood cell counts were reduced by half in SCD treated with KYC. Taken together, these data demonstrate that KYC is an effective, specific inhibitor of MPO that can be used to improve vascular physiology and decrease inflammation in SCD.

The novel peptide of the present invention therefore provides the first inhibitor of MPO that has been used in an animal model of vascular disease that actually improves vascular function and decreases inflammation without inducing any apparent toxicity. For example, the MPO/$H_2O_2$ reaction system oxidizes KYC to a KYC disulfide. That is not the case with GSH, which is not oxidized by simple MPO/$H_2O_2$ reaction systems because it does not enter the active site of MPO. Thus, when SCD mice were treated with KYC, decreased immunostaining for chlorotyrosine, a fingerprint of MPO activity, was observed. However, KYC treatments also decreased MPO staining in the aortic sections and reduced circulating levels of WBC in the SCD mice. The decrease in chlorotyrosine staining could have resulted from a reduction in circulating WBC and subsequent release of MPO as well as from an inhibition of vascular MPO activity. Regardless, treating SCD mice with KYC, shown above to inhibit MPO activity, dramatically improved vasodilatation in SCD mice. Such observations are consistent with the notion that KYC is a specific inhibitor of MPO activity.

The importance of MPO to vascular disease and inflammation cannot be understated. For more than 20 years, MPO has been implicated in the oxidative modification of lipoproteins (both LDL and HDL), vessel wall matrix and cells. Some of the strongest evidence suggesting that MPO plays a causal role in vascular disease are data showing that both MPO and chlorotyrosine are present and co-localized in human atherosclerotic plaque. In conclusion, KYC, a novel tripeptide, is a potent inhibitor of MPO activity that improves vasodilatation and decreases inflammation in an established murine model of SCD. Thus, KYC is an effective, specific inhibitor of MPO activity that may be useful for improving vascular function and reducing inflammation in SCD.

Example 2

Inhibition of Myeloperoxidase Activity by N-acetyl Lysyltyrosylcysteine Amide Myeloperoxidase (MPO) is a heme peroxidase released from activated neutrophils, macrophages and monocytes that plays important roles in host defense. Ferric MPO reacts with hydrogen peroxide ($H_2O_2$) to form compound I, an oxy-ferryl-cation radical (P.$Fe^{4+}$=O) intermediate. This intermediate can oxidize a wide variety of substrates to generate an equally wide variety of toxic oxidants and free radicals to kill invading bacteria and viruses. Compound I oxidizes (pseudo) halides (such as chloride ($Cl^-$), bromide ($Br^-$) and thiocynate ($SCN^-$)) via direct, two-electron reduction (halogenations cycle) to form corresponding (pseudo)hypohalous acids (such as HOCl, hypobromous acid (HOBr) and hypothiocynate (HOSCN)). MPO also oxidizes organic substrates such as Tyr and Trp to form tyrosyl (Tyr.) and tryptophanyl (Trp.) radicals, respectively as well as a wide variety of ionic species (nitrite ($NO_2^-$), ascorbate and urate) via one-electron reduction (peroxidation cycle) to form free radicals (nitrogen dioxide radicals (.$NO_2$), ascorbyl radicals and urate radicals). Even though MPO is released to kill invading viruses and bacteria unfortunately, its release and pro-oxidant effects can also occur from activated immune cells even in the absence of infection.

Growing evidence supports the idea that MPO plays important roles in the pathogenesis of disease by increasing oxidative and nitrosative stress. Oxidative stress induced by aberrant MPO activity has been observed in inflammatory lung disease, rheumatoid arthritis, peripheral artery disease, cardiovascular disease and diabetes. Even basic science studies in rats have shown that MPO directly correlates with severity of myocardial infarction. Recently, immunochemical studies revealed that MPO is expressed in microglia, astrocytes and certain types of neurons, suggesting that MPO could play an important role in neurodegenerative disease, such as multiple sclerosis, Alzheimer's and Parkinson's disease. Interestingly, MPO has even been implicated as a risk factor for some forms of cancers.

MPO mediates oxidative/nitrosative stress via oxidation of essential biomolecules. MPO oxidation of lipids and lipoproteins such as LDL and HDL is hypothesized to play a causal role in atherosclerosis. HOCl generated by MPO has been shown to oxidize lipids to a variety of toxic products. HOCl oxidizes plasmalogens to α-chlorofatty aldehydes, cholesterol to generate chlorinated sterols and cholesterol ozonolysis products. Finally HOCl reacts with unsaturated fatty acids in phosphatidylcholine to yield both lysophospholipids and chlorohydrins. Likewise, HOBr, which can also be generated by MPO, has been shown to convert unsaturated fatty acids in phosphatidylcholine to bromohydrins.

Support for the idea that MPO oxidation of lipids increases atherosclerosis comes from studies showing that chlorofatty aldehydes and chlorohydrins are present in human atherosclerotic lesions and even in infarcted myocardium in rats subjected to experimentally-induced acute myocardial infarction. Both chlorofatty aldehydes and chlorohydrins have been shown to increase COX-2 expression in endothelial cells, apoptosis in U937 cells, leukocyte adhesion, and red cell hemolysis. Taken together these reports provide strong support for the idea that MPO-dependent oxidation of lipids and lipoproteins results in the formation of toxic products that are capable of inducing atherogenic mechanisms. Indeed, some of the earliest evidence that MPO increases cardiovascular disease comes from studies showing that chlorotyrosine (ClTyr) on LDL is increased in human vascular lesions. More recently, several groups have suggested that MPO oxidation of HDL may also increase atherosclerosis. With such growing evidence that MPO-induced lipid oxidation may play a causal role in many diseases, it is essential that we develop agents that can be used to inhibit oxidation of lipids/lipoproteins as suggested to facilitate sorting out the mechanisms by which MPO increases vascular disease.

A variety of different approaches have been used to inhibit MPO-mediated cell injury: antioxidant scavenging of MPO oxidants/radicals; inhibiting $H_2O_2$ production in vivo; and, directly inhibiting MPO activity. Antioxidant scavenging of MPO oxidants and free radicals turned out to be an ineffective approach because the reaction between MPO oxidants (i.e., HOCl, HOBr) and antioxidants was not fast enough to prevent tissue damage. Inhibiting cell injury by MPO via blocking $H_2O_2$ production in vivo was also considered impractical because multiple pathways exist for generating $H_2O_2$ and none of the agents were able to block $H_2O_2$ from all sources. There are several reasons for why few inhibitors for MPO exist that are suitable for therapy. Although suicide inhibitors (i.e., azides, hydrazides and hydroxamic acids) that irreversibly modify the iron heme site of MPO, are highly effective for inhibiting enzyme activity in vitro, they lack specificity and are inherently toxic, which makes them undesirable as therapeutic agents. Several indole derivatives have been used as reversible inhibitors of MPO because they effectively compete with Cl— and SCN— to prevent Compound I from generating HOCl and HOSCN. However, during oxidation, these agents are converted into radicals that are toxic and capable of increasing oxidative stress in vivo. Phenolic compounds have also been used to inhibit MPO because they compete with the other substrates for both compound I and II. However, MPO oxidization of phenolic compounds also results in the formation of toxic radicals that can increase oxidative stress. For example, MPO has been shown to oxidize several phenolic compounds into radicals that actually accelerate LDL oxidation. Accordingly, although a significant amount of effort has gone into designing and testing agents that block MPO activity, effective MPO inhibitors remain lacking.

It is well-known that MPO oxidizes the phenol side-chain of tyrosine in small peptides (2-6 amino acids) directly and it generates oxidants that oxidize large proteins to form nitrotyrosine and/or dityrosine (DiTyr) adducts. Here, we explored the possibility of using novel tripeptides containing both Tyr and cysteine (Cys) as MPO inhibitors, whereby a Tyr. formed by MPO activity is scavenged by the thiol of the adjacent Cys. In this way the ability of Tyr. to leave the active site and oxidize LDL and/or induce cytotoxicity is essentially eliminated. Our studies show that KYC inhibits MPO-dependent HOCl, protein nitration and LDL oxidation; that the inhibition is specific for MPO; that KYC induces little if any cytotoxicity and is highly effective at protecting cells from MPO-induced injury.

Materials: MPO and LDL were from Lee Biosolutions (St. Louis, Mo.). Catalase, superoxide dismutase and rabbit anti-NO2Tyr polyclonal antibody were from EMD (Gibbstown, N.J.). MPO antibody was from Calbiochem (Cambridge, Mass.). KYC and other tripeptide analogs were either synthesized by the peptide core laboratory of the BloodCenter (Milwaukee, Wis.) or Biomatik (Wilmington, Del.). All other chemicals and reagents were from Sigma-Aldrich (St. Louis, Mo.). Purity (>98%) and authenticity of the tripeptides were confirmed by HPLC analysis and mass spectrometry. HL-60 (human promyelocytic leukemia cells) cells were from American Type Culture Collection (ATCC) (Manassas, Va.).

BAEC were obtained and maintained as previously described. The homogeneous caspase assay kit (catalog No. 03005372001) was from Roche (Indianapolis, Ind.). Celliter 96 Aqueous one solution cell proliferation assay kit (Catalog No. G3580) and Mitochondrial ToxGlo™ assay kit (Catalog No. G8000) were from Promega (Madison, Wis.).

MPO-catalyzed HOCl Production: MPO (20 nM) was incubated with $H_2O_2$ (50 μM), NaCl (150 mM), taurine (5 mM) and increasing concentrations of KYC in a phosphate buffer (100 mM, pH 7.4) containing diethylene triamine pentaacetic acid (DTPA, 100 μM) to prevent non-specific, divalent metal cation oxidation for 30 min. Reactions were halted by addition of catalase (2,000 units/mL). Chlorotaurine was quantified using the TMB assay (66). Briefly, 400 μL of reaction solution was mixed with 100 μL of 2 mM TMB, 100 μM NaI containing 10% dimethylformamide (DMF) in 400 mM acetate buffer (pH 5.4). After 5 min, absorbance (650 nm) was recorded on a UV/Vis spectrophotometer (Agilent Model 8453).

MPO-mediated Nitration of Bovine Serum Albumin (BSA): BSA (0.5 mg/mL) was incubated with MPO (20 nM), $H_2O_2$ (25 μM), $NaNO_2$ (50 μM) and increasing concentrations of KYC in phosphate buffer (100 mM, pH 7.4) containing DTPA (100 μM) for 30 min. Reactions were halted by addition of catalase (2,000 units/mL). $NO_2Tyr$ formation was assessed by western blot analysis with an anti-$NO_2Tyr$ rabbit polyclonal antibody (EMD, Gibbstown, N.J.).

MPO-mediated LDL Conjugated Diene Formation: Reaction mixtures contained LDL (0.15 mg/mL), $NaNO_2$ (100 μM), $H_2O_2$ (100 μM), MPO (20 nM) and increasing concentrations of KYC or equimolar concentrations of various compounds in a phosphate buffer (100 mM, pH 7.4) containing DTPA (100 μM). Rates of LDL conjugated diene formation were determined by following changes in absorbance at 234 nm, the wavelength maximum for conjugated dienes, on a UV-Vis spectrophotometer (Agilent Model 8453) at room temperature.

MPO-mediated LDL Malondialdehyde (MDA) Formation: Reaction mixtures contained LDL (0.5 mg/mL), $NaNO_2$ (50 μM), $H_2O_2$ (50 μM), MPO (50 nM) and increasing concentrations of KYC in a phosphate buffer (100 mM, pH 7.4) containing DTPA (100 μM). After incubation at 37° C. for 4 h, the reactions were stopped by addition of catalase (2,000 units/mL). The formation of MDA was determined according to a published procedure. Briefly, incubation mixtures (containing 25 mM BHT) were adjusted to pH 1.5 and incubated at 60° C. for 80 min to hydrolyze the Schiff Bases formed from MDA and protein. The samples were mixed with 3-fold volume of N-methyl-2-phenylindole (13.4 mM in acetonitrile/methanol (3:1)). After centrifugation (13000 g, 5 min) 330 μL of the supernatants were mixed with 57.5 μL of concentrated HCl and incubated at 45° C. for another 60 min. Finally, after centrifugation (13000 g, 5 min), total MDA in the samples was determined from the absorbance at 586 nm using a UV-Vis spectrophotometer (Agilent Model 8453).

MPO-mediated LDL Trp Oxidation: Reaction mixtures containing LDL (0.15 mg/mL), $NaNO_2$ (100 μM), $H_2O_2$ (100 μM), MPO (20 nM) and increasing concentrations of KYC in a phosphate buffer (100 mM, pH 7.4) containing DTPA (100 μM) were incubated at room temperature for 30 min. Reactions were stopped by addition of catalase (2,000 units/mL) and the oxidation of Trp in LDL was determined by measuring changes in the intrinsic fluorescence of Trp (Ex 294 nm/Em 345 nm) using a LC-50 fluorometer (Perkin Elmer, Waltham Mass.).

MPO-mediated Nitration of LDL: LDL (0.5 mg/mL) was incubated with MPO (50 nM), $H_2O_2$ (50 μM), $NaNO_2$ (50 μM) and increasing concentrations of KYC in phosphate buffer (100 mM, pH 7.4) containing DTPA (100 μM) at 37° C. for 4 h. Reactions were stopped by addition of catalase (2,000 units/mL). Formation of $NO_2Tyr$ was assessed by dot blot analysis. Briefly, LDL solutions were mixed with 1% SDS and centrifuged (12000 g, 15 min) Aliquots of supernatants were applied to a nitrocellulose membrane with a dot blot apparatus (Biorad model: Bio-Dot). The levels of $NO_2Tyr$ were visualized using a rabbit polyclonal anti-$NO_2Tyr$ antibody (EMD, Gibbstown, N.J.) and the ECL plus kit from Thermo-Peirce (Rockford, Ill.).

HPLC Analysis: KYC oxidation products were analyzed by reverse phase HPLC using a C-18 column (4.6×150 mm) The peptide and products were eluted using an acetonitrile gradient (5-10%, containing 0.1% trifluoroacetic acid) for 20 min. Elution was monitored at both 220 nm and 280 nm. N-acetyl Lysyltyrosylcyeteine amide (KYS) and N-acetyl Lysylphenylalanylcysteine amid (KFC) were analyzed on a C-18 column (2.2×150 mm) and eluted with an acetonitrile gradient (5-30%, containing 0.1% trifluoroacetic acid) for 25 min.

Cytotoxicity Assays. BAEC (passage 4-10) were seeded onto 96 well plates and cultured in MEM medium containing 10% FBS in a 5% $CO_2$ and 100% humidity environment at 37° C. Increasing concentrations of KYC (0 to 4000 μM final concentrations) were added to the cultural medium and cells were incubated for another 24 h. The effects of KYC on cell viability were determined by the MTS assay (Celliter 96 Aqueous one solution cell proliferation assay kit, Promega). Caspase activities for apoptosis in the treated BAEC were measured with the homogeneous caspase assay kit from Roche. Necrosis and mitochondrial functions were analyzed by Mitochondrial ToxGlo™ assay kit (Promega, Madison, Wis.). All determinations were performed according to manufacturer's instructions.

Phorbol 12-myristate 13-acetate (PMA)-induced HOCl Formation by HL-60 cells: HL-60 cells were cultured in RPMI 1640 medium containing 10% FBS (passage 20-50). Cells were harvested by centrifugation (1000 rpm, 10 min) and washed twice with Dulbecco's phosphate buffered saline (DPBS) with glucose. HL-60 cells ($1.2 \times 10^7$/ml) were re-suspended in DPBS with glucose. The washed HL-60 cells were either stimulated with PMA (10 μM) or not, and incubated with taurine (5 mM) and increasing concentrations of KYC at 37° C. for 30 min. Catalase (2,000 units/mL) was added to halt the reaction. After centrifugation, the supernatants were analyzed using the TMB assay as previously described.

PMA-stimulated HL-60 cell $O_2^-$ Formation: HL-60 cells were harvested by centrifugation (1000 rpm, 10 min), washed twice with DPBS with glucose to remove culture medium. The HL-60 cells ($1.2 \times 10^7$/ml) were re-suspended in DPBS with glucose. After stimulation with PMA (10 μM), the HL-60 cells were incubated with cytochrome C (40 μM) with or without superoxide dismutase (500 units/mL) at 37° C. for 10 min and then the HL-60 cells were removed by centrifugation. Cytochrome C reduction in supernatants was measured at 550 nm using a UV-Vis spectrophotometer (Agilent, Model 8453).

MPO-mediated BAEC Injury: BAEC (passage 6-8) were cultured in 24 well plates in DMEM containing 10% FBS until 70-80% confluent. The cells were washed with Hank's balanced salt solution (HBSS) 3 times and incubated with MPO (2.5 μg/mL) and $H_2O_2$±KYC at the concentrations indicated in HBSS for 30 min. Finally, BAEC were examined visually and images captured for permanent record using a Nikon Eclipse microscope (Model TS 100) fitted with a Nikon Digital Sight DS-U2 camera and NIS-Elements F 3.0 imaging software. Images are representative of 3 independent experiments.

Statistics. Data are presented as mean±SD unless stated otherwise and analyzed with the student's t-test where appropriate using Prism 5.0 (Graph Pad, Inc).

Figure 14:
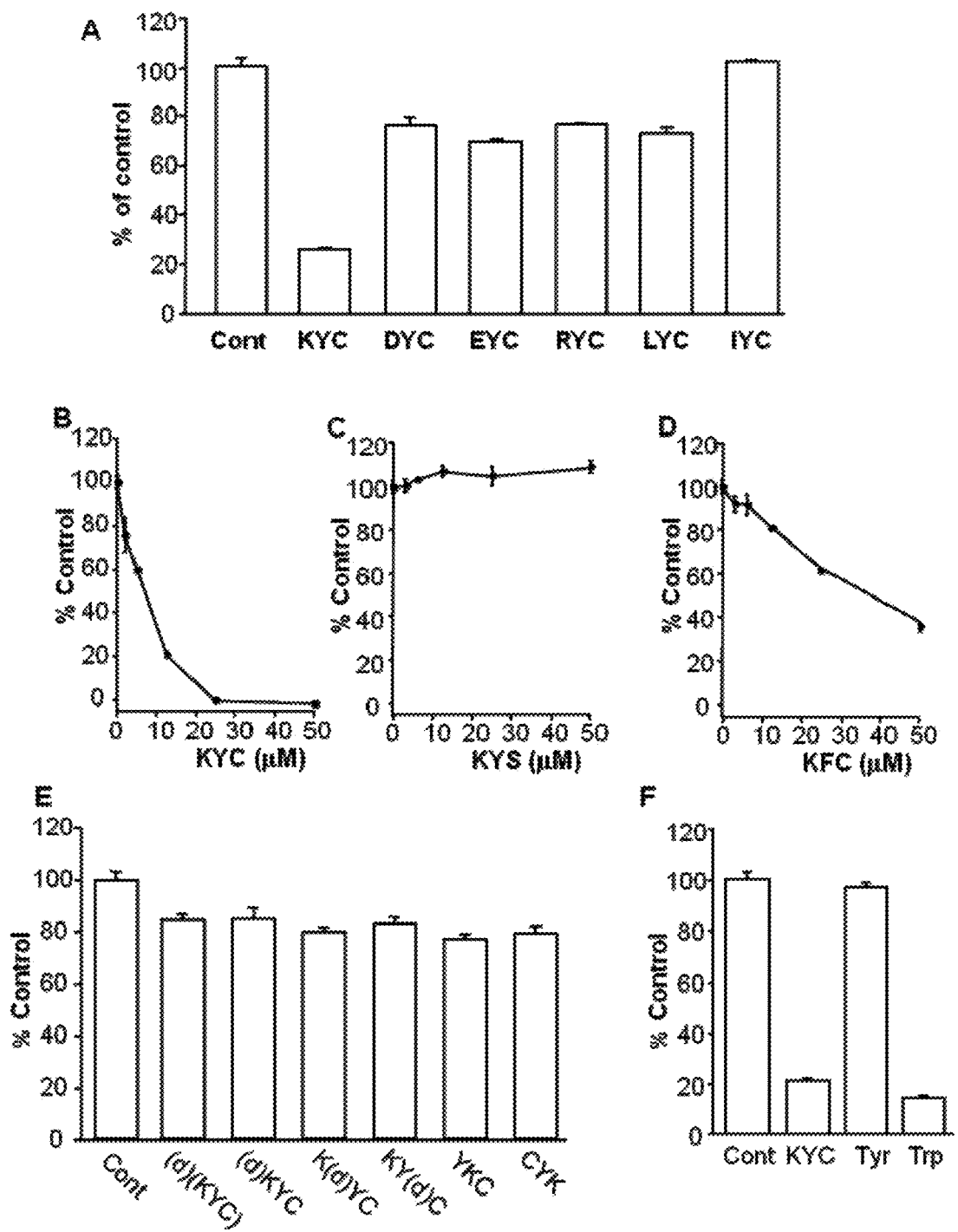
FIG. 14. Effects of Tyr and Cys containing tripeptide on MPO-catalyzed HOCl formation. MPO (20 nM) was incubated with $H_2O_2$ (50 μM), NaCl (150 mM), taurine (5 mM) and various amount of tripeptides in a phosphate buffer (100 mM, pH 7.4) containing DTPA (100 μM) for 30 min. Reactions were halted by addition of catalase (2,000 units/mL). Taurine chloroamine was quantified using the TMB assay.

Effects of Tripeptides on MPO-catalyzed HOCl Production. To determine the extent to which tripeptides inhibit MPO activity, we synthesized a series of 6 tripeptides containing Tyr and Cys (XYC) and studied their effects on MPO HOCl generation. As shown in FIG. 14A, at 12.5 µM, among the tripeptides tested, KYC was the only tripeptide that reduced HOCl production by ~75%. The other tripeptides inhibited HOCl production by (~27% to ~0%). These data indicate that KYC is the most efficient in this series of tripeptides for inhibiting MPO. KYC's ability to inhibit MPO is comparable to the inhibition reported for Trp. Interestingly, when Arg, another positively charged amino acid, was substituted for Lys the ability of RYC to inhibit MPO-catalyzed HOCl production was markedly reduced (KYC=~75% vs. RYC=~22% inhibition). These data indicate that the charge, size and hydrophobicity of the first amino acid are important to how tripeptides inhibit MPO activity.

To further determine the inhibition efficiency by which KYC inhibits MPO, we next determined dose-dependent effects of KYC on MPO-catalyzed HOCl production. FIG. 14B shows that KYC dose-dependently inhibited HOCl production with an IC50 of ~7 µM (FIG. 14B). At 25 µM, KYC completely inhibited HOCl production.

To understand the importance of the phenol of tyrosine and the thiol of cysteine for KYC inhibiting MPO, we compared the dose-dependent effects of KYC with two structural analogues, KFC and KYS. Without a free thiol, KYS failed to inhibit MPO-catalyzed HOCl production (FIG. 14C). In contrast, without a phenol group, KFC was a weaker inhibitor of HOCl formation as detected by the taurine/TMB assay than KYC (FIG. 14D). While KYC (25 µM) completely ablated MPO-catalyzed HOCl production, KFC (25 µM) reduced HOCl detected by the taurine/TMB assay by only 35% (FIG. 14D). As both Phe and Cys are poor substrates for MPO and there is almost no direct oxidation by MPO, KFC's mechanism of action has more to do with the free thiol scavenging of HOCl or taurine chloroamine in the assay mixture than with actually entering the active site of MPO to scavenge compound I or II in the same way as KYC. These data show that while Tyr and Cys are required for KYC to effectively inhibit MPO Lys also plays a critical role in orienting the tripeptide for optimal inhibition.

To investigate the effect of D-isomers and sequence isomers of KYC on MPO inhibition, we compared the effects of KYC, made with all L-amino acids, with the effects of D-amino acids and sequence isomers of KYC on MPO-catalyzed HOCl production. FIG. 14E shows that replacing an L-amino acid with a D-amino acid at any position or even at all three positions in KYC, dramatically decreased the ability of the tripeptide to inhibit MPO-catalyzed HOCl production. Likewise, YKC and CYK failed to inhibit MPO-catalyzed HOCl production to the same extent as KYC (all L-amino acids). Finally, we compared the effects of KYC on MPO-catalyzed HOCl production to the effects of free Tyr and Trp (FIG. 14F). Consistent with another report Trp was an effective inhibitor of MPO-catalyzed HOCl production. In contrast, Tyr alone had little, if any effect, on MPO-catalyzed HOCl production as has been reported. The lack of effect of Tyr on MPO activity is also in agreement with our studies showing that KYS, which contains a single Tyr, was not an inhibitor of MPO-catalyzed HOCl production. These data indicate that KYC's sequence is unique and that steric conformation and sequence order of the tripeptide are important structural requirements for KYC to inhibit MPO.

Figure 15:
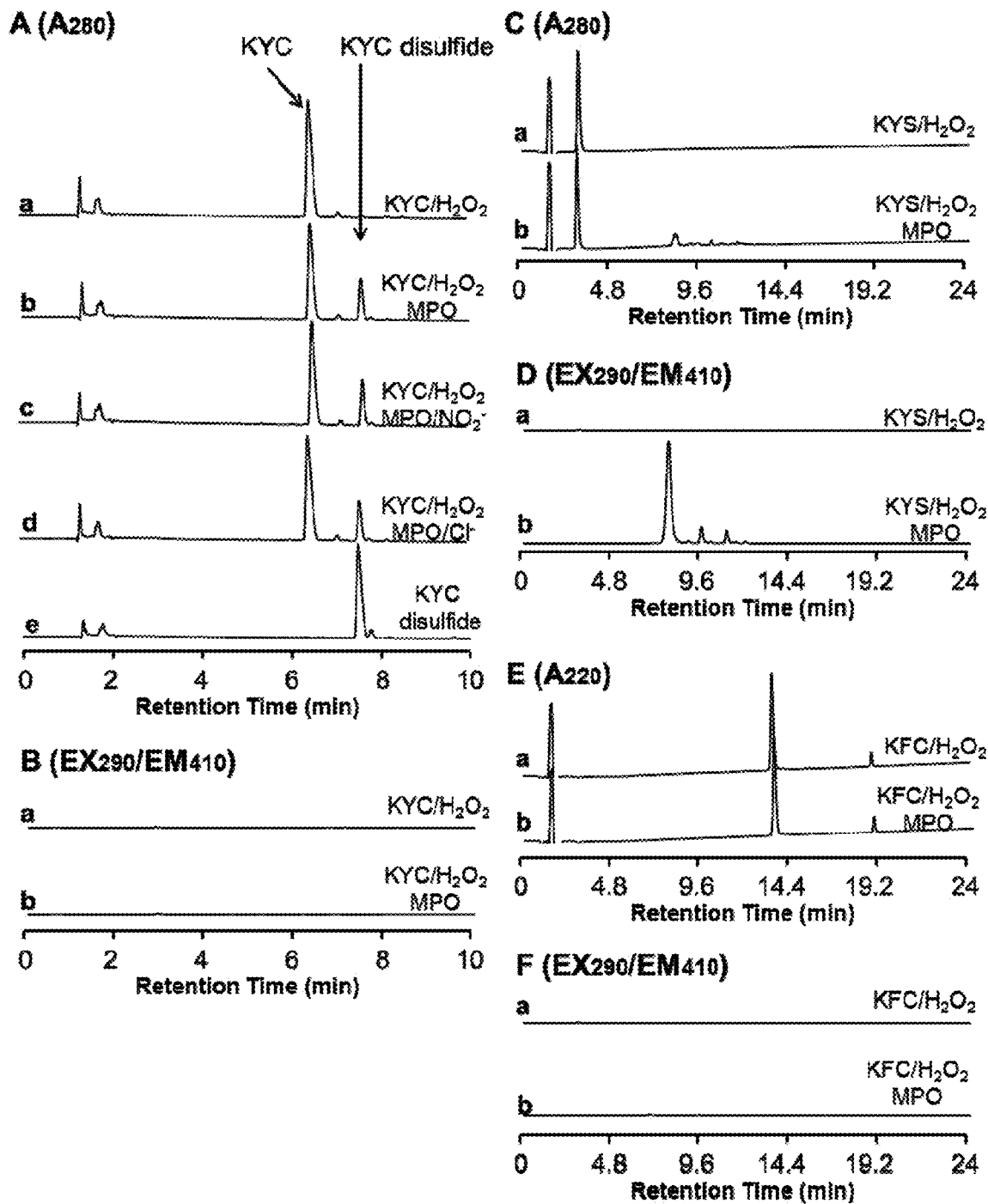
FIG. 15. HPLC analysis of MPO-mediated KYC Products Formation.

MPO catalyzed KYC Oxidation Product Analysis. To determine how MPO activity oxidizes KYC, we analyzed reaction products by HPLC. MPO/$H_2O_2$ systems oxidized KYC essentially to a single product that eluted around 7.6 min (FIG. 15A, trace b). Although KYC can be oxidized by $H_2O_2$ directly, incubations with $H_2O_2$ alone yielded very little of the 7.6 min product (FIG. 15A, trace a), which has the same retention time as authentic KYC disulfide (FIG. 15A, trace e). Monitoring the eluate from the HPLC with a fluorescent detector (Ex=290 nm/Em=410 nm), the fluorescence characteristic of a dityrosine (DiTyr), showed no significant peak formation (FIG. 15B, trace a and b). This lack of fluorescence rules out DiTyr as a major product of oxidation. When KYS is oxidized with the MPO/$H_2O_2$ system several products were observed to elute between 7-10 min (FIG. 15C, trace a and b). The major peak in this trace has a fluorescent profile that is characteristic of DiTyr (FIG. 15D, trace b), suggesting that, unlike KYC, Tyr in KYS was oxidized by MPO to form Tyr., which in turn, forms DiTyr. Incubation of KFC, another KYC analog, with the MPO/$H_2O_2$ system did not yield MPO-dependent oxidation products (FIGS. 15E and 15F), although small amounts of disulfides did seem to form, likely a result of slow oxidation of the thiols by $H_2O_2$. Such data clearly indicate that, although MPO was able to oxidize Tyr in both KYC and KYS directly, KYS formed DiTyr products from the Tyr. radical, whereas the Cys in KYC rapidly scavenged the Tyr. radical leading to the formation of a disulfide instead of DiTyr. Analysis of products from the MPO/$H_2O_2$/$NO_2^-$ system (FIG. 15A, trace c) or the MPO/$H_2O_2$/$Cl^-$ system (FIG. 15A, trace d) showed that KYC disulfide was also the major oxidation product of these systems. These data suggest that regardless of the conditions under which MPO oxidizes KYC, in the presence of $NO_2^-$ or $Cl^-$, the major oxidation product is KYC disulfide, not DiTyr. Such findings clearly indicate that MPO directly oxidizes the Tyr in the tripeptides, which can only be accomplished if KYC enters the active site of MPO to generate a Tyr. radical that is subsequently detoxified by the free thiol of Cys with high efficiency.

Figure 16:
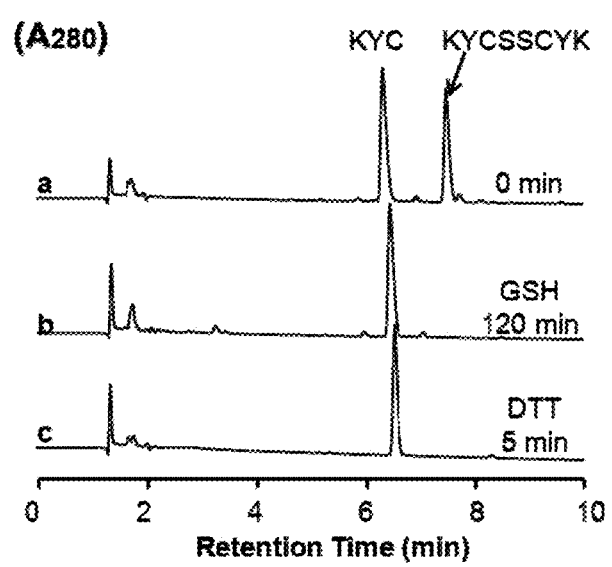
FIG. 16. Thiol Reduction of KYC disulfide. Trace A. KYC (440 μM) was mixed with MPO (50 nM) and $H_2O_2$ (100 μM) for 2 hr as in (FIG. 16, Panel A, Trace B) and reaction products analyzed by HPLC. Trace B. An aliquot (50 μL) of the reaction mixture in Trace A was mixed with 10 mM GSH (50 μL) for 120 min and resulted products were analyzed by HPLC. Trace C. An aliquot (50 μL) of the reaction mixture in Trace A was mixed with 50 μL of DTT (0.5 mM) for 5 min at room temperature and products analyzed by HPLC.

To confirm that KYC oxidation by MPO yields a simple disulfide, we reduced the product using simple thiols such as glutathione (GSH) and dithiothreitol (DTT). FIG. 16 (trace b and c) shows that when KYC disulfide was incubated with GSH the KYC disulfide is completely reduced to its KYC monomer (FIG. 16, trace b). More so, DTT completely reduced KYC disulfide to its KYC monomer within 5 min (FIG. 16, trace c). These data demonstrate that oxidation of KYC results in the formation of simple disulfides that can be easily regenerated to its active monomeric form with physiologically relevant concentrations of GSH.

Figure 17:
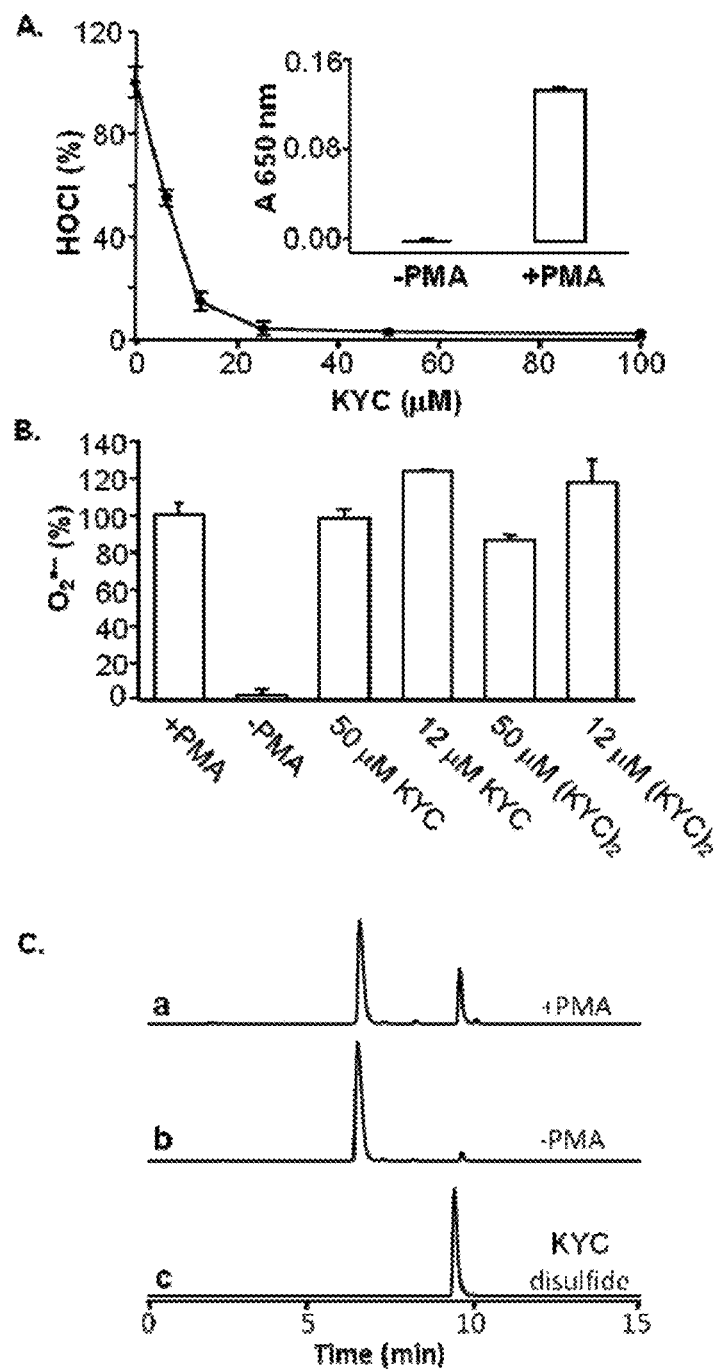
FIG. 17A. KYC inhibited HOCl formation. HL-60 cells ($1.2 \times 10^7$/ml) were incubated with PMA and taurine as described in methods. The reaction was stopped by catalase. After centrifugation, chlorotaurine was quantified by the KI/TMB assay. Inset this panel shows that PMA is required to stimulate HL-60 cell HOCl production.
FIG. 17B. Effects of KYC, and KYC disulfide on HL-60 cell $O_2^-$ Production. $O_2^-$ formation was analyzed by the SOD-inhibitable cytochrome C reduction assay. HL-60 cells were incubated with Cytochrome C (40 μM) with or without superoxide dismutase at 37° C. for 10 min. The reaction was stopped by addition of catalase. After centrifugation, Cytochrome C reduction was determined at 550 nm using a UV-Vis spectrophotometer. Results are expressed as % of control, the data represents mean±SD (n=3).
FIG. 17C. Effects of PMA on HL-60 cell Product Formation. HL-60 cells were stimulated with PMA (37° C. for 30 min) and then incubated with KYC as above in Panel A. KYC oxidation products were analyzed by HPLC. Trace a. Incubation with PMA-stimulated HL-60 cells. Trace b. Incubation with non-stimulated HL-60 cells. Trace c. KYC disulfide standard.

KYC Specifically Inhibits MPO in HL-60 Cells. HL-60 cells were stimulated with PMA to release MPO and then treated with KYC to determine its effects on HL-60 cell HOCl production. Without PMA stimulation, HL-60 cells produced little, if any HOCl (FIG. 17A inset). However, after PMA stimulation, HL-60 cells generated high levels of HOCl (FIG. 17A, inset). KYC dose-dependently inhibited HOCl production by PMA-stimulated HL-60 cells with an $IC_{50}$~7 µM (FIG. 17A). MPO-mediated HOCl formation also requires $H_2O_2$ that is derived from $O_2.^-$ generated by NADPH oxidase (NOX). To determine whether KYC or KYC disulfide inhibited NOX $O_2.^-$ generation in HL-60 cells, which could also yield results that would make it appear as if KYC were directly inhibiting MPO-dependent HOCl production, we quantified $O_2.^-$ production using the Cytochrome C assay.

Neither KYC nor KYC disulfide had any significant effect on $O_2.^-$ production in PMA-stimulated HL-60 cells (FIG. 17B). HPLC analysis of the oxidation products revealed that KYC disulfide was the major product from PMA-stimulated HL-60 cells (FIG. 17C). Taken together, these data suggest that KYC inhibited MPO but not NOX activity and that KYC disulfide is the major oxidation product of activated HL-60 cells incubated with KYC.

Figure 18:
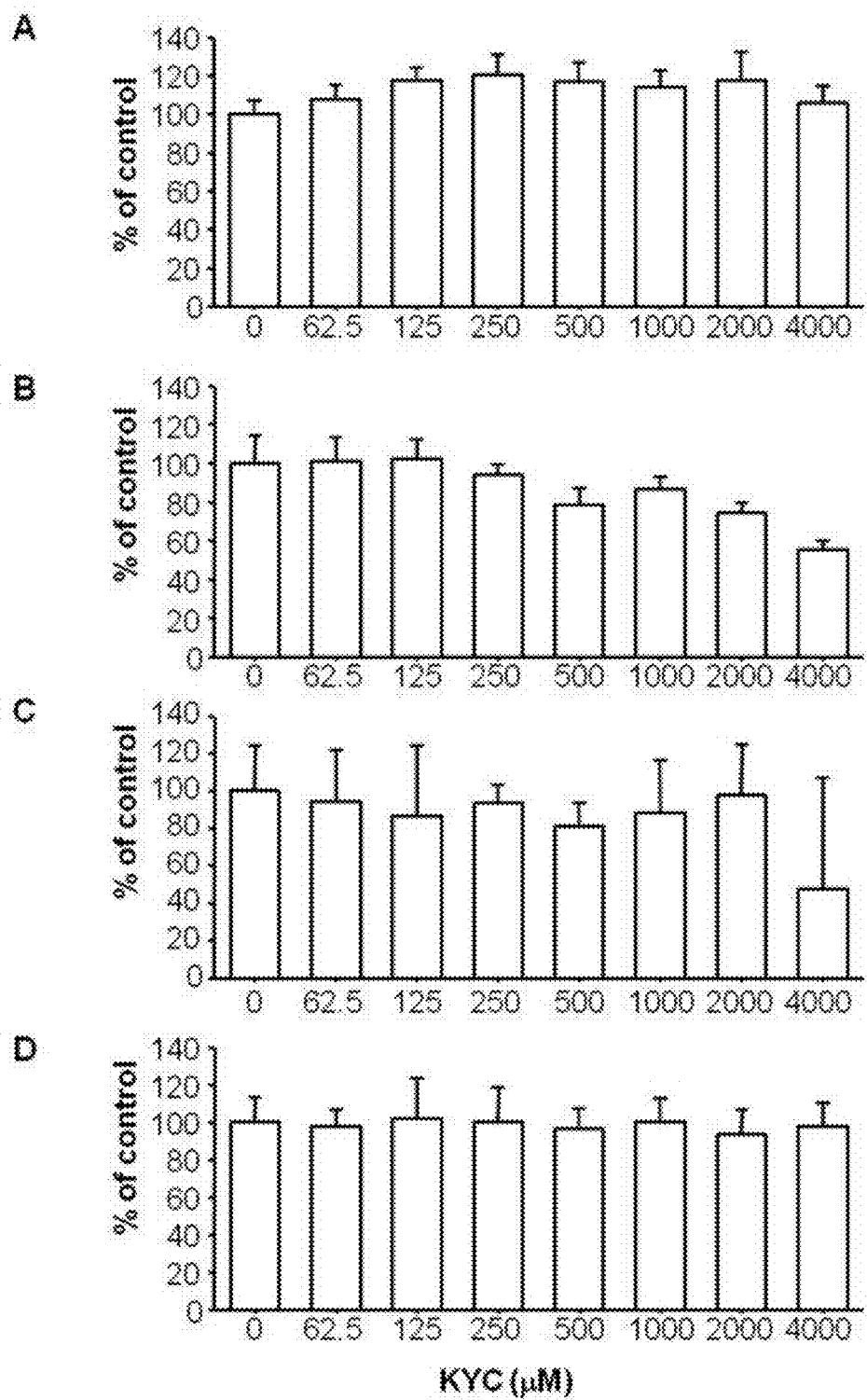
FIG. 18. The toxicity effect of KYC on BAEC culture. Various amounts of KYC were incubated with BAEC cells for 24 h. Then the Cell viability (MTS assay) (n=5) (FIG. 18A), apoptosis (caspase assay) (n=3) (FIG. 18B) necrosis (protease assay) (n=3) (FIG. 18C) and mitochondrial function (ATP assay) (n=3) (FIG. 18D) were analyzed according to manufactury instructions.

Cytotoxicity of KYC on BAEC. As a first step towards determining whether KYC is suitable for in vivo treatments, we incubated BAEC cultures with increasing KYC concentrations (0-4000 µM). After 24 hours, we analyzed the impact of KYC on cell viability, apoptosis, necrosis and mitochondria function. FIG. 18A shows the effects of KYC on BAEC viability as determined by MTS assay. No significant increases in cell death were induced by KYC even at 4000 µM. Likewise, caspase activity was essentially unaltered in BAEC cultures in increasing KYC concentrations (FIG. 18B). These data indicate that KYC does not induce apoptosis. Membrane integrity studies show that KYC had no effects on protease activity, an index for necrosis, in BAEC after 24 hours (FIG. 18C). Finally, cellular ATP, an index of mitochondrial function, was unaltered in BAEC cultures by incubation with KYC (FIG. 18D). On the basis of data from these limited studies we conclude that KYC does not induce cell damage even at concentrations up to 4000 µM. These data suggest that KYC will likely be safe in vivo and may be useful as a therapeutic agent to target aberrant MPO activity in a variety of different diseases.

Figure 19:
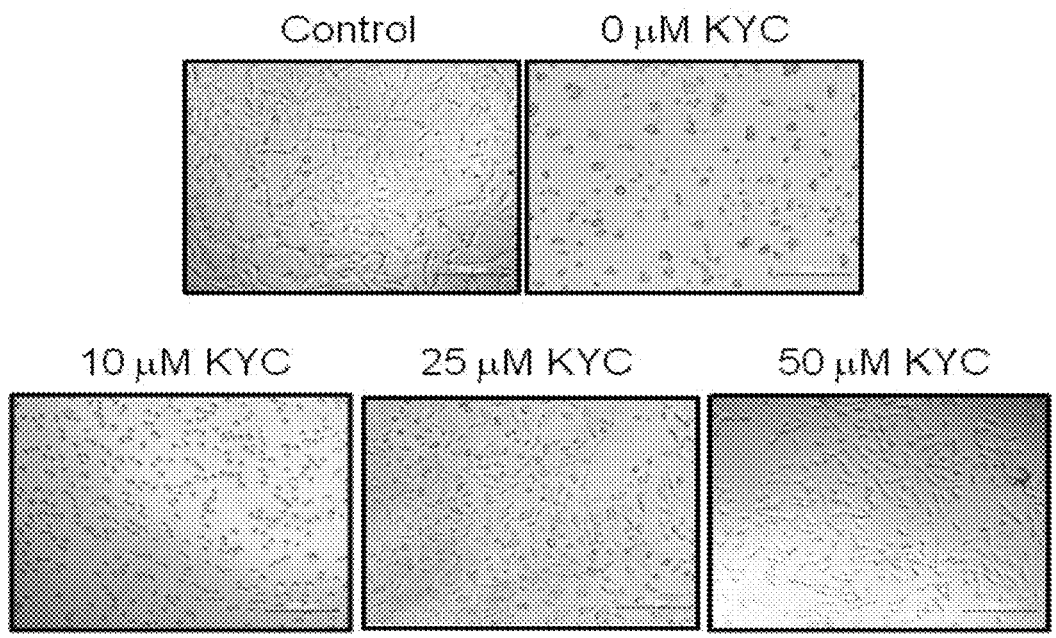
FIG. 19. The protection of BAEC by KYC from MPO induced injury. Bovine aortic endothelial cells (BAEC) (passage 6-8) were cultured in a 96 well plate with DMEM and 10% FBS until 70-80% confluent and then treated with MPO, $H_2O_2$ and KYC as described in Methods. Images here are representative of 3 independent studies. The figure shows KYC concentration dependent protection against MPO.

KYC protects BAEC from MPO-induced injury. With data indicating that KYC is not toxic to BAEC, we next determined if KYC could protect BAEC from MPO-induced injury. BAEC in 96 well were treated with 100 µl of HBSS containing MPO (2.5 µg/ml) and $H_2O_2$ (50 µM) for 20 min with or without KYC. Changes in cell morphology were recorded as described in a previous report by others. FIG. 19 shows that KYC dramatically increased BAEC viability and survival. Incubation of BAEC in the MPO/$H_2O_2$/Cl$^-$ alone caused severe cell damage as demonstrated by dramatic changes in cell morphology (FIG. 19). KYC dose-dependently increased protection of BAEC cultures from MPO-induced injury (FIG. 19). At 50 µM KYC, BAEC cultures had almost the same morphology as cultures that were not exposed to MPO (control). KYC also protected BAEC from even higher concentrations of MPO (5 µg/ml) and $H_2O_2$ (100 µM) (BAEC was incubated with 2.5 µg MPO and 100 µM $H_2O_2$ with or without 25 µM KYC for 20 min and with 5 µg MPO and 50 µM $H_2O_2$ with or without 25 µM KYC for 20 min. The data obtained represent 3 repeats. Data not shown). This study shows that KYC is fully capable of protecting BAEC from the cytotoxic effects of MPO activity.

Figure 20:
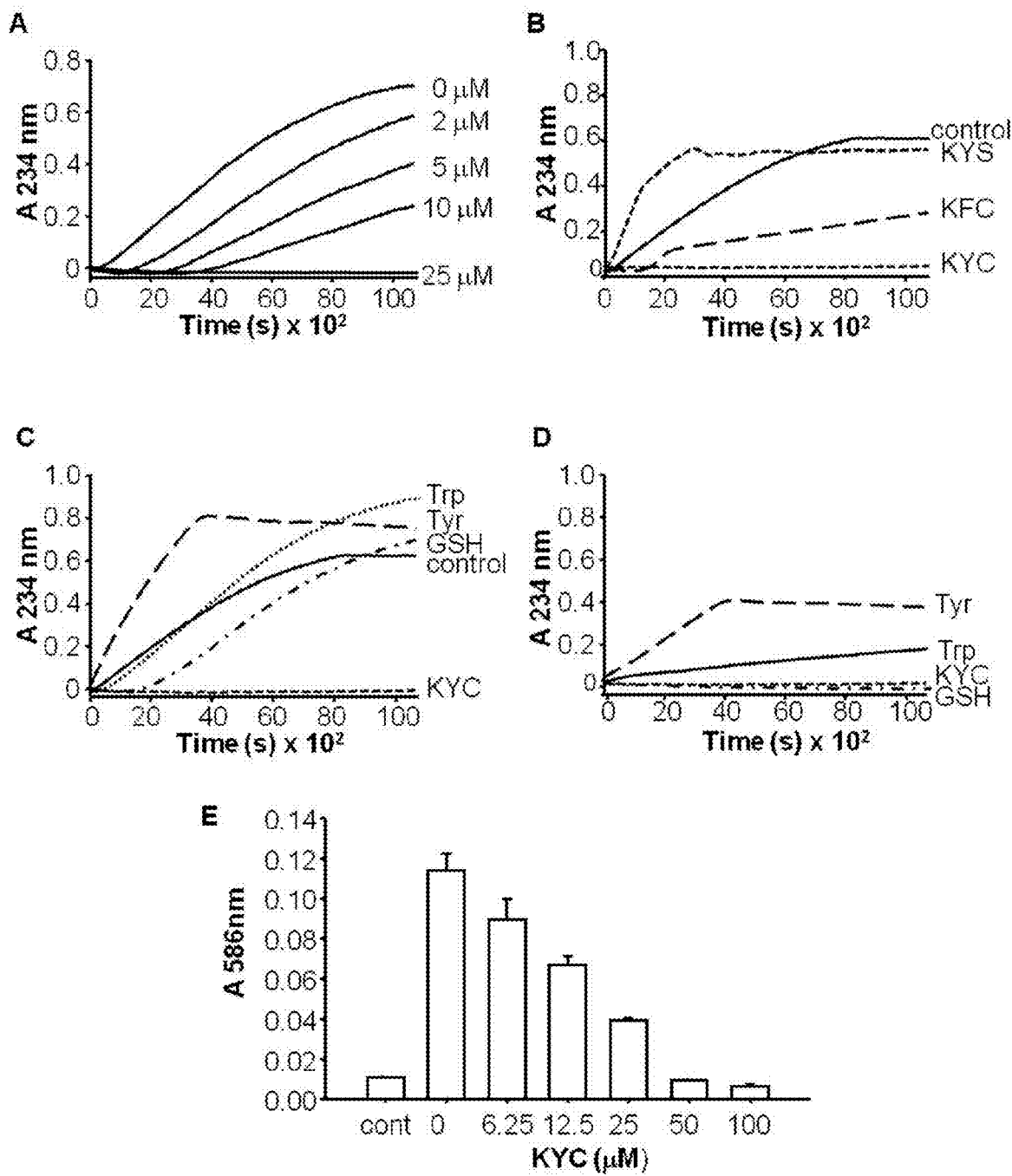
FIG. 20. Effects of KYC on MPO-mediated LDL oxidation. LDL oxidation was induced by MPO (20 nM), $H_2O_2$ (100 μM) and NaNO₂ (100 μM) in a phosphate buffer (100 mM, pH 7.4) containing DTPA (100 μM) at room temperature.

Effects of KYC on MPO-mediated LDL lipid peroxidation. MPO oxidation of LDL and HDL has been hypothesized to play causal roles in atherogenesis. To determine if KYC inhibits LDL oxidation, we incubated LDL in MPO/$H_2O_2$/$NO_2^-$ reaction systems containing increasing concentrations of KYC and measured changes in conjugated diene formation. The MPO/$H_2O_2$/$NO_2^-$ reaction system dramatically increased LDL oxidation, confirming reports that MPO oxidizes lipids by generating $.NO_2$. Adding KYC to MPO/$H_2O_2$/$NO_2^-$ reaction system dose-dependently increased the lag time and decreased the overall rate of LDL oxidation. At 25 µM, KYC completely suppressed LDL oxidation (FIG. 20A). These data demonstrate that KYC is a potent inhibitor of MPO-mediated LDL peroxidation. Next, we compared the effects of KYC with the effects of KFC and KYS (FIG. 20B). While KYC (25 µM) completely ablated LDL oxidation, KFC increased the lag phase and delayed, but did not totally inhibit LDL oxidation. We reason that KFC's limited effects on LDL oxidation were probably the result of direct $.NO_2$ scavenging via the thiol of KFC. KYS gave a totally different inhibition profile. Instead of inhibiting LDL oxidation, KYS actually accelerated LDL oxidation (FIG. 20B). In this case, the Tyr in KYS appears to enter the active site of MPO, be oxidized to generate Tyr. within KYS. As Tyr. is a strong oxidant regardless of whether it is alone or in a tripeptide, such oxidation should logically accelerate LDL oxidation. FIG. 20C shows data comparing the inhibitory potential of KYC with those of Tyr, Trp and GSH with respect to MPO-mediated LDL oxidation. In agreement with a report by others, Tyr (dash line) accelerated and enhanced LDL oxidation. Although findings by others and our data (FIG. 14F) show that that Trp effectively inhibited MPO-catalyzed HOCl production, adding Trp to MPO/$H_2O_2$/$NO_2^-$ reaction system did not inhibit but actually enhanced LDL oxidation (FIG. 20C). Even though initial rates of LDL oxidation in MPO/$H_2O_2$/$NO_2^-$ reaction systems were slowed by GSH (i.e., an increase in lag time), this delay was quickly lost with what appears to be an increase in thiol oxidation. Regardless, for all practical purposes GSH was ineffective for inhibiting LDL oxidation when compared with KYC.

Additional insight into the mechanisms by which KYC inhibited MPO-mediated LDL oxidation was gained by repeating the MPO/$H_2O_2$ oxidation studies in the absence of $NO_2^-$. In these studies, we observed that Tyr (FIG. 20D, dash line) and Trp (FIG. 20D, dot line) increased MPO-mediated LDL oxidation, which agrees with the fact that both Tyr. and Tyr., formed by MPO oxidation, are potent oxidants that accelerate LDL oxidation. In contrast, KYC and GSH did not increase LDL oxidation. GSH is reported to be a poor substrate for MPO/$H_2O_2$ systems whose rate of reaction is on the order of 10-100 $M^{-1}s^{-1}$. The glutathionyl radical formed is known a poor oxidant. Thus, in the presence of GSH the MPO/$H_2O_2$ system was unable to oxidize LDL. In contrast, the Tyr in KYC can be rapidly oxidized to Tyr. by MPO. The fact that the MPO/$H_2O_2$ system failed to increase LDL oxidation in the presence of KYC is consistent with the fact that the Tyr. was rapidly scavenged by the thiol of Cys via intramolecular electron-transfer.

Malondialdehyde (MDA) is another biomarker of lipid peroxidation. To determine the effects of KYC on MPO-dependent MDA formation in LDL we incubated LDL (0.5 mg/mL) in a MPO/$H_2O_2$/$NO_2$ reaction system (50 nM, 50 µM, 50 µM, respectively) and measured changes in MDA formation. Increasing concentrations of KYC dose-dependently inhibited MPO-mediated MDA formation in LDL (FIG. 20E) just as it did conjugated diene formation (FIG. 20A).

Figure 21:
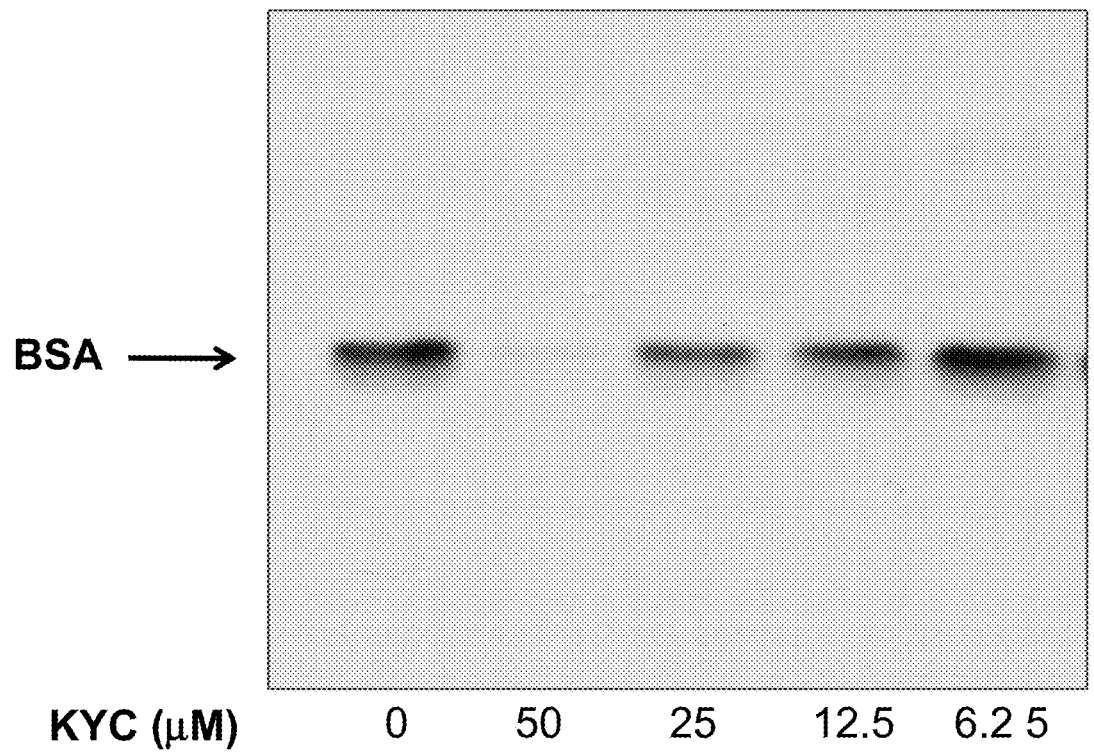
FIG. 21. Effects of KYC on MPO-mediated Protein Nitration: BSA (0.5 mg/mL) was incubated with MPO (20 nM), $H_2O_2$ (25 μM), NaNO₂ (50 μM) and increasing concentrations of KYC in phosphate buffer (100 mM, pH 7.4) containing DTPA (100 μM) for 30 min. Reactions were stopped by addition of catalase (2,000 units/mL). NO₂Tyr formation was assessed by western blot analysis. This autoradiogram shows concentration dependent effects of KYC on nitrotyrosine formation on BSA. Left-to-right. lane 1=MPO, $H_2O_2$, NaNO₂, BSA; lane 2=MPO, $H_2O_2$, NaNO₂, BSA+50 μM KYC; lane 3=MPO, $H_2O_2$, NaNO₂, BSA+25 μM KYC; lane 4=MPO, $H_2O_2$, NaNO₂, BSA+12.5 μM KYC; and, lane 5=MPO, $H_2O_2$, NaNO₂, BSA+6.25 μM KYC. Incubation conditions were as outlined in Methods. The data represent 3 repeats.

Effects of KYC on MPO-mediated Protein Nitration. MPO-catalyzed $.NO_2$ production plays important role in the mechanisms by which MPO induces cell injury. To determine if KYC decreases MPO-induced increases in nitrosative stress, we incubated BSA in a MPO/$H_2O_2$/$NO_2^-$ reaction system in the absence and presence of KYC and then measured changes in BSA nitration. The reactions were carried out in phosphate buffer containing DTPA for 30 min. $NO_2$Tyr formation in BSA was measured by western blot analysis. FIG. 21 shows that the MPO/$H_2O_2$/$NO_2$ induces marked increases in BSA-$NO_2$Tyr formation (FIG. 21, lane 1). KYC dose-dependently inhibited BSA $NO_2$Tyr formation. Compared to KYC at 0 µM, KYC at 12.5 µM inhibited $NO_2$Tyr formation by 50% (FIG. 21, lane 1 vs. 4) and essentially ablated $NO_2$Tyr formation in BSA when added at 50 µM (FIG. 21, lane 2). These results indicate that KYC is an effective inhibitor of MPO-dependent protein nitration.

Figure 22:
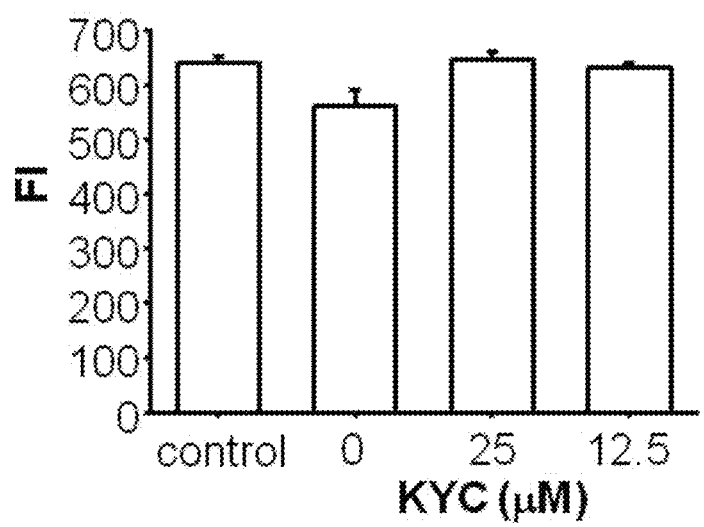
FIG. 22.B. The effect of KYC on MPO-mediated tyrosine nitration of LDL: LDL (0.5 mg/mL) MPO (50 nM), $H_2O_2$ (50 μM), NaNO₂ (50 μM) and increasing concentrations of KYC in phosphate buffer (100 mM, pH 7.4) containing DTPA (100 μM) at 37° C. for 4 h. Reactions were stopped by catalase (2,000 units/mL). The formation of NO₂Tyr was assessed by dot blot analysis. The data represent 3 repeats.
Figure 22:
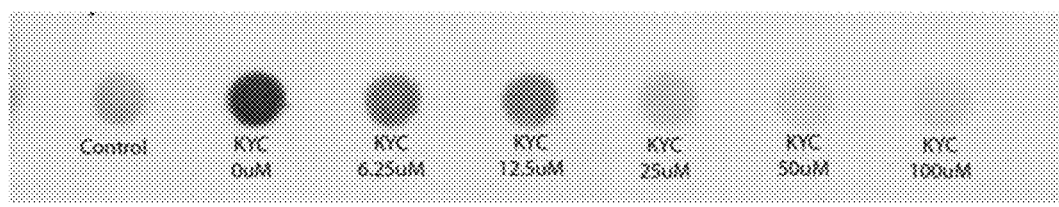

KYC Inhibits MPO-dependent LDL Protein Oxidation and Nitration. In addition to nitrating Tyr in proteins, MPO has also been shown to oxidize Trp in proteins. To determine the effects of KYC on MPO-dependent nitration and Trp oxidation of LDL we incubated LDL (0.1 mg/ml) in an MPO/$H_2O_2$/$NO_2^-$ reaction system (20 nM, 50 µM, 50 µM, respectively) for 30 min at room temperature and then measured Trp oxidation in LDL via changes in Trp intrinsic fluorescence. This MPO reaction system induced significant decreases (15%, $p<0.001$) in Trp intrinsic fluorescence in LDL (FIG. 22A), confirming that Trp in LDL was oxidized. In contrast adding KYC to the reaction system protected the Trp residues in LDL against MPO-dependent oxidation. FIG. 22B shows that KYC markedly reduces $NO_2$Tyr in LDL just as it did in the BSA studies (FIG. 21). Taken together, these data indicate that KYC is an effective inhibitor of MPO-dependent lipid peroxidation, Trp oxidation and Tyr nitration in LDL.

Discussion. This study shows, for the first time, that KYC is a novel tripeptide that inhibits MPO-dependent HOCl production, LDL lipid peroxidation, protein nitration and Trp oxidation. KYC specifically inhibits the activity of MPO released from PMA-activated HL-60 cells and not NOX activity which is responsible for HL-60 cell $O_2.^-$ generation. KYC does not induce cytotoxicity in BAEC even when used at concentrations as high as 4000 µM. Instead, KYC protects BAEC from MPO-induced injury and death when used at concentrations that are several orders of magnitude less than the highest concentration used for the cytotoxicity studies. Such characteristics suggest that KYC may have a wide therapeutic window for treating MPO-dependent vascular inflammation.

Several studies show that phenol and/or indole-like compounds are capable of competing against halides for reaction with compound I and II of MPO such they prevent the conversion of the halide to toxic hypohalous acids. Even though such agents may out-compete halides, their reaction with compound I and II of MPO results in the formation of corresponding phenolic and indole radicals that could also be toxic. To develop a new class of MPO inhibitors with less toxicity than phenolic or indole agents we synthesized a series of tripeptides that contain both Tyr and Cys. Here, we used Tyr, a natural substrate of MPO, to attempt to scavenge MPO oxidation intermediates. As anticipated, the reaction of Tyr with activated MPO resulted in the generation of a toxic Tyr. However, in the context of the tripeptide, KYC, the Tyr. seems to be scavenged before it has a chance to leave the active site of MPO and oxidize other cellular targets. Throughout the literature, there are several examples of rapid electron transfer between redox active amino acids. Rate studies show that electron transfer follows the rank order of Met>Trp>Tyr>=Cys (74-76).

Moreover, ESR spin trapping studies showed that although MPO oxidizes Tyr in small peptides (2-6 amino acids) to a Tyr., including a Cys in the peptide allowed for a rapid electron transfer, resulting in the formation of Cys. and it exclusively forms a disulfide. Previous reports showed that including a Cys in the Tyr containing peptides was an effective strategy for scavenging Tyr. and thus protecting protein Tyr from being nitrated by locally generated oxidants. Our rationale here was to incorporate Cys into the Tyr-based peptides so that when MPO extracts an electron from the Tyr to generate Tyr. this radical could be efficiently scavenged internally, before it has a chance to leave the active site of MPO to induce secondary oxidative damage. Support for internal intramolecular electron transfer playing a role in the mechanisms by which KYC detoxifies MPO comes from data in this report showing that MPO-dependent KYC oxidation forms exclusively a disulfide, not DiTyr, since DiTyr is only formed when one Tyr. condenses with another Tyr. These data including data showing that the most efficient tripeptide inhibitor is KYC made with all L-amino acids, indicates that KYC is unique in its ability to allow the Tyr to scavenge MPO oxidation intermediates and yet inactivate the toxic Tyr. before it has a chance to leave the active site to induce secondary oxidative damage.

Previous studies have shown that thiols are effective scavengers of MPO oxidation products, such as HOCl and .$NO_2$. Accordingly, it is possible that the thiol of KYC also scavenges these same oxidants in our assays. However, several lines of evidence indicate that the Tyr of KYC directly scavenges MPO compound I and II as the dominant mechanism by which it inhibits MPO. First, in agreement with previous reports MPO is able to directly oxidize Tyr in small peptides and to indirectly oxidize Tyr in large proteins. Furthermore, when KYC is oxidized by simple MPO/$H_2O_2$ reaction systems (i.e., no chloride or nitrite), it only forms a disulfide. Next, we show that MPO/$H_2O_2$ reaction systems oxidize KYS but not KFC. This indicates that Tyr, not Cys, is the favored target of activated MPO in tripeptides that contain both Tyr and Cys. Moreover, although KFC decreases HOCl levels, the previous study of the reactions between HOCl and amino acids suggests that the drop in HOCl results more from the thiol of KFC than Lys and Phe which are not effective HOCl scavengers under the condition. Finally, we compared the effects of KYC with 11 other tripeptides (including 5 tripeptides with different first amino acids, 4 stereo isomers of KYC, and 2 analogues having different sequences) on MPO-dependent HOCl production. All 11 analogues were consistently less effective than KYC as an inhibitor of MPO-catalyzed HOCl production, including the all D-isomer, Ac-(d)K(d)Y(d)C-amide, even though it should have had the same chemical properties as KYC in scavenging HOCl. Such results imply that KYC possesses a specific structure that is essential for inhibiting MPO activity that goes well beyond the fact that KYC simply contains both a Tyr and Cys.

Taken together, our data suggest that KYC inhibits MPO activity mainly via a two-step reaction mechanism. First, as mentioned above, Tyr in KYC serves as the substrate that competes with $Cl^-$ and $NO_2^-$ for compound I and II of MPO. Thus, Tyr may react with the activated iron heme of MPO in ways that prevent $Cl^-$ or $NO_2^-$ from being transformed into HOCl and $NO_2$, respectively. Secondly, internal scavenging of Tyr. in KYC prevents MPO-generated Tyr. from oxidizing other biological targets. By placing Cys in close proximity to Tyr in KYC, when highly reactive Tyr. radicals are formed by MPO, it is rapidly scavenged by the thiol of Cys to form a less reactive Cys. Finally, when KYC is present in sufficient concentrations or when GSH is present the Cys. can be scavenged to form a simple disulfide or mixed disulfide.

As our primary objective was to develop an effective inhibitor of MPO activity that was not toxic, it was encouraging to see that BAEC could be incubated in KYC at high concentrations (4000 µM) without any significant effects on BAEC viability, apoptosis, necrosis or mitochondrial function. This is important because even though other agents are reported to effectively inhibit MPO activity in vitro, their toxic side effects reduced their usefulness in vivo. For example, large doses of melatonin have been used to improve vasodilatation in hypertensive rats. However, when melatonin was used at these concentrations, it increased the number of apoptotic cells in the vessel wall of the hypertensive rats. Likewise, when cholesterol-fed rabbits were treated with 4-aminobenzoic acid hydrazide, which is highly effective for inhibiting MPO activity in vitro, the treatments actually increased intimal hyperplasia by over 43%. Such a result is opposite to that which is required for treating vascular disease. Our studies show that KYC is not toxic to cultured BAEC and that it is highly effective for protecting BAEC from the harmful effects of MPO.

In addition to increasing specificity and avoiding toxicity, hydrophobicity is another important chemical characteristic of MPO inhibitors that may be essential for effective use in vivo. In a previous report, it was shown that although an MPO inhibitor was highly effective for inhibiting MPO in vitro, it still failed to prevent LDL oxidation, potentially due to hydrophobicity. Although 4-aminobenzoic acid hydrazide is an effective inhibitor of MPO in vitro, it was rapidly taken up by the LDL particle because it is also highly soluble in lipids, which effectively reduced its access to MPO in aqueous environments. In KYC, Lys, a positively charged amino acid, makes the tripeptide hydrophilic, thus preventing its diffusion into the lipid domain of LDL while at the same time increasing its solubility in water. Such increases in hydrophilicity should improve KYC's retention in hydrophilic environments in vivo (i.e., blood stream, matrix, and subendothelial spaces) where MPO is known to exist and induce tissue damage. Our data showed that KYC effectively inhibits MPO-mediated LDL lipid peroxidation and protein oxidation/nitration. These data indicate that KYC may be a more suitable inhibitor of MPO in lipid rich regions than agents that possess a more hydrophobic character such as 4-aminobenzoic acid hydrazide.

In conclusion, KYC, a novel tripeptide, is a specific, potent, non-toxic inhibitor of MPO activity that may be suitable for in vivo studies. As KYC effectively inhibits MPO activity to prevent HOCl formation, inhibit LDL oxidation and protect BAEC from MPO-mediated cytotoxicity, KYC may be an effective inhibitor for investigating MPO-dependent mechanisms of oxidative/nitrosative stress in a variety of diseases. The principles explained here concerning the chemistry by which KYC inhibits MPO activity may lead to the development of new therapeutic tools targeting other oxidative enzymes involved in the pathogenesis of vascular disease and inflammation.

Figure 23:
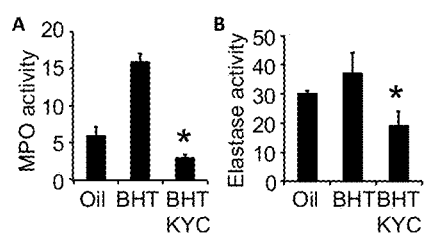
FIG. 23A. MPO activity in BALF as assayed on the 3rd day. KYC inhibits PMN degranulation in lung cancer mice. BHT was administered to the mice with KYC or with PBS. p<0.01.
FIG. 23B. Elastase activity in BALF as assayed on the 3rd day. KYC inhibits PMN degranulation in lung cancer mice. p<0.01.
Figure 24:
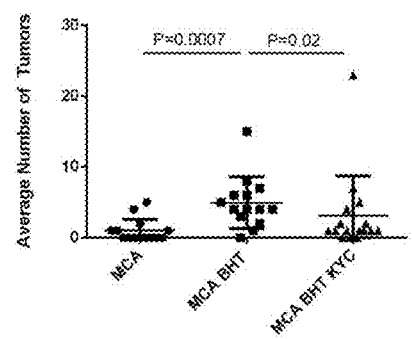
FIG. 24. KYC inhibits the number of tumors in BHT treated mice. BHT was administered to the mice with KYC or with PBS for 6 weeks. At the end of the study period the number of tumors were counted.

Inhibiting MPO decreases PMN degranulation in lung cancer mice. PMNs are considered to play a causal role in initiating tumor formation. Effects of KYC on PMN recruitment and tumor formation in lung cancer mice were determined. Briefly, mice were treated with BHT (single dose: 300 mg/kg) and KYC (0.3 mg/kg/d). After 3 days, KYC significantly decreased elastase and MPO activities in BALF although KYC did not reduce the PMN number in BALF (FIGS. 23-24). These data demonstrate that inhibiting MPO activity in vivo decreases PMN activation/degranulation, which leads to a decrease in PMN-dependent inflammation. These results begin to explain how just 6 weeks of KYC treatment significantly decreased the number of tumors in the mice (~50%) compared to untreated mice (p=0.02) examined later.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

We claim:

1. A method of inhibiting peroxidase activity in a subject, the method comprising administering to the subject a peptide-based peroxidase inhibitor having the formula $AA_1$-$AA_2$-$AA_3$, wherein $AA_1$ is a positively charged, negatively charged or neutral amino acid, $AA_2$ is a redox active amino acid, and $AA_3$ is an amino acid possessing a reducing potential such that $AA_3$ is capable of undergoing a redox reaction with a radical of amino acid $AA_2$; or a retro or retro-inverso analog thereof.

2. The method according to claim 1 wherein $AA_1$ is lysine, arginine, or histidine and $AA_2$ is tyrosine, tryptophan, chlorotyrosine, nitrotyrosine, or dimethyltyrosine and $AA_3$ is cysteine, selenocysteine, or homocysteine.

3. The method according to claim 1 wherein the peptide-based peroxidase inhibitor has the formula KYC or KWC.

4. The method according to claim 1 wherein the peptide-based peroxidase inhibitor has the retro or retro-inverso formula of KYC or KWC.

5. The method according to claim 1 wherein the peptide-based peroxidase inhibitor comprises L-amino acids or D-amino acids.

6. The method according to claim 1 wherein the peptide-based peroxidase inhibitor further comprises a protecting group coupled to its amino or carboxyl terminus.

7. The method according to claim 1 wherein the peptide-based peroxidase inhibitor further comprises a first protecting group coupled to the amino terminus and a second protecting group coupled to the carboxyl terminus.

8. The method according to claim 1 wherein the peptide-based peroxidase inhibitor comprises an acetyl protecting group coupled to its amino terminus or an amide protecting group coupled to its carboxyl terminus.

9. The method according to claim 1 wherein the peptide-based peroxidase inhibitor comprises an acetyl protecting group coupled to its amino terminus and an amide protecting group coupled to its carboxyl terminus.

10. The method according to claim 1 wherein the peptide-based peroxidase inhibitor has the formula Ac-KYC-amide or Ac-KWC-amide.

11. The method according to claim 1 wherein said method results in the treatment of a disease or condition attributable to aberrant peroxidase activity in the subject.

12. The method according to claim 1 wherein the disease or condition attributable to aberrant peroxidase activity is selected from the group consisting of wound inflammation, hypersensitivity, digestive disease, cardiovascular disease, neuronal disease, lung disease, autoimmune disease, degenerative neurological disease, degenerative muscle disease, infectious disease, disease associated with graft transplantation, allergic disease, musculo-skeletal inflammation, sepsis, hypertension, peripheral vascular disease, pulmonary inflammation, asthma, atherosclerosis, diabetes, persistent pulmonary hypertension, sickle cell disease, neurodegenerative disease, multiple sclerosis, Alzheimer's disease, lung cancer, lupus, ischemic heart disease, Parkinson's disease, Crone's disease, inflammatory bowel disease, necrotizing enterocolitis, arthritis, polymyocytis, cardiomyopathy, psoriasis, amyotrophic lateral sclerosis, muscular dystrophy, cystic fibrosis, attention deficiency hyperactive disorder, acute lung injury, acute respiratory distress syndrome, swine flu, heart failure, chemotherapy-induced heart failure, arthritis, rheumatoid arthritis, and acute myocardial infarction.

13. The method according to claim 1 wherein said method results in the promotion of angiogenesis in a tissue of the subject.

14. The method according to claim 13 wherein said method results in the promotion of angiogenesis impaired by persistent pulmonary hypertension, peripheral vascular disease or vascular disease in the myocardium in the subject.

15. The method according to claim 1 wherein said method results in the treatment of a disease or condition associated with abnormal, excessive blood vessel development in the subject.

16. The method according to claim 1 wherein said method results in a reduction in ischemic injury to the subject's heart.

17. A peptide-based peroxidase inhibitor having the formula $AA_1$-$AA_2$-$AA_3$, wherein $AA_1$ is a positively charged, negatively charged or neutral amino acid, $AA_2$ is a redox active amino acid, and $AA_3$ is an amino acid possessing a reducing potential such that $AA_3$ is capable of undergoing a redox reaction with a radical of amino acid $AA_2$; or a retro or retro-inverso analog thereof.

18. The peptide-based peroxidase inhibitor according to claim 17 wherein $AA_1$ is lysine, arginine, or histidine and $AA_2$ is tyrosine, tryptophan, chlorotyrosine, nitrotyrosine, or dimethyltyrosine and $AA_3$ is cysteine, selenocysteine, or homocysteine.

19. The peptide-based peroxidase inhibitor according to claim 17 comprising the formula KYC or KWC.

20. The peptide-based peroxidase inhibitor according to claim 17 comprising the retro or retro-inverso formula of KYC or KWC.

21. The peptide-based peroxidase inhibitor according to claim 17 comprising L-amino acids or D-amino acids.

22. The peptide-based peroxidase inhibitor according to claim 17 further comprising a protecting group coupled to the amino or carboxyl terminus.

23. The peptide-based peroxidase inhibitor according to claim 17 further comprising a first protecting group coupled to the amino terminus and a second protecting group coupled to the carboxyl terminus.

24. The peptide-based peroxidase inhibitor according to claim 17 comprising an acetyl protecting group coupled to its amino terminus or an amide protecting group coupled to its carboxyl terminus.

25. The peptide-based peroxidase inhibitor according to claim 17 comprising an acetyl protecting group coupled to its amino terminus and an amide protecting group coupled to its carboxyl terminus.

26. The peptide-based peroxidase inhibitor according to claim 17 comprising the formula Ac-KYC-amide or Ac-KWC-amide.

27. A pharmaceutical composition capable of inhibiting peroxidase activity in a subject, comprising the peptide-based peroxidase inhibitor of claim 17 and a pharmaceutically acceptable carrier.

28. A method of making a pharmaceutical composition capable of inhibiting peroxidase activity in a subject, comprising the steps of (a) providing a peptide-based inhibitor according to claim 17; and (b) mixing the peptide-based inhibitor with a pharmaceutically acceptable carrier to yield the pharmaceutical composition.

29. A method of inhibiting peroxidase activity in a subject, the method comprising administering to the subject a peptide-based peroxidase inhibitor consisting of (a) the tripeptide KYC, or (b) the tripeptide KYC having a protecting group coupled to its amino terminus, its carboxyl terminus, or to both its amino and carboxyl termini.

30. The method according to claim 29 wherein all the amino acids in the peptide-based peroxidase inhibitor are L-amino acids.

31. The method according to claim 29 wherein an acetyl protecting group is coupled to the amino terminus of the tripeptide, and an amide protecting group is coupled to the carboxyl terminus of the tripeptide.

32. The method according to claim 29 wherein said method results in the prevention or treatment of a disease or condition attributable to aberrant peroxidase activity in the subject.

33. The method according to claim 32 wherein the disease or condition attributable to aberrant peroxidase activity is a vascular disease or lung cancer.

34. The method of claim 33, wherein the vascular disease is atherosclerosis.

35. The method of claim 33, wherein lung cancer is effectively treated or prevented.

* * * * *